United States Patent
King et al.

(10) Patent No.: US 6,512,091 B1
(45) Date of Patent: Jan. 28, 2003

(54) GENETIC MARKERS FOR BREAST, OVARIAN, AND PROSTATIC CANCER

(75) Inventors: Mary-Claire King, Berkeley; Lori Friedman; Beth Ostermeyer, both of Albany; Sarah Rowell, Kensington; Eric Lynch, Albany; Csilla Szabo, Richmond; Ming Lee, Union City, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/989,890

(22) Filed: Dec. 12, 1997

Related U.S. Application Data

(63) Continuation of application No. 08/825,886, filed on Apr. 2, 1997, which is a division of application No. 08/425,061, filed on Apr. 19, 1995, now Pat. No. 5,622,829, which is a continuation of application No. 08/326,983, filed on Oct. 20, 1994, now abandoned, which is a continuation of application No. 08/232,535, filed on Apr. 18, 1994, now abandoned, which is a continuation of application No. 08/163,959, filed on Dec. 8, 1993, now abandoned.

(51) Int. Cl.$^7$ .......................... A61K 38/00; C12Q 1/00; G01N 33/53; G01N 33/566
(52) U.S. Cl. ........................... 530/300; 435/4; 435/7.1; 436/501
(58) Field of Search ...................... 435/4, 7.1; 436/501; 530/300, 350, 387.1, 387.7

(56) References Cited

U.S. PATENT DOCUMENTS

| | | | | | |
|---|---|---|---|---|---|
| 4,742,000 A | * | 5/1988 | Greene et al. | ................. | 435/7 |
| 5,597,707 A | * | 1/1997 | Marken et al. | ............ | 435/69.3 |
| 5,821,328 A | * | 10/1998 | King et al. | ................. | 530/300 |

OTHER PUBLICATIONS

Miki et al. A strong candidate for the breast and ovarian cancer susceptibility gene GRCA1. Science, vol. 266, pp. 66–71, (Oct. 7, 1994).*
Shattuck–Eidens et al. A collaborative survey of 80 mutations in the BRCA1 breast and ovarian cancer susceptibility gene. JAMA, vol. 273(7), pp. 535–541 (Feb. 15, 1995).*
Sequence Homology Search.*

* cited by examiner

*Primary Examiner*—John S. Brusca
*Assistant Examiner*—Young Kim
(74) *Attorney, Agent, or Firm*—Richard Aron Osman

(57) ABSTRACT

Specific BRCA1 mutations, PCR primers and hybridization probes are used in nucleic acid-based methods for diagnostic of inheritable breast cancer susceptibility. Additionally, binding agents, such as antibodies, specific for peptides encoded by the subject BRCA1 mutants are used to identify expression products of diagnostic mutations/rare alleles in patient derived fluid or tissue samples. Compositions with high binding affinity for transcription or translation products of the disclosed BRCA1 mutations and alleles are used in therapeutic intervention. Such products include anti-sense nucleic acids, peptides encoded by the subject nucleic acids, and binding agents such as antibodies, specific for such peptides.

13 Claims, No Drawings

GENETIC MARKERS FOR BREAST, OVARIAN, AND PROSTATIC CANCER

CROSS-REFERENCE TO RELATED APPLICATION

This application is a continuing application of U.S. patent application Ser. No. 08/825,886, now allowed, which is a divisional application of U.S. patent application Ser. No. 08/425,061, filed Apr. 19, 1995, issued as U.S. Pat. No. 5,622,829 on Apr. 22, 1997, which is a continuing application of U.S. patent application Ser. No. 08/326,983, filed Oct. 20, 1994, now abandoned, which is a continuing application of U.S. patent application Ser. No. 08/232,535, filed Apr. 18, 1994, now abandoned, which is a continuing application of U.S. patent application Ser. No. 08/163,959, filed Dec. 8, 1993, now abandoned.

The research carried out in the subject application was supported in part by grants from the National Institutes of Health. The government may have rights in any patent issuing on this application.

INTRODUCTION

1. Field of the Invention

The field of the invention is genetic markers for inheritable breast cancer susceptibility.

2. Background

The largest proportion of inherited breast cancer described so far has been attributed to a genetic locus, the BRCA1 locus, on chromosome 17q21 (Hall et al. 1990 Science 250:1684–1689; Narod et al. 1991 Lancet 338:82–83; Easton et al. 1993 Am J Hum Genet 52:678–701). Background material on the genetic markers for breast cancer screening is found in the Jan 29, 1993 issue of Science, vol 259, especially pages 622–625; see also King et al., 1993 J Amer Med Assoc 269:1975–198. Other relevant research papers include King (1992) Nature Genet 2:125–126; Merette et al. (1992) Amer J Human Genet 50:515–519; NIH/CEPH Collaborative Mapping Group (1992) Science 258:67–86.

Risks of breast cancer to women inheriting the locus are extremely high, exceeding 50% before age 50 and reaching 80% by age 65 (Newman et al. 1988 Proc Natl Acad Sci USA 85:3044–3048; Hall et al. 1992 Amer J Human Genet 50:1235–1242; Easton et al. 1993). Epidemiological evidence for inherited susceptibility to ovarian cancer is even stronger (Cramer et al. 1983 J Natl Cancer Inst 71:711–716; Schildkraut & Thompson 1988 Amer J Epidemiol 128:456–466; Schildkraut et al. 1989 Amer J Hum Genet 45:521–529). According to one study, more than 90% of families with multiple relatives with breast and ovarian cancer trace disease susceptibility to chromosome 17q21 (Easton et al. 1993).

The link between increasing risk of breast and ovarian cancer and inherited susceptibility to these diseases lies in the application of genetics to diagnosis and prevention. Creating molecular tools for earlier diagnosis and developing ways to reverse the first steps of tumorigenesis may be the most effective means of breast and ovarian cancer control.

Our laboratory previously mapped the heritable breast cancer susceptibility gene locus (BRCA1 locus) to a 50 cM region of chromosome 17q (Hall et al. 1990). More recently, we developed new polymorphisms at ERBB2 (Hall and King 1991 Nucl Acids Res 19:2515), THRA1 (Bowcock et al. 1993 Amer J Human Genet 52:718–722), EDH17B (Friedman et al. 1993 Hum Molec Genet 2:821), and multiple anonymous loci (Anderson et al. 1993 Genomics 17:616–623), ultimately developing a high density map of 17q12-q21 (Anderson et al. 1993; see also, Simard et al. 1993 Human Molec Genet 2:1193–1199). We also added families to the genetic study; there are now 100 families for whom transformed lymphocyte lines have been established and all informative relatives genotyped. We used our new markers and the many chromosome 17q polymorphisms developed in the past three years to test linkage in our families, refining the region first to 8 cM (Hall et al. 1992), then to 4 cM (Bowcock et al. 1993), then to 1 Mb based on polymorphisms from our high density map (Anderson et al. 1993; see also Flejter et al., 1993 Genomics 17:624–631). We disclose here a number of mutations in BRCA1 which correlate with disease.

Relevant Literature

The predicted amino acid sequence for a BRCA1 cDNA and familial studies of this gene were described by Miki et al. (1994) Science 266, 66–71 and Futeal et al. (1994) Science 266, 120–122. A study of Canadian cancer families is described in Simard et al. (1994) Nature Genetics 8, 392–398. A collaborative survey of BRCA1 mutations is described in Shattuch-Eidens et al. (1995) JAMA 273, 535–541.

SUMMARY OF THE INVENTION

The invention discloses methods and compositions useful in the diagnosis and treatment of breast and ovarian cancer associated with mutations and/or rare alleles of BRCA1, a breast cancer susceptibility gene. Specific genetic probes diagnostic of inheritable breast cancer susceptibility and methods of use are provided. Labelled nucleic acid probes comprising sequences complementary to specified BRCA1 alleles are hybridized to clinical nucleic acid samples. Linkage analysis and inheritance patterns of the disclosed markers are used to diagnose genetic susceptibility. In addition, BRCA1 mutations and/or rare alleles are directly identified by hybridization, polymorphism and or sequence analysis. In another embodiment, labeled binding agents, such as antibodies, specific for peptides encoded by the subject nucleic acids are used to identify expression products of diagnostic mutations or alleles in patient derived fluid or tissue samples. For therapeutic intervention, the invention provides compositions which can functionally interfere with the transcription or translation products of the breast and ovarian cancer susceptibility associated mutations and/or rare alleles within BRCA1. Such products include anti-sense nucleic acids, competitive peptides encoded by the subject nucleic acids, and high affinity binding agents such as antibodies, specific for e.g. translation products of the disclosed BRCA1 mutations and alleles.

DESCRIPTION OF SPECIFIC EMBODIMENTS

We disclose here methods and compositions for determining the presence or absence of BRCA1 mutations and rare alleles or translation products thereof which are useful in the diagnosis of breast and ovarian cancer susceptibility. Tumorigenic BRCA1 alleles include BRCA1 allele #5803 (SEQUENCE ID NO:1), 9601 (SEQUENCE ID NO:2), 9815 (SEQUENCE ID NO:3), 8403 (SEQUENCE ID NO:4), 8203 (SEQUENCE ID NO:5), 388 (SEQUENCE ID NO:6), 6401 (SEQUENCE ID NO:7), 4406 (SEQUENCE ID NO:8), 10201 (SEQUENCE ID NO:9), 7408 (SEQUENCE ID NO:10), 582 (SEQUENCE ID NO:11) or 77 (SEQUENCE ID NO:12). These nucleic acids or fragments capable of specifically hybridizing with the corresponding allele in the presence of other BRCA1 alleles under stringent conditions find broad diagnostic and therapeutic application. Gene products of the disclosed mutant and/or rare BRCA1 alleles also find a broad range of therapeutic and diagnostic applications. For example, mutant and/or rare allelic BRCA1 peptides are used to generate specific binding compounds. Binding reagents are used diagnostically to distinguish non-tumorigenic wild-type and tumorigenic BRCA1 translation products.

The subject nucleic acids (including fragments thereof) may be single or double stranded and are isolated, partially purified, and/or recombinant. An "isolated" nucleic acid is present as other than a naturally occurring chromosome or transcript in its natural state and isolated from (not joined in sequence to) at least one nucleotide with which it is normally associated on a natural chromosome; a partially pure nucleic acid constitutes at least about 10%, preferably at least about 30%, and more preferably at least about 90% by weight of total nucleic acid present in a given fraction; and a recombinant nucleic acid is joined in sequence to at least one nucleotide with which it is not normally associated on a natural chromosome.

Fragments of the disclosed alleles are sufficiently long for use as specific hybridization probes for detecting endogenous alleles, and particularly to distinguish the disclosed critical rare or mutant alleles which correlate with cancer susceptibility from other BRCA1 alleles, including alleles encoding the BRCA1 translation product displayed in Miki et al (1994) supra, under stringent conditions. Preferred fragments are capable of hybridizing to the corresponding mutant allele under stringency conditions characterized by a hybridization buffer comprising 0% formamide in 0.9 M saline/0.09 M sodium citrate (SSC) buffer at a temperature of 37° C. and remaining bound when subject to washing at 42° C. with the SSC buffer at 37° C. More preferred fragments will hybridize in a hybridization buffer comprising 20% formamide in 0.9 M saline/0.09 M sodium citrate (SSC) buffer at a temperature of 42° C. and remaining bound when subject to washing at 42° C. with 2×SSC buffer at 42° C. In any event, the fragments are necessarily of length sufficient to be unique to the corresponding allele; i.e. has a nucleotide sequence at least long enough to define a novel oligonucleotide, usually at least about 14, 16, 18, 20, 22, or 24 bp in length, though such fragment may be joined in sequence to other nucleotides which may be nucleotides which naturally flank the fragment.

In many applications, the nucleic acids are labelled with directly or indirectly detectable signals or means for amplifying a detectable signal. Examples include radiolabels, luminescent (e.g. fluorescent) tags, components of amplified tags such antigen-labelled antibody, biotin-avidin combinations etc. The nucleic acids can be subject to purification, synthesis, modification, sequencing, recombination, incorporation into a variety of vectors, expression, transfection, administration or methods of use disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art.

The subject nucleic acids are used in a wide variety of nucleic acid-based diagnostic method that are known to those in the art. Exemplary methods include their use as allele-specific oligonucleotide probes (ASOs), in ligase mediated methods for detecting mutations, as primers in PCR-based methods, direct sequencing methods wherein the clinical BRCA1 nucleic acid sequence is compared with the disclosed mutations and rare alleles, etc. The subject nucleic acids are capable of detecting the presence of a critical mutant or rare BRCA1 allele in a sample and distinguishing the mutant or rare allele from other BRCA1 alleles. For example, where the subject nucleic acids are used as PCR primers or hybridization probes the subject primer or probe comprises an oligonucleotide complementary to a strand of the mutant or rare allele of length sufficient to selectively hybridize with the mutant or rare allele. Generally, these primers and probes comprise at least 16 bp to 24 bp complementary to the mutant or rare allele and may be as large as is convenient for the hybridizations conditions.

Where the critical mutation is a deletion of wild-type sequence, useful primers/probes require wild-type sequences flanking (both sides) the deletion with at least 2, usually at least 3, more usually at least 4, most usually at least 5 bases. Where the mutation is an insertion or substitution which exceeds about 20 bp, it is generally not necessary to include wild-type sequence in the probes/primers. For insertions or substitutions of fewer than 5 bp, preferred nucleic acid portions comprise and flank the substitution/insertion with at least 2, preferably at least 3, more preferably at least 4, most preferably at least 5 bases. For substitutions or insertions from about 5 to about 20 bp, it is usually necessary to include both the entire insertion/substitution and at least 2, usually at least 3, more usually at least 4, most usually at least 5 basis of wild-type sequence of at least one flank of the substitution/insertion.

In addition to their use as diagnostic genetic probes and primers, BRCA1 nucleic acids are used to effect a variety of gene-based therapies. See, e.g. Zhu et al. (1993) Science 261, 209–211; Gutierrez et al. (1992) Lancet 339, 715–721; Gary Nabel lab (Dec 1993), Proc. Nat'l. Acad Sci USA. For example, therapeutic nucleic acids are used to modulate cellular expression or intracellular concentration or availability of a tumorigenic BRCA1 translation product by introducing into cells complements of the disclosed nucleic acids. These nucleic acids are typically antisense: single-stranded sequences comprising complements of the disclosed relevant BRCA1 mutant. Antisense modulation of the expression of a given mutant may employ antisense nucleic acids operably linked to gene regulatory sequences. Cell are transfected with a vector comprising such a sequence with a promoter sequence oriented such that transcription of the gene yields an antisense transcript capable of binding to the endogenous tumorigenic BRCA1 allele or transcript. Transcription of the antisense nucleic acid may be constitutive or inducible and the vector may provide for stable extrachromosomal maintenance or integration. Alternatively, single-stranded antisense nucleic acids that bind to BRCA1 genomic DNA or mRNA may be administered to the target cell, in or temporarily isolated from a host, at a concentration that results in a substantial reduction in expression of the targeted translation product.

Various techniques may be employed for introducing of the nucleic acids into viable cells. The techniques vary depending upon whether one is using the subject compositions in culture or in vivo in a host. Various techniques which have been found efficient include transfection with a retrovirus, viral coat protein-liposome mediated transfection, see Dzau et al., *Trends in Biotech* 11, 205–210 (1993). In some situations it is desirable to provide the nucleic acid source with an agent which targets the target cells, such as an antibody specific for a surface membrane protein on the target cell, a ligand for a receptor on the target cell, etc. Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. In liposomes, the decoy concentration in the lumen will generally be in the range of about 0.1 $\mu$M to 20 $\mu$M. For other techniques, the application rate is determined empirically, using conventional techniques to determine desired ranges. Usually, application of the subject therapeutics will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Systemic administration of the nucleic acid using lipofection, liposomes with tissue targeting (e.g. antibody) may also be employed.

The invention also provides isolated translation products of the disclosed BRCA1 allele which distinguish the wild type BRCA1 gene product. For example, for alleles which encode truncated tumorigenic translation product, the C-terminus is used to differentiate wild-type BRCA1. Accordingly, the invention provides the translation product of BRCA1 allele #5803 (SEQUENCE ID NO:13), 9601 (SEQUENCE ID NO:14), 9815 (SEQUENCE ID NO:15), 8203 (SEQUENCE ID NO:17), 388 (SEQUENCE ID NO:18), 6401 (SEQUENCE ID NO:19), 4406 (SEQUENCE ID NO:20), 10201 (SEQUENCE ID NO:21), 7408 (SEQUENCE ID NO:22), 582 (SEQUENCE ID NO:23) or 77 (SEQUENCE ID NO:24), or a C-terminus fragment thereof; and that of #8403 (SEQUENCE ID NO:16), or a fragment thereof comprising Gly at position 61.

The subject mutant and/or rare allelic BRCA1 translation products comprise an amino acid sequence which provides a target for distinguishing the product from that of other BRCA1 alleles. Preferred fragments are capable of eliciting the production of a peptide-specific antibody, in vivo or in vitro, capable of distinguishing a protein comprising the immunogenic peptide from a wild-type BRCA1 translation product. The fragments are necessarily unique to the disclosed allele translation product in that it is not found in any previously known protein and has a length at least long enough to define a novel peptide, from about 5 to about 25 residues, preferably from 6 to 10 residues in length, depending on the particular amino acid sequence.

The subject translation products (including fragments) are either isolated, i.e. unaccompanied by at least some of the material with which they are associated in their natural state); partially purified, i.e. constituting at least about 1%, preferably at least about 10%, and more preferably at least about 50% by weight of the total translation product in a given sample; or pure, i.e. at least about 60%, preferably at least 80%, and more preferably at least about 90% by weight of total translation product. Included in the subject translation product weight are any atoms, molecules, groups, etc. covalently coupled to the subject translation products, such as detectable labels, glycosylations, phosphorylations, etc. The subject translation products may be isolated, purified, modified or joined to other compounds in a variety of ways known to those skilled in the art depending on what other components are present in the sample and to what, if anything, the translation product is covalently linked.

Binding agents specific for the disclosed tumorigenic BRCA1 genes and gene products find particular use in cancer diagnosis. The selected method of diagnosis will depend on the nature of the tumorigenic BRCA1 mutants/ rare allele and its transcription or translation product(s). For example, soluble secreted translation products of the disclosed alleles may be detected in a variety of physiologic fluids using a binding agent with a detectable label such as a radiolabel, fluorescer etc. Detection of membrane bound or intracellular products generally requires preliminary isolation of cells (e.g. blood cells) or tissue (e.g. breast biopsy tissue). A wide variety of specific binding assays, e.g. ELISA, may be used.

BRCA1 gene product-specific binding agents are produced in a variety of ways using the compositions disclosed herein. For example, structural x-ray crystallographic and/or NMR data of the mutant and/or rare allelic BRCA1 translation products are used to rationally design binding molecules of determined structure or complementarity. Also, the disclosed mutant and/or rare allelic BRCA1 translation products-are used as immunogens to generate specific polyclonal or monoclonal antibodies. See, Harlow and Lane (1988) Antibodies, A Laboratory Manual, Cold Spring Harbor Laboratory, for general methods. Specific antibodies are readily modified to a monovalent form, such as Fab, Fab', or Fv.

Other mutant and/or rare allelic BRCA1 gene-product specific agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g. Houghten et al. and Lam et al (1991) Nature 354, 84 and 81, respectively and Blake and Litzi-Davis (1992), Bioconjugate Chem 3, 510.

Useful binding agents are identified with assays employing a compound comprising mutant and/or rare allelic BRCA1 peptides or encoding nucleic acids. A wide variety of in vitro, cell-free binding assays, especially assays for specific binding to immobilized compounds comprising the subject nucleic acid or translation product find convenient use. See, e.g. Fodor et al (1991) Science 251, 767 for the light directed parallel synthesis method. Such assays are amenable to scale-up, high throughput usage suitable for volume drug screening.

Useful agents are typically those that bind the targeted mutant and/or rare allelic BRCA1 gene product with high affinity and specificity and distinguish the tumorigenic BRCA1 mutants/rare alleles from the wild-type BRCA1 gene product. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, sterols, isoprenoids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means to enhance efficacy, stability, pharmaceutical compatibility, and the like. In addition, known pharmacological agents may be subject to directed or random chemical modifications, such as acylation, alkylation, esterification, amidification, etc., to produce structural analogs.

Therapeutic applications typically involve binding to and functional disruption of a tumorigenic BRCA1 gene product by an administered high affinity binding agent. For therapeutic uses, the compositions and agents disclosed herein may be administered by any convenient way. Small organics are preferably administered orally; other compositions and agents are preferably administered parenterally, conveniently in a pharmaceutically or physiologically acceptable carrier, e.g., phosphate buffered saline, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration will generally be in the range of about 50 to 500 µg/ml in the dose administered. Other additives may be included, such as stabilizers, bactericides, etc. These additives will be present in conventional amounts.

The following examples are offered by way of illustration and not by way of limitation.

EXAMPLES

Example 1

Positional Cloning Contig Construction

YACs. Primers flanking polymorphic repeats in the 4 Mb region of linkage were used to amplify pools from the CEPH, Washington University, and CEPH mega YAC libraries available. 39 YACs were selected. Of these, 23 were tested for chimerism by FISH and 12 found to be chimeric. YACs were aligned to each other by attempting to amplify each YAC with primer pairs from known sequence tagged sites (STSes). More STSes were defined by sequencing the ends of YACs, and these new STSes used for further alignment and YAC identification.

Cosmids. A gridded cosmid library of chromosome 17 was prepared. Alu—Alu PCR products of YACs were hybridized to the cosmid grids and positively hybridizing cosmids used for subsequent studies. Contigs were constructed in two ways. Cosmids with the same restriction patterns were aligned; and, the unique sequences flanking polymorphic markers and our sequenced cDNAs were used as STSes.

Physical mapping by pulsed field gel electrophoresis. Physical distances were estimated by pulsed field gel electrophoresis, using DNA from lymphocyte cell lines of BRCA1-linked patients and of controls. DNA samples were digested with NotI, MluI, RsrII, NruI, SacII, and EClXI. Filters were probed with single-copy sequences isolated from cosmids and later with cDNA clones. Multiple unrelated linked patients and controls were screened to detect large insertions or deletions associated with BRCA1. Results of PFGE were used to define the region first used to screen cDNA libraries as ~1 Mb and the current linked region as ≦500 kb.

Screening cDNA libraries. We began library screening when the linked region defined by meiotic recombination was ~1 Mb. The first question was what library would optimize the length of cDNA clones, representation of both 5' and 3' ends of genes, and the chances that BRCA1 would be expressed. We chose to use a random primed cDNA library cloned into lgt10 from cultured (not transformed) fibroblasts from a human female. This library was selected because it had inserts averaging 1.8 kb, with 80% of inserts between 1 and 4 kb, was contructed from cultured fibroblasts known to be "leaky" in gene expression, and was known to include 5' ends of genes. We simultaneously screened three other libraries (from ovary, fetal brain, and mouse mammary epithelium). With one exception (described below), all transcripts from these libraries cross-hybridized to transcripts from the fibroblast library.

The fibroblast library was screened with YAC DNA isolated by PFGE. Pure YAC DNA (100 nanograms) was random primed with both $aP^{32}$-dATP (6000 mCi/mmole) and $^{32}$P-dCTP (3000 mCi/mmole), and used immediately after labelling. Filters from the library were prehybridized with human placental DNA for 24–48 hours. Labelled YAC DNA was hybridized to the filters for 48 hours at 65C. Approximately 250 transcripts were selected by screening with 7 YACs and then ross-hybridized. We also used pools of cosmids from the linked region to screen the fibroblast library. We selected 122 transcripts and cross-hybridized them to clones previously detected by the YACs.

Example 2

Cloning BRCA1 and its Characterization

A. Screening for mutations in candidate genes. We initially identified 24 genes in the 1Mb BRCA1 region defined by meiotic recombination, respective locations on the YAC contig, sizes of representative cDNA clones, numbers of replicates in the library, sizes of transcripts, homologies to known genes, and variants detected. Candidate gene were characterized in the following ways:

(1) Cross-hybridizing clones. cDNA clones isolated from the library are hybridized against each other. Cross-hybridizing clones are considered "siblings" of the clone used as a probe and represent the same gene.

(2) Mapping back. At least one clone from each sibship is mapped back to total human genomic DNA, to cosmids, to YACs, and to somatic cell hybrid lines, some of which contain deletions of 17q and one of which has chromosome 17 as its only human chromosome.

(3) Subcloning and sequencing. One of the longest clones from each sibship is subcloned into M13 and sequenced manually by standard methods, constructing new primers at the end of each fragment to continue sequencing until the end of the clone is reached.

(4) Extending sequences with sibs. In order to find clones that contain more of the gene, the last sequencing primer for the clone and primers made from lgt10 are used to amplify sibs of the first clone. Sibs that amplify the longest fragments are selected, subcloned, and sequenced. This process is continued until we reach the size of the transcript defined by Northern blot and/or until the 3' sequence is a polyA tail and the 5' sequence has features of the beginning of the coding region.

(5) Southerns. To identify insertion or deletion mutations, genomic DNA from 20 unrelated patients from families with breast cancer linked to 17q (i.e. "linked patients") and controls are digested with BamI/TaqI and independently with HindIII/HinfI. Each cDNA clone is used to screen Southern blots. Variants have been detected in two genes. Both of these variants are RFLPs, occuring in equal frequency in linked patients and in controls.

(6) Northerns. To identify splice mutations and/or length mutations, we prepared total RNA and polyA+ RNA from germline DNA (from lymphoblast lines) of 20 unrelated linked patients, from ovarian and breast tissues, from fibroblasts, from a HeLa cell line, and from breast cancer cell lines. Northern blots are screened with each gene.

(7) Detection of small mutations. To screen for germline point mutations in patients without encountering introns, we prepared cDNA from poly-A+ mRNA from lymphoblast cell lines of 20 unrelated linked patients and from controls. cDNA has also been made from 65 malignant ovarian cancers from patients not selected for family history. Primers are constructed every ~200 basepairs along the sequence and used to amplify these cDNAs. Genomic DNA has also been prepared from cell lines from all family members (linked and unlinked), from malignant and normal cells from paraffin blocks from their breast and ovarian surgeries, and from malignant and normal cells from 29 breast tumors not selected for family history. For sequences without introns, cDNA and gDNA lengths are equal, and the gDNA samples are amplified as well.

Two mutation detection methods are used to screen each sequence. Amplified products are screened for SSCPs using modifications that enable electrophoresis to be done with only one set of running conditions (Keen et al. 1991 Trends Genet 7:5; Soto and Sukumar 1992 PCR Meth Appl 2:96–98). In order to screen longer segments of DNA (100–1500 bp) and to detect variants missed by SSCP, sequences are also screened for point mutations by CCM (Cotton 1993 Mutation Res 285:125–144) using essentially the protocol of Grompe et al. 1989 Proc Natl Acad Sci USA 86:5888–5892. An endonuclease developed for mismatch detection reduces the toxicity of the method (Youil et al. 1993 Amer J Hum Genet 53 (supplement): abstract 1257).

(8) Polymorphism or mutation. Variants are screened in cases and controls to distinguish polymorphisms from a critical mutation. Linkage of breast cancer to each variant is tested in all informative families.

Example 3

Characterize BRCA1 Mutations in Germline DNA and Breast Cancer Patients Tumors

A. BRCA1 mutations in chromosome 17q-linked families. Our series of families includes 20 large extended kindreds in which breast and ovarian cancer (and in one family prostatic cancer) are linked to 17q21, with individual lod scores >1.5. Since linked patients in these families carry mutations in BRCA1, we have identified their mutations first.

TABLE 1 summarizes critical BRCA 1 mutations and rare alleles:

| Family | Exon | U14680 nt | Mutation | Amino Acid change | Predicted effect |
|---|---|---|---|---|---|
| 5803 SEQ ID NO: 1 | 3 | 200–253 | exon 3 deleted (54 bp) | 27 Stop | protein truncation SEQ ID NO: 13 |
| 9601 SEQ ID NO: 2 | 3 | 230 | deletion AA | 39 Stop | protein truncation SEQ ID NO: 14 |
| 9815 SEQ ID NO: 3 | Intron 5 | splice donor, bp + 1 | substitution G to A -> bp deletion (base pairs 310–331) in RNA | 64 Stop | protein truncation SEQ ID NO: 15 |
| 8403 SEQ ID NO: 4 | 5 | 300 | substitution T to G | Cys 61 Gly | lose zinc-binding motif SEQ ID NO: 16 |
| 8203 SEQ ID NO: 5 | Intron 5 | splice acceptor, bp − 11 | substitution T to G -> 59 bp insertion of intron into RNA (at base pair 331) | 81 Stop | protein truncation SEQ ID NO: 17 |
| 388 SEQ ID NO: 6 | 11 | 1048 | deletion A | 313 Stop | protein truncation SEQ ID NO: 18 |
| 6401 SEQ ID NO: 7 | 11 | 2415 | deletion AG | Ser 766 Stop | protein truncation SEQ ID NO: 19 |
| 4406 SEQ ID NO: 8 | 11 | 2800 | deletion AA | 901 Stop | protein truncation SEQ ID NO: 20 |
| 10201 SEQ ID NO: 9 | 11 | 2863 | deletion TC | Ser 915 Stop | protein truncation SEQ ID NO: 21 |
| 7408 SEQ ID NO: 10 | 11 | 3726 | substitution C to T | Arg 1203 Stop | protein truncation SEQ ID NO: 22 |
| 582 SEQ ID NO: 11 | 11 | 4184 | deletion TCAA | 1364 Stop | protein truncation SEQ ID NO: 23 |
| 77 SEQ ID NO: 12 | 24 | 5677 | Insertion A | Tyr 1853 Stop | protein truncation SEQ ID NO: 24 |

B. Germline BRCA1 mutations among breast cancer patients in the general population. From each breast cancer patient, not selected for family history, a 30 ml sample of whole blood is drawn into acid citrate dextrose. DNA from the blood is extracted and stored at −70C in 3 aliquots. Germline mutations in BRCA1 are identified using the approaches described above and by directly sequencing new mutations. Paraffin-embedded tumor specimens from the same patients are screened for alterations of p53, HER2, PRAD1, and ER. Germline BRCA1 mutations are tested in the tumor blocks.

A preliminary estimate of risk associated with different BRCA1 mutations is obtained from relatives of patients with germline alterations. For each patient with a germline BRCA1 mutation, each surviving sister and mother (and for older patients, brothers as well), DNA is extracted from a blood sample and tested for the presence of the proband's BRCA1 mutation. To ascertain men at risk of prostatic cancer, brothers of breast cancer patients diagnosed after age 55 are also interviewed and sampled. Paraffin blocks from deceased relatives who had cancer are also screened. The frequency of breast, ovarian, or prostatic cancer among relatives carrying BRCA1 mutations is a first estimate of risk of these cancers associated with different mutations.

C. Somatic alterations of BRCA1 in breast tumors.

Malignant cells are dissected from normal cells from paraffin blocks. By identifying BRCA1 mutations in these series, we estimate the frequency of somatic BRCA1 alterations, determine BRCA1 mutations characteristic of any particular stage of tumor development, and evaluate their association with prognosis.

D. Characterizing mutant and rare alleles of BRCA1.

Mutant or rare BRCA1 allele function and pattern of expression during development are characterized using transformed cells expressing the allele and knockout or transgenic mice. For example, phenotypic changes in the animal or cell line, such as growth rate and anchorage independence are determined. In addition, several methods are used to study loss-of-function mutations, including replacing normal genes with their mutant alleles (BRCA1-/BRCA1-) by homologous recombination in embryonic stem (ES) cells and replacing mutant alleles with their normal counterparts in differentiated cultured cells (Capecchi 1989 Science 244:1288–1292; Weissman et al. 1987 Science 236:175–180; Wang et al. 1993 Oncogene 8:279–288). Breast carcinoma cell lines are screened for mutation at the BRCA1 locus and a mutant BRCA1 line is selected. Normal and mutant cDNAs of BRCA1 are subcloned into an expression vector carrying genes which confer resistance to ampicillin and geneticin (Baker et al. 1990 Nature 249:912–915). Subclones are transfected into mutant BRCA1 breast cancer cells Geneticin-resistant colonies are isolated and examined for any change in tumorigenic phenotype, such as colony formation in soft agar, increased growth rate, and/or tumor formation in athymic nude mice. In vivo functional demonstrations involve introducing the normal BCRA1 gene into a breast carcinoma cell line mutant at BRCA1 and injecting these BRCA1+ cells into nude mice. Changes observed in tumorigenic growth compared to nude mice injected with BRCA1 mutant breast carcinoma cells are readily observed. For example, correcting the mutant gene decreases the ability of the breast carcinoma cells to form tumors in nude mice (Weissman et al. 1987; Wang et al. 1993).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of screening a patient for a breast, ovarian or prostatic cancer susceptibility, said method comprising the steps of:

detecting in said patient or in a sample derived from said patient, the presence or absence of the translation product of BRCA1 allele #5803 (SEQ ID NO:13), 9601 (SEQ ID NO:14), 9815 (SEQ ID NO:15), 8203 (SEQ ID NO:17), 388 (SEQ ID NO:18), 6401 (SEQ ID NO:19), 4406 (SEQ ID NO:20), 10201 (SEQ ID NO:21), 7408 (SEQ ID NO:22), 582 (SEQ ID NO:23) or 77 (SEQ ID NO:24), or the translation product of BRCA1 allele #8403 (SEQ ID NO:16), wherein the presence of said translation product is diagnostic of a breast, ovarian or prostatic cancer susceptibility.

2. A method according to claim 1, comprising detecting in said patient or in a sample derived from said patient, the presence or absence of the translation product of BRCA1 allele #5803 (SEQ ID NO:13).

3. A method according to claim 1, comprising detecting in said patient or in a sample derived from said patient, the presence or absence of the translation product of BRCA1 allele #9601 (SEQ ID NO:14).

4. A method according to claim 1, comprising detecting in said patient or in a sample derived from said patient, the presence or absence of the translation product of BRCA1 allele #9815 (SEQ ID NO:15).

5. A method according to claim 1, comprising detecting in said patient or in a sample derived from said patient, the presence or absence of the translation product of BRCA1 allele #8203 (SEQ ID NO:17).

6. A method according to claim 1, comprising detecting in said patient or in a sample derived from said patient, the presence or absence of the translation product of BRCA1 allele #388 (SEQ ID NO:18).

7. A method according to claim 1, comprising detecting in said patient or in a sample derived from said patient, the presence or absence of the translation product of BRCA1 allele #6401 (SEQ ID NO:19).

8. A method according to claim 1, comprising detecting in said patient or in a sample derived from said patient, the presence or absence of the translation product of BRCA1 allele #4406 (SEQ ID NO:20).

9. A method according to claim 1, comprising detecting in said patient or in a sample derived from said patient, the presence or absence of the translation product of BRCA1 allele #10201 (SEQ ID NO:21).

10. A method according to claim 1, comprising detecting in said patient or in a sample derived from said patient, the presence or absence of the translation product of BRCA1 allele #7408 (SEQ ID NO:22).

11. A method according to claim 1, comprising detecting in said patient or in a sample derived from said patient, the presence or absence of the translation product of BRCA1 allele #582 (SEQ ID NO:23).

12. A method according to claim 1, comprising detecting in said patient or in a sample derived from said patient, the presence or absence of the translation product of BRCA1 allele #77 (SEQ ID NO:24).

13. A method according to claim 1, comprising detecting in said patient or in a sample derived from said patient, the presence or absence of the translation product of BRCA1 allele #8403 (SEQ ID NO:16).

\* \* \* \* \*

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 5656 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO: 1:

```
AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAA     120

TGGATTTATC TGCTCTTCGC GTTGAAGAAG TACAAAATGT CATTAATGCT ATGCAGAAAA     180

TCTTAGAGTG TCCCATCTGA TTTTGCATGC TGAAACTTCT CAACCAGAAG AAAGGGCCTT     240

CACAGTGTCC TTTATGTAAG AATGATATAA CCAAAAGGAG CCTACAAGAA AGTACGAGAT     300

TTAGTCAACT TGTTGAAGAG CTATTGAAAA TCATTTGTGC TTTTCAGCTT GACACAGGTT     360

TGGAGTATGC AAACAGCTAT AATTTTGCAA AAAAGGAAAA TAACTCTCCT GAACATCTAA     420

AAGATGAAGT TTCTATCATC CAAAGTATGG GCTACAGAAA CCGTGCCAAA AGACTTCTAC     480

AGAGTGAACC CGAAAATCCT TCCTTGCAGG AAACCAGTCT CAGTGTCCAA CTCTCTAACC     540

TTGGAACTGT GAGAACTCTG AGGACAAAGC AGCGGATACA ACCTCAAAAG ACGTCTGTCT     600
```

```
ACATTGAATT GGGATCTGAT TCTTCTGAAG ATACCGTTAA TAAGGCAACT TATTGCAGTG    660

TGGGAGATCA AGAATTGTTA CAAATCACCC CTCAAGGAAC CAGGGATGAA ATCAGTTTGG    720

ATTCTGCAAA AAAGGCTGCT TGTGAATTTT CTGAGACGGA TGTAACAAAT ACTGAACATC    780

ATCAACCCAG TAATAATGAT TTGAACACCA CTGAGAAGCG TGCAGCTGAG AGGCATCCAG    840

AAAAGTATCA GGGTAGTTCT GTTTCAAACT TGCATGTGGA GCCATGTGGC ACAAATACTC    900

ATGCCAGCTC ATTACAGCAT GAGAACAGCA GTTTATTACT CACTAAAGAC AGAATGAATG    960

TAGAAAAGGC TGAATTCTGT AATAAAAGCA AACAGCCTGG CTTAGCAAGG AGCCAACATA   1020

ACAGATGGGC TGGAAGTAAG GAAACATGTA ATGATAGGCG GACTCCCAGC ACAGAAAAAA   1080

AGGTAGATCT GAATGCTGAT CCCCTGTGTG AGAGAAAAGA ATGGAATAAG CAGAAACTGC   1140

CATGCTCAGA GAATCCTAGA GATACTGAAG ATGTTCCTTG GATAACACTA AATAGCAGCA   1200

TTCAGAAAGT TAATGAGTGG TTTTCCAGAA GTGATGAACT GTTAGGTTCT GATGACTCAC   1260

ATGATGGGGA GTCTGAATCA AATGCCAAAG TAGCTGATGT ATTGGACGTT CTAAATGAGG   1320

TAGATGAATA TTCTGGTTCT TCAGAGAAAA TAGACTTACT GGCCAGTGAT CCTCATGAGG   1380

CTTTAATATG TAAAAGTGAA AGAGTTCACT CCAAATCAGT AGAGAGTAAT ATTGAAGACA   1440

AAATATTTGG GAAAACCTAT CGGAAGAAGG CAAGCCTCCC CAACTTAAGC CATGTAACTG   1500

AAAATCTAAT TATAGGAGCA TTTGTTACTG AGCCACAGAT AATACAAGAG CGTCCCCTCA   1560

CAAATAAATT AAAGCGTAAA AGGAGACCTA CATCAGGCCT TCATCCTGAG GATTTTATCA   1620

AGAAAGCAGA TTTGGCAGTT CAAAAGACTC CTGAAATGAT AAATCAGGGA ACTAACCAAA   1680

CGGAGCAGAA TGGTCAAGTG ATGAATATTA CTAATAGTGG TCATGAGAAT AAAACAAAAG   1740

GTGATTCTAT TCAGAATGAG AAAAATCCTA ACCCAATAGA ATCACTCGAA AAAGAATCTG   1800

CTTTCAAAAC GAAAGCTGAA CCTATAAGCA GCAGTATAAG CAATATGGAA CTCGAATTAA   1860

ATATCCACAA TTCAAAAGCA CCTAAAAAGA ATAGGCTGAG GAGGAAGTCT TCTACCAGGC   1920

ATATTCATGC GCTTGAACTA GTAGTCAGTA GAAATCTAAG CCCACCTAAT TGTACTGAAT   1980

TGCAAATTGA TAGTTGTTCT AGCAGTGAAG AGATAAAGAA AAAAAAGTAC AACCAAATGC   2040

CAGTCAGGCA CAGCAGAAAC CTACAACTCA TGGAAGGTAA AGAACCTGCA ACTGGAGCCA   2100

AGAAGAGTAA CAAGCCAAAT GAACAGACAA GTAAAAGACA TGACAGCGAT ACTTTCCCAG   2160

AGCTGAAGTT AACAAATGCA CCTGGTTCTT TTACTAAGTG TTCAAATACC AGTGAACTTA   2220

AAGAATTTGT CAATCCTAGC CTTCCAAGAG AAGAAAAAGA AGAGAAACTA GAAACAGTTA   2280

AAGTGTCTAA TAATGCTGAA GACCCCAAAG ATCTCATGTT AAGTGGAGAA AGGGTTTTGC   2340

AAACTGAAAG ATCTGTAGAG AGTAGCAGTA TTTCATTGGT ACCTGGTACT GATTATGGCA   2400

CTCAGGAAAG TATCTCGTTA CTGGAAGTTA GCACTCTAGG GAAGGCAAAA ACAGAACCAA   2460

ATAAATGTGT GAGTCAGTGT GCAGCATTTG AAAACCCCAA GGGACTAATT CATGGTTGTT   2520

CCAAAGATAA TAGAAATGAC ACAGAAGGCT TTAAGTATCC ATTGGGACAT GAAGTTAACC   2580

ACAGTCGGGA AACAAGCATA GAAATGGAAG AAAGTGAACT TGATGCTCAG TATTTGCAGA   2640

ATACATTCAA GGTTTCAAAG CGCCAGTCAT TTGCTCCGTT TTCAAATCCA GGAAATGCAG   2700

AAGAGGAATG TGCAACATTC TCTGCCCACT CTGGGTCCTT AAAGAAACAA AGTCCAAAAG   2760

TCACTTTTGA ATGTGAACAA AAGGAAGAAA ATCAAGGAAA GAATGAGTCT AATATCAAGC   2820

CTGTACAGAC AGTAAATATC ACTGCAGGCT TTCCTGTGGT TGGTCAGAAA GATAAGCCAG   2880

TTGATAATGC CAAATGTAGT ATCAAAGGAG GCTCTAGGTT TTGTCTATCA TCTCAGTTCA   2940

GAGGCAACGA AACTGGACTC ATTACTCCAA ATAAACATGG ACTTTTACAA AACCCATATC   3000
```

-continued

```
GTATACCACC ACTTTTTCCC ATCAAGTCAT TTGTTAAAAC TAAATGTAAG AAAAATCTGC    3060

TAGAGGAAAA CTTTGAGGAA CATTCAATGT CACCTGAAAG AGAAATGGGA AATGAGAACA    3120

TTCCAAGTAC AGTGAGCACA ATTAGCCGTA ATAACATTAG AGAAAATGTT TTTAAAGAAG    3180

CCAGCTCAAG CAATATTAAT GAAGTAGGTT CCAGTACTAA TGAAGTGGGC TCCAGTATTA    3240

ATGAAATAGG TTCCAGTGAT GAAAACATTC AAGCAGAACT AGGTAGAAAC AGAGGGCCAA    3300

AATTGAATGC TATGCTTAGA TTAGGGGTTT TGCAACCTGA GGTCTATAAA CAAAGTCTTC    3360

CTGGAAGTAA TTGTAAGCAT CCTGAAATAA AAAAGCAAGA ATATGAAGAA GTAGTTCAGA    3420

CTGTTAATAC AGATTTCTCT CCATATCTGA TTTCAGATAA CTTAGAACAG CCTATGGGAA    3480

GTAGTCATGC ATCTCAGGTT TGTTCTGAGA CACCTGATGA CCTGTTAGAT GATGGTGAAA    3540

TAAAGGAAGA ACTAGTTTTT GCTGAAAATG ACATTAAGGA AAGTTCTGCT GTTTTTAGCA    3600

AAAGCGTCCA GAAAGGAGAG CTTAGCAGGA GTCCTAGCCC TTTCACCCAT ACACATTTGG    3660

CTCAGGGTTA CCGAAGAGGG GCCAAGAAAT TAGAGTCCTC AGAAGAGAAC TTATCTAGTG    3720

AGGATGAAGA GCTTCCCTGC TTCCAACACT TGTTATTTGG TAAAGTAAAC AATATACCTT    3780

CTCAGTCTAC TAGGCATAGC ACCGTTGCTA CCGAGTGTCT GTCTAAGAAC ACAGAGGAGA    3840

ATTTATTATC ATTGAAGAAT AGCTTAAATG ACTGCAGTAA CCAGGTAATA TTGGCAAAGG    3900

CATCTCAGGA ACATCACCTT AGTGAGGAAA CAAAATGTTC TGCTAGCTTG TTTTCTTCAC    3960

AGTGCAGTGA ATTGGAAGAC TTGACTGCAA ATACAAACAC CCAGGATCCT TTCTTGATTG    4020

GTTCTTCCAA ACAAATGAGG CATCAGTCTG AAAGCCAGGG AGTTGGTCTG AGTGACAAGG    4080

AATTGGTTTC AGATGATGAA GAAAGAGGAA CGGGCTTGGA AGAAAATAAT CAAGAAGAGC    4140

AAAGCATGGA TTCAAACTTA GGTGAAGCAG CATCTGGGTG TGAGAGTGAA ACAAGCGTCT    4200

CTGAAGACTG CTCAGGGCTA TCCTCTCAGA GTGACATTTT AACCACTCAG CAGAGGGATA    4260

CCATGCAACA TAACCTGATA AAGCTCCAGC AGGAAATGGC TGAACTAGAA GCTGTGTTAG    4320

AACAGCATGG GAGCCAGCCT TCTAACAGCT ACCCTTCCAT CATAAGTGAC TCTTCTGCCC    4380

TTGAGGACCT GCGAAATCCA GAACAAAGCA CATCAGAAAA AGCAGTATTA ACTTCACAGA    4440

AAAGTAGTGA ATACCCTATA AGCCAGAATC CAGAAGGCCT TTCTGCTGAC AAGTTTGAGG    4500

TGTCTGCAGA TAGTTCTACC AGTAAAAATA AAGAACCAGG AGTGGAAAGG TCATCCCCTT    4560

CTAAATGCCC ATCATTAGAT GATAGGTGGT ACATGCACAG TTGCTCTGGG AGTCTTCAGA    4620

ATAGAAACTA CCCATCTCAA GAGGAGCTCA TTAAGGTTGT TGATGTGGAG GAGCAACAGC    4680

TGGAAGAGTC TGGGCCACAC GATTTGACGG AAACATCTTA CTTGCCAAGG CAAGATCTAG    4740

AGGGAACCCC TTACCTGGAA TCTGGAATCA GCCTCTTCTC TGATGACCCT GAATCTGATC    4800

CTTCTGAAGA CAGAGCCCCA GAGTCAGCTC GTGTTGGCAA CATACCATCT TCAACCTCTG    4860

CATTGAAAGT TCCCCAATTG AAAGTTGCAG AATCTGCCCA GAGTCCAGCT GCTGCTCATA    4920

CTACTGATAC TGCTGGGTAT AATGCAATGG AAGAAAGTGT GAGCAGGGAG AAGCCAGAAT    4980

TGACAGCTTC AACAGAAAGG GTCAACAAAA GAATGTCCAT GGTGGTGTCT GGCCTGACCC    5040

CAGAAGAATT TATGCTCGTG TACAAGTTTG CCAGAAAACA CCACATCACT TTAACTAATC    5100

TAATTACTGA AGAGACTACT CATGTTGTTA TGAAAACAGA TGCTGAGTTT GTGTGTGAAC    5160

GGACACTGAA ATATTTTCTA GGAATTGCGG GAGGAAAATG GGTAGTTAGC TATTTCTGGG    5220

TGACCCAGTC TATTAAAGAA AGAAAAATGC TGAATGAGCA TGATTTTGAA GTCAGAGGAG    5280

ATGTGGTCAA TGGAAGAAAC CACCAAGGTC CAAAGCGAGC AAGAGAATCC CAGGACAGAA    5340
```

-continued

| | |
|---|---|
| AGATCTTCAG GGGGCTAGAA ATCTGTTGCT ATGGGCCCTT CACCAACATG CCCACAGATC | 5400 |
| AACTGGAATG GATGGTACAG CTGTGTGGTG CTTCTGTGGT GAAGGAGCTT TCATCATTCA | 5460 |
| CCCTTGGCAC AGGTGTCCAC CCAATTGTGG TTGTGCAGCC AGATGCCTGG ACAGAGGACA | 5520 |
| ATGGCTTCCA TGCAATTGGG CAGATGTGTG AGGCACCTGT GGTGACCCGA GAGTGGGTGT | 5580 |
| TGGACAGTGT AGCACTCTAC CAGTGCCAGG AGCTGGACAC CTACCTGATA CCCCAGATCC | 5640 |
| CCCACAGCCA CTACTG | 5656 |

(2) INFORMATION FOR SEQ ID NO: 2:

(i) SEQUENCE CHARACTERISTICS:
        (A) LENGTH: 5709 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 2:

| | |
|---|---|
| AGCTCGCTGA GACTTCCTGG ACCCCGCACC AGGCTGTGGG GTTTCTCAGA TAACTGGGCC | 60 |
| CCTGCGCTCA GGAGGCCTTC ACCCTCTGCT CTGGGTAAAG TTCATTGGAA CAGAAAGAAA | 120 |
| TGGATTTATC TGCTCTTCGC GTTGAAGAAG TACAAAATGT CATTAATGCT ATGCAGAAAA | 180 |
| TCTTAGAGTG TCCCATCTGT CTGGAGTTGA TCAAGGAACC TGTCTCCACA GTGTGACCAC | 240 |
| ATATTTTGCA AATTTTGCAT GCTGAAACTT CTCAACCAGA AGAAAGGGCC TTCACAGTGT | 300 |
| CCTTTATGTA AGAATGATAT AACCAAAAGG AGCCTACAAG AAAGTACGAG ATTTAGTCAA | 360 |
| CTTGTTGAAG AGCTATTGAA AATCATTTGT GCTTTTCAGC TTGACACAGG TTTGGAGTAT | 420 |
| GCAAACAGCT ATAATTTTGC AAAAAAGGAA AATAACTCTC CTGAACATCT AAAAGATGAA | 480 |
| GTTTCTATCA TCCAAAGTAT GGGCTACAGA AACCGTGCCA AAAGACTTCT ACAGAGTGAA | 540 |
| CCCGAAAATC CTTCCTTGCA GGAAACCAGT CTCAGTGTCC AACTCTCTAA CCTTGGAACT | 600 |
| GTGAGAACTC TGAGGACAAA GCAGCGGATA CAACCTCAAA GACGTCTGT CTACATTGAA | 660 |
| TTGGGATCTG ATTCTTCTGA AGATACCGTT AATAAGGCAA CTTATTGCAG TGTGGGAGAT | 720 |
| CAAGAATTGT TACAAATCAC CCCTCAAGGA ACCAGGGATG AAATCAGTTT GGATTCTGCA | 780 |
| AAAAAGGCTG CTTGTGAATT TTCTGAGACG GATGTAACAA ATACTGAACA TCATCAACCC | 840 |
| AGTAATAATG ATTTGAACAC CACTGAGAAG CGTGCAGCTG AGAGGCATCC AGAAAAGTAT | 900 |
| CAGGGTAGTT CTGTTTCAAA CTTGCATGTG GAGCCATGTG GCACAAATAC TCATGCCAGC | 960 |
| TCATTACAGC ATGAGAACAG CAGTTTATTA CTCACTAAAG ACAGAATGAA TGTAGAAAAG | 1020 |
| GCTGAATTCT GTAATAAAAG CAAACAGCCT GGCTTAGCAA GGAGCCAACA TAACAGATGG | 1080 |
| GCTGGAAGTA AGGAAACATG TAATGATAGG CGGACTCCCA GCACAGAAAA AAAGGTAGAT | 1140 |
| CTGAATGCTG ATCCCCTGTG TGAGAGAAAA GAATGGAATA AGCAGAAACT GCCATGCTCA | 1200 |
| GAGAATCCTA GAGATACTGA AGATGTTCCT TGGATAACAC TAAATAGCAG CATTCAGAAA | 1260 |
| GTTAATGAGT GGTTTTCCAG AAGTGATGAA CTGTTAGGTT CTGATGACTC ACATGATGGG | 1320 |
| GAGTCTGAAT CAAATGCCAA AGTAGCTGAT GTATTGGACG TTCTAAATGA GGTAGATGAA | 1380 |
| TATTCTGGTT CTTCAGAGAA AATAGACTTA CTGGCCAGTG ATCCTCATGA GGCTTTAATA | 1440 |
| TGTAAAAGTG AAAGAGTTCA CTCCAAATCA GTAGAGAGTA ATATTGAAGA CAAAATATTT | 1500 |
| GGGAAAACCT ATCGGAAGAA GGCAAGCCTC CCCAACTTAA GCCATGTAAC TGAAAATCTA | 1560 |
| ATTATAGGAG CATTTGTTAC TGAGCCACAG ATAATACAAG AGCGTCCCCT CACAAATAAA | 1620 |

-continued

```
TTAAAGCGTA AAAGGAGACC TACATCAGGC CTTCATCCTG AGGATTTTAT CAAGAAAGCA      1680

GATTTGGCAG TTCAAAAGAC TCCTGAAATG ATAAATCAGG GAACTAACCA AACGGAGCAG      1740

AATGGTCAAG TGATGAATAT TACTAATAGT GGTCATGAGA ATAAAACAAA AGGTGATTCT      1800

ATTCAGAATG AGAAAAATCC TAACCCAATA GAATCACTCG AAAAGAATC TGCTTTCAAA       1860

ACGAAAGCTA AACCTATAAG CAGCAGTATA AGCAATATGG AACTCGAATT AAATATCCAC      1920

AATTCAAAAG CACCTAAAAA GAATAGGCTG AGGAGGAAGT CTTCTACCAG GCATATTCAT      1980

GCGCTTGAAC TAGTAGTCAG TAGAAATCTA AGCCCACCTA ATTGTACTGA ATTGCAAATT     2040

GATAGTTGTT CTAGCAGTGA AGAGATAAAG AAAAAAAGT ACAACCAAAT GCCAGTCAGG      2100

CACAGCAGAA ACCTACAACT CATGGAAGGT AAAGAACCTG CAACTGGAGC CAAGAAGAGT     2160

AACAAGCCAA ATGAACAGAC AAGTAAAAGA CATGACAGCG ATACTTTCCC AGAGCTGAAG     2220

TTAACAAATG CACCTGGTTC TTTTACTAAG TGTTCAAATA CCAGTGAACT TAAAGAATTT     2280

GTCAATCCTA GCCTTCCAAG AGAAGAAAAA GAAGAGAAAC TAGAAACAGT TAAAGTGTCT    2340

AATAATGCTG AAGACCCCAA AGATCTCATG TTAAGTGGAG AAAGGGTTTT GCAAACTGAA    2400

AGATCTGTAG AGAGTAGCAG TATTTCATTG GTACCTGGTA CTGATTATGG CACTCAGGAA    2460

AGTATCTCGT TACTGGAAGT TAGCACTCTA GGGAAGGCAA AAACAGAACC AAATAAAATGT   2520

GTGAGTCAGT GTGCAGCATT TGAAAACCCC AAGGGACTAA TTCATGGTTG TTCCAAAGAT    2580

AATAGAAATG ACACAGAAGG CTTTAAGTAT CCATTGGGAC ATGAAGTTAA CCACAGTCGG    2640

GAAACAAGCA TAGAAATGGA AGAAAGTGAA CTTGATGCTC AGTATTTGCA GAATACATTC    2700

AAGGTTTCAA AGCGCCAGTC ATTTGCTCCG TTTTCAAATC CAGGAAATGC AGAAGAGGAA    2760

TGTGCAACAT TCTCTGCCCA CTCTGGGTCC TTAAAGAAAC AAAGTCCAAA AGTCACTTTT    2820

GAATGTGAAC AAAAGGAAGA AAATCAAGGA AAGAATGAGT CTAATATCAA GCCTGTACAG   2880

ACAGTTAATA TCACTGCAGG CTTTCCTGTG GTTGGTCAGA AGATAAGCC AGTTGATAAT    2940

GCCAAATGTA GTATCAAAGG AGGCTCTAGG TTTTGTCTAT CATCTCAGTT CAGAGGCAAC   3000

GAAACTGGAC TCATTACTCC AAATAAACAT GGACTTTTAC AAAACCCATA TCGTATACCA    3060

CCACTTTTTC CCATCAAGTC ATTTGTTAAA ACTAAATGTA AGAAAATCT GCTAGAGGAA    3120

AACTTTGAGG AACATTCAAT GTCACCTGAA AGAGAAATGG AAATGAGAA CATTCCAAGT     3180

ACAGTGAGCA CAATTAGCCG TAATAACATT AGAGAAAATG TTTTTAAAGA AGCCAGCTCA   3240

AGCAATATTA TGAAGTAGG TTCCAGTACT AATGAAGTGG GCTCCAGTAT TAATGAAATA    3300

GGTTCCAGTG ATGAAAACAT TCAAGCAGAA CTAGGTAGAA ACAGAGGGCC AAAATTGAAT    3360

GCTATGCTTA GATTAGGGGT TTTGCAACCT GAGGTCTATA AACAAAGTCT TCCTGGAAGT    3420

AATTGTAAGC ATCCTGAAAT AAAAAGCAA GAATATGAAG AAGTAGTTCA GACTGTTAAT    3480

ACAGATTTCT CTCCATATCT GATTTCAGAT AACTTAGAAC AGCCTATGGG AAGTAGTCAT   3540

GCATCTCAGG TTTGTTCTGA GACACCTGAT GACCTGTTAG ATGATGGTGA AATAAAGGAA   3600

GATACTAGTT TTGCTGAAAA TGACATTAAG GAAAGTTCTG CTGTTTTTAG CAAAAGCGTC    3660

CAGAAAGGAG AGCTTAGCAG GAGTCCTAGC CCTTTCACCC ATACACATTT GGCTCAGGGT    3720

TACCGAAGAG GGGCCAAGAA ATTAGAGTCC TCAGAAGAGA ACTTATCTAG TGAGGATGAA    3780

GAGCTTCCCT GCTTCCAACA CTTGTTATTT GGTAAAGTAA ACAATATACC TTCTCAGTCT    3840

ACTAGGCATA GCACCGTTGC TACCGAGTGT CTGTCTAAGA ACACAGAGGA GAATTTATTA    3900

TCATTGAAGA ATAGCTTAAA TGACTGCAGT AACCAGGTAA TATTGGCAAA GGCATCTCAG    3960

GAACATCACC TTAGTGAGGA AACAAAATGT TCTGCTAGCT TGTTTTCTTC ACAGTGCAGT    4020
```

-continued

```
GAATTGGAAG ACTTGACTGC AAATACAAAC ACCCAGGATC CTTTCTTGAT TGGTTCTTCC    4080

AAACAAATGA GGCATCAGTC TGAAAGCCAG GGAGTTGGTC TGAGTGACAA GGAATTGGTT    4140

TCAGATGATG AAGAAAGAGG AACGGGCTTG GAAGAAAATA ATCAAGAAGA GCAAAGCATG    4200

GATTCAAACT TAGGTGAAGC AGCATCTGGG TGTGAGAGTG AAACAAGCGT CTCTGAAGAC    4260

TGCTCAGGGC TATCCTCTCA GAGTGACATT TTAACCACTC AGCAGAGGGA TACCATGCAA    4320

CATAACCTGA TAAAGCTCCA GCAGGAAATG GCTGAACTAG AAGCTGTGTT AGAACAGCAT    4380

GGGAGCCAGC CTTCTAACAG CTACCCTTCC ATCATAAGTG ACTCTTCTGC CCTTGAGGAC    4440

CTGCGAAATC CAGAACAAAG CACATCAGAA AAAGCAGTAT TAACTTCACA GAAAAGTAGT    4500

GAATACCCTA TAAGCCAGAA TCCAGAAGGC CTTTCTGCTG ACAAGTTTGA GGTGTCTGCA    4560

GATAGTTCTA CCAGTAAAAA TAAAGAACCA GGAGTGGAAA GGTCATCCCC TTCTAAATGC    4620

CCATCATTAG ATGATAGGTG GTACATGCAC AGTTGCTCTG GAGTCTTCA GAATAGAAAC    4680

TACCCATCTC AAGAGGAGCT CATTAAGGTT GTTGATGTGG AGGAGCAACA GCTGGAAGAG    4740

TCTGGGCCAC ACGATTTGAC GGAAACATCT TACTTGCCAA GGCAAGATCT AGAGGGAACC    4800

CCTTACCTGG AATCTGGAAT CAGCCTCTTC TCTGATGACC CTGAATCTGA TCCTTCTGAA    4860

GACAGAGCCC CAGAGTCAGC TCGTGTTGGC AACATACCAT CTTCAACCTC TGCATTGAAA    4920

GTTCCCCAAT TGAAAGTTGC AGAATCTGCC CAGAGTCCAG CTGCTGCTCA TACTACTGAT    4980

ACTGCTGGGT ATAATGCAAT GGAAGAAAGT GTGAGCAGGG AGAAGCCAGA ATTGACAGCT    5040

TCAACAGAAA GGGTCAACAA AGAATGTCC ATGGTGGTGT CTGGCCTGAC CCCAGAAGAA    5100

TTTATGCTCG TGTACAAGTT TGCCAGAAAA CACCACATCA CTTTAACTAA TCTAATTACT    5160

GAAGAGACTA CTCATGTTGT TATGAAAACA GATGCTGAGT TTGTGTGTGA ACGGACACTG    5220

AAATATTTTC TAGGAATTGC GGGAGGAAAA TGGGTAGTTA GCTATTTCTG GGTGACCCAG    5280

TCTATTAAAG AAAGAAAAAT GCTGAATGAG CATGATTTTG AAGTCAGAGG AGATGTGGTC    5340

AATGGAAGAA ACCACCAAGG TCCAAAGCGA GCAAGAGAAT CCCAGGACAG AAAGATCTTC    5400

AGGGGGCTAG AAATCTGTTG CTATGGGCCC TTCACCAACA TGCCCACAGA TCAACTGGAA    5460

TGGATGGTAC AGCTGTGTGG TGCTTCTGTG GTGAAGGAGC TTTCATCATT CACCCTTGGC    5520

ACAGGTGTCC ACCCAATTGT GGTTGTGCAG CCAGATGCCT GGACAGAGGA CAATGGCTTC    5580

CATGCAATTG GCAGATGTGT TGAGGCACCT GTGGTGACCC GAGAGTGGGT GTTGGACAGT    5640

GTAGCACTCT ACCAGTGCCA GGAGCTGGAC ACCTACCTGA TACCCCAGAT CCCCCACAGC    5700

CACTACTGA                                                          5709
```

(2) INFORMATION FOR SEQ ID NO: 3:

(i) SEQUENCE CHARACTERISTICS:
        (A) LENGTH: 5689 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

```
AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAA     120

TGGATTTATC TGCTCTTCGC GTTGAAGAAG TACAAAATGT CATTAATGCT ATGCAGAAAA     180

TCTTAGAGTG TCCCATCTGT CTGGAGTTGA TCAAGGAACC TGTCTCCACA AAGTGTGACC     240
```

| | |
|---|---|
| ACATATTTTG CAAATTTTGC ATGCTGAAAC TTCTCAACCA GAAGAAAGGG CCTTCACAGT | 300 |
| GTCCTTTATG AGCCTACAAG AAAGTACGAG ATTTAGTCAA CTTGTTGAAG AGCTATTGAA | 360 |
| AATCATTTGT GCTTTTCAGC TTGACACAGG TTTGGAGTAT GCAAACAGCT ATAATTTTGC | 420 |
| AAAAAAGGAA ATAACTCTC CTGAACATCT AAAAGATGAA GTTTCTATCA TCCAAAGTAT | 480 |
| GGGCTACAGA AACCGTGCCA AAAGACTTCT ACAGAGTGAA CCCGAAAATC CTTCCTTGCA | 540 |
| GGAAACCAGT CTCAGTGTCC AACTCTCTAA CCTTGGAACT GTGAGAACTC TGAGGACAAA | 600 |
| GCAGCGGATA CAACCTCAAA AGACGTCTGT CTACATTGAA TTGGGATCTG ATTCTTCTGA | 660 |
| AGATACCGTT AATAAGGCAA CTTATTGCAG TGTGGGAGAT CAAGAATTGT TACAAATCAC | 720 |
| CCCTCAAGGA ACCAGGGATG AAATCAGTTT GGATTCTGCA AAAAAGGCTG CTTGTGAATT | 780 |
| TTCTGAGACG GATGTAACAA ATACTGAACA TCATCAACCC AGTAATAATG ATTTGAACAC | 840 |
| CACTGAGAAG CGTGCAGCTG AGAGGCATCC AGAAAAGTAT CAGGGTAGTT CTGTTTCAAA | 900 |
| CTTGCATGTG GAGCCATGTG GCACAAATAC TCATGCCAGC TCATTACAGC ATGAGAACAG | 960 |
| CAGTTTATTA CTCACTAAAG ACAGAATGAA TGTAGAAAAG GCTGAATTCT GTAATAAAAG | 1020 |
| CAAACAGCCT GGCTTAGCAA GGAGCCAACA TAACAGATGG GCTGGAAGTA AGGAAACATG | 1080 |
| TAATGATAGG CGGACTCCCA GCACAGAAAA AAAGGTAGAT CTGAATGCTG ATCCCCTGTG | 1140 |
| TGAGAGAAAA GAATGGAATA AGCAGAAACT GCCATGCTCA GAGAATCCTA GAGATACTGA | 1200 |
| AGATGTTCCT TGGATAACAC TAAATAGCAG CATTCAGAAA GTTAATGAGT GGTTTTCCAG | 1260 |
| AAGTGATGAA CTGTTAGGTT CTGATGACTC ACATGATGGG GAGTCTGAAT CAAATGCCAA | 1320 |
| AGTAGCTGAT GTATTGGACG TTCTAAATGA GGTAGATGAA TATTCTGGTT CTTCAGAGAA | 1380 |
| AATAGACTTA CTGGCCAGTG ATCCTCATGA GGCTTTAATA TGTAAAAGTG AAAGAGTTCA | 1440 |
| CTCCAAATCA GTAGAGAGTA ATATTGAAGA CAAAATATTT GGGAAAACCT ATCGGAAGAA | 1500 |
| GGCAAGCCTC CCCAACTTAA GCCATGTAAC TGAAAATCTA ATTATAGGAG CATTTGTTAC | 1560 |
| TGAGCCACAG ATAATACAAG AGCGTCCCCT CACAAATAAA TTAAAGCGTA AAAGGAGACC | 1620 |
| TACATCAGGC CTTCATCCTG AGGATTTTAT CAAGAAAGCA GATTTGGCAG TTCAAAAGAC | 1680 |
| TCCTGAAATG ATAAATCAGG GAACTAACCA AACGGAGCAG AATGGTCAAG TGATGAATAT | 1740 |
| TACTAATAGT GGTCATGAGA ATAAAACAAA AGGTGATTCT ATTCAGAATG AGAAAAATCC | 1800 |
| TAACCCAATA GAATCACTCG AAAAAGAATC TGCTTTCAAA ACGAAAGCTG AACCTATAAG | 1860 |
| CAGCAGTATA AGCAATATGG AACTCGAATT AAATATCCAC AATTCAAAAG CACCTAAAAA | 1920 |
| GAATAGGCTG AGGAGGAAGT CTTCTACCAG GCATATTCAT GCGCTTGAAC TAGTAGTCAG | 1980 |
| TAGAAATCTA AGCCCACCTA ATTGTACTGA ATTGCAAATT GATAGTTGTT CTAGCAGTGA | 2040 |
| AGAGATAAAG AAAAAAAAGT ACAACCAAAT GCCAGTCAGG CACAGCAGAA ACCTACAACT | 2100 |
| CATGGAAGGT AAAGAACCTG CAACTGGAGC CAAGAAGAGT AACAAGCCAA ATGAACAGAC | 2160 |
| AAGTAAAAGA CATGACAGCG ATACTTTCCC AGAGCTGAAG TTAACAAATG CACCTGGTTC | 2220 |
| TTTTACTAAG TGTTCAAATA CCAGTGAACT TAAAGAATTT GTCAATCCTA GCCTTCCAAG | 2280 |
| AGAAGAAAAA GAAGAGAAAC TAGAAACAGT TAAAGTGTCT AATAATGCTG AAGACCCCAA | 2340 |
| AGATCTCATG TTAAGTGGAG AAAGGGTTTT GCAAACTGAA AGATCTGTAG AGAGTAGCAG | 2400 |
| TATTTCATTG GTACCTGGTA CTGATTATGG CACTCAGGAA AGTATCTCGT TACTGGAAGT | 2460 |
| TAGCACTCTA GGGAAGGCAA AAACAGAACC AAATAAATGT GTGAGTCAGT GTGCAGCATT | 2520 |
| TGAAAACCCC AAGGGACTAA TTCATGGTTG TTCCAAAGAT AATAGAAATG ACACAGAAGG | 2580 |

-continued

| | |
|---|---|
| CTTTAAGTAT CCATTGGGAC ATGAAGTTAA CCACAGTCGG GAAACAAGCA TAGAAATGGA | 2640 |
| AGAAAGTGAA CTTGATGCTC AGTATTTGCA GAATACATTC AAGGTTTCAA AGCGCCAGTC | 2700 |
| ATTTGCTCCG TTTTCAAATC CAGGAAATGC AGAAGAGGAA TGTGCAACAT TCTCTGCCCA | 2760 |
| CTCTGGGTCC TTAAAGAAAC AAAGTCCAAA AGTCACTTTT GAATGTGAAC AAAAGGAAGA | 2820 |
| AAATCAAGGA AAGAATGAGT CTAATATCAA GCCTGTACAG ACAGTTAATA TCACTGCAGG | 2880 |
| CTTTCCTGTG GTTGGTCAGA AGATAAGCC AGTTGATAAT GCCAAATGTA GTATCAAAGG | 2940 |
| AGGCTCTAGG TTTTGTCTAT CATCTCAGTT CAGAGGCAAC GAAACTGGAC TCATTACTCC | 3000 |
| AAATAAACAT GGACTTTTAC AAAACCCATA TCGTATACCA CCACTTTTTC CCATCAAGTC | 3060 |
| ATTTGTTAAA ACTAAATGTA AGAAAAATCT GCTAGAGGAA AACTTTGAGG AACATTCAAT | 3120 |
| GTCACCTGAA AGAGAAATGG GAAATGAGAA CATTCCAAGT ACAGTGAGCA CAATTAGCCG | 3180 |
| TAATAACATT AGAGAAAATG TTTTTAAAGA AGCCAGCTCA AGCAATATTA ATGAAGTAGG | 3240 |
| TTCCAGTACT AATGAAGTGG GCTCCAGTAT TAATGAAATA GGTTCCAGTG ATGAAAACAT | 3300 |
| TCAAGCAGAA CTAGGTAGAA ACAGAGGGCC AAAATTGAAT GCTATGCTTA GATTAGGGGT | 3360 |
| TTTGCAACCT GAGGTCTATA AACAAAGTCT TCCTGGAAGT AATTGTAAGC ATCCTGAAAT | 3420 |
| AAAAAAGCAA GAATATGAAG AAGTAGTTCA GACTGTTAAT ACAGATTTCT CTCCATATCT | 3480 |
| GATTTCAGAT AACTTAGAAC AGCCTATGGG AAGTAGTCAT GCATCTCAGG TTTGTTCTGA | 3540 |
| GACACCTGAT GACCTGTTAG ATGATGGTGA ATAAAGGAA GATACTAGTT TTGCTGAAAA | 3600 |
| TGACATTAAG GAAAGTTCTG CTGTTTTTAG CAAAAGCGTC CAGAAAGGAG AGCTTAGCAG | 3660 |
| GAGTCCTAGC CCTTTCACCC ATACACATTT GGCTCAGGGT TACCGAAGAG GGGCCAAGAA | 3720 |
| ATTAGAGTCC TCAGAAGAGA ACTTATCTAG TGAGGATGAA GAGCTTCCCT GCTTCCAACA | 3780 |
| CTTGTTATTT GGTAAAGTAA ACAATATACC TTCTCAGTCT ACTAGGCATA GCACCGTTGC | 3840 |
| TACCGAGTGT CTGTCTAAGA ACACAGAGGA GAATTTATTA TCATTGAAGA ATAGCTTAAA | 3900 |
| TGACTGCAGT AACCAGGTAA TATTGGCAAA GGCATCTCAG GAACATCACC TTAGTGAGGA | 3960 |
| AACAAAATGT TCTGCTAGCT TGTTTTCTTC ACAGTGCAGT GAATTGGAAG ACTTGACTGC | 4020 |
| AAATACAAAC ACCCAGGATC CTTTCTTGAT TGGTTCTTCC AAACAAATGA GGCATCAGTC | 4080 |
| TGAAAGCCAG GGAGTTGGTC TGAGTGACAA GGAATTGGTT TCAGATGATG AAGAAAGAGG | 4140 |
| AACGGGCTTG GAAGAAAATA ATCAAGAAGA GCAAAGCATG GATTCAAACT TAGGTGAAGC | 4200 |
| AGCATCTGGG TGTGAGAGTG AAAACAAGCGT CTCTGAAGAC TGCTCAGGGC TATCCTCTCA | 4260 |
| GAGTGACATT TTAACCACTC AGCAGAGGGA TACCATGCAA CATAACCTGA TAAAGCTCCA | 4320 |
| GCAGGAAATG GCTGAACTAG AAGCTGTGTT AGAACAGCAT GGGAGCCAGC CTTCTAACAG | 4380 |
| CTACCCTTCC ATCATAAGTG ACTCTTCTGC CCTTGAGGAC CTGCGAAATC CAGAACAAAG | 4440 |
| CACATCAGAA AAAGCAGTAT TAACTTCACA GAAAAGTAGT GAATACCCTA TAAGCCAGAA | 4500 |
| TCCAGAAGGC CTTTCTGCTG ACAAGTTTGA GGTGTCTGCA GATAGTTCTA CCAGTAAAAA | 4560 |
| TAAAGAACCA GGAGTGGAAA GGTCATCCCC TTCTAAATGC CCATCATTAG ATGATAGGTG | 4620 |
| GTACATGCAC AGTTGCTCTG GGAGTCTTCA GAATAGAAAC TACCCATCTC AAGAGGAGCT | 4680 |
| CATTAAGGTT GTTGATGTGG AGGAGCAACA GCTGGAAGAG TCTGGGCCAC ACGATTTGAC | 4740 |
| GGAAACATCT TACTTGCCAA GGCAAGATCT AGAGGGAACC CCTTACCTGG AATCTGGAAT | 4800 |
| CAGCCTCTTC TCTGATGACC CTGAATCTGA TCCTTCTGAA GACAGAGCCC CAGAGTCAGC | 4860 |
| TCGTGTTGGC AACATACCAT CTTCAACCTC TGCATTGAAA GTTCCCCAAT TGAAAGTTGC | 4920 |
| AGAATCTGCC CAGAGTCCAG CTGCTGCTCA TACTACTGAT ACTGCTGGGT ATAATGCAAT | 4980 |

```
GGAAGAAAGT GTGAGCAGGG AGAAGCCAGA ATTGACAGCT TCAACAGAAA GGGTCAACAA    5040

AAGAATGTCC ATGGTGGTGT CTGGCCTGAC CCCAGAAGAA TTTATGCTCG TGTACAAGTT    5100

TGCCAGAAAA CACCACATCA CTTTAACTAA TCTAATTACT GAAGAGACTA CTCATGTTGT    5160

TATGAAAACA GATGCTGAGT TTGTGTGTGA ACGGACACTG AAATATTTTC TAGGAATTGC    5220

GGGAGGAAAA TGGGTAGTTA GCTATTTCTG GGTGACCCAG TCTATTAAAG AAAGAAAAAT    5280

GCTGAATGAG CATGATTTTG AAGTCAGAGG AGATGTGGTC AATGGAAGAA ACCACCAAGG    5340

TCCAAAGCGA GCAAGAGAAT CCCAGGACAG AAAGATCTTC AGGGGGCTAG AAATCTGTTG    5400

CTATGGGCCC TTCACCAACA TGCCCACAGA TCAACTGGAA TGGATGGTAC AGCTGTGTGG    5460

TGCTTCTGTG GTGAAGGAGC TTTCATCATT CACCCTTGGC ACAGGTGTCC ACCCAATTGT    5520

GGTTGTGCAG CCAGATGCCT GGACAGAGGA CAATGGCTTC CATGCAATTG GGCAGATGTG    5580

TGAGGCACCT GTGGTGACCC GAGAGTGGGT GTTGGACAGT GTAGCACTCT ACCAGTGCCA    5640

GGAGCTGGAC ACCTACCTGA TACCCCAGAT CCCCCACAGC CACTACTGA               5689
```

(2) INFORMATION FOR SEQ ID NO: 4:

(i) SEQUENCE CHARACTERISTICS:
        (A) LENGTH: 5711 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 4:

```
AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAA     120

TGGATTTATC TGCTCTTCGC GTTGAAGAAG TACAAAATGT CATTAATGCT ATGCAGAAAA     180

TCTTAGAGTG TCCCATCTGT CTGGAGTTGA TCAAGGAACC TGTCTCCACA AAGTGTGACC     240

ACATATTTTG CAAATTTTGC ATGCTGAAAC TTCTCAACCA GAAGAAAGGG CCTTCACAGG     300

GTCCTTTATG TAAGAATGAT ATAACCAAAA GGAGCCTACA AGAAAGTACG AGATTTAGTC     360

AACTTGTTGA AGAGCTATTG AAAATCATTT GTGCTTTTCA GCTTGACACA GGTTTGGAGT     420

ATGCAAACAG CTATAATTTT GCAAAAAAGG AAAATAACTC TCCTGAACAT CTAAAAGATG     480

AAGTTTCTAT CATCCAAAGT ATGGGCTACA GAAACCGTGC CAAAAGACTT CTACAGAGTG     540

AACCCGAAAA TCCTTCCTTG CAGGAAACCA GTCTCAGTGT CCAACTCTCT AACCTTGGAA     600

CTGTGAGAAC TCTGAGGACA AAGCAGCGGA TACAACCTCA AAAGACGTCT GTCTACATTG     660

AATTGGGATC TGATTCTTCT GAAGATACCG TTAATAAGGC AACTTATTGC AGTGTGGGAG     720

ATCAAGAATT GTTACAAATC ACCCCTCAAG GAACCAGGGA TGAAATCAGT TTGGATTCTG     780

CAAAAAAGGC TGCTTGTGAA TTTTCTGAGA CGGATGTAAC AAATACTGAA CATCATCAAC     840

CCAGTAATAA TGATTTGAAC ACCACTGAGA AGCGTGCAGC TGAGAGGCAT CCAGAAAAGT     900

ATCAGGGTAG TTCTGTTTCA AACTTGCATG TGGAGCCATG TGGCACAAAT ACTCATGCCA     960

GCTCATTACA GCATGAGAAC AGCAGTTTAT TACTCACTAA AGACAGAATG AATGTAGAAA    1020

AGGCTGAATT CTGTAATAAA AGCAAACAGC CTGGCTTAGC AAGGAGCCAA CATAACAGAT    1080

GGGCTGGAAG TAAGGAAACA TGTAATGATA GGCGGACTCC CAGCACAGAA AAAAGGTAG     1140

ATCTGAATGC TGATCCCCTG TGTGAGAGAA AGAATGGAA TAAGCAGAAA CTGCCATGCT     1200

CAGAGAATCC TAGAGATACT GAAGATGTTC CTTGGATAAC ACTAAATAGC AGCATTCAGA    1260
```

-continued

```
AAGTTAATGA GTGGTTTTCC AGAAGTGATG AACTGTTAGG TTCTGATGAC TCACATGATG      1320

GGGAGTCTGA ATCAAATGCC AAAGTAGCTG ATGTATTGGA CGTTCTAAAT GAGGTAGATG      1380

AATATTCTGG TTCTTCAGAG AAAATAGACT TACTGGCCAG TGATCCTCAT GAGGCTTTAA      1440

TATGTAAAAG TGAAAGAGTT CACTCCAAAT CAGTAGAGAG TAATATTGAA GACAAAATAT      1500

TTGGGAAAAC CTATCGGAAG AAGGCAAGCC TCCCCAACTT AAGCCATGTA ACTGAAAATC      1560

TAATTATAGG AGCATTTGTT ACTGAGCCAC AGATAATACA AGAGCGTCCC CTCACAAATA      1620

AATTAAAGCG TAAAAGGAGA CCTACATCAG GCCTTCATCC TGAGGATTTT ATCAAGAAAG      1680

CAGATTTGGC AGTTCAAAAG ACTCCTGAAA TGATAAATCA GGGAACTAAC CAAACGGAGC      1740

AGAATGGTCA AGTGATGAAT ATTACTAATA GTGGTCATGA GAATAAAACA AAAGGTGATT      1800

CTATTCAGAA TGAGAAAAAT CCTAACCCAA TAGAATCACT CGAAAAGAA TCTGCTTTCA      1860

AAACGAAAGC TGAACCTATA AGCAGCAGTA TAAGCAATAT GGAACTCGAA TTAAATATCC      1920

ACAATTCAAA AGCACCTAAA AAGAATAGGC TGAGGAGGAA GTCTTCTACC AGGCATATTC      1980

ATGCGCTTGA ACTAGTAGTC AGTAGAAATC TAAGCCCACC TAATTGTACT GAATTGCAAA      2040

TTGATAGTTG TTCTAGCAGT GAAGAGATAA AGAAAAAAAA GTACAACCAA ATGCCAGTCA      2100

GGCACAGCAG AAACCTACAA CTCATGGAAG GTAAAGAACC TGCAACTGGA GCCAAGAAGA      2160

GTAACAAGCC AAATGAACAG ACAAGTAAAA GACATGACAG CGATACTTTC CCAGAGCTGA      2220

AGTTAACAAA TGCACCTGGT TCTTTTACTA AGTGTTCAAA TACCAGTGAA CTTAAAGAAT      2280

TTGTCAATCC TAGCCTTCCA AGAGAAGAAA AAGAAGAGAA ACTAGAAACA GTTAAAGTGT      2340

CTAATAATGC TGAAGACCCC AAAGATCTCA TGTTAAGTGG AGAAAGGGTT TTGCAAACTG      2400

AAAGATCTGT AGAGAGTAGC AGTATTTCAT TGGTACCTGG TACTGATTAT GGCACTCAGG      2460

AAAGTATCTC GTTACTGGAA GTTAGCACTC TAGGGAAGGC AAAAACAGAA CCAAATAAAT      2520

GTGTGAGTCA GTGTGCAGCA TTTGAAAACC CCAAGGGACT AATTCATGGT TGTTCCAAAG      2580

ATAATAGAAA TGACACAGAA GGCTTTAAGT ATCCATTGGG ACATGAAGTT AACCACAGTC      2640

GGGAAACAAG CATAGAAATG GAAGAAAGTG AACTTGATGC TCAGTATTTG CAGAATACAT      2700

TCAAGGTTTC AAAGCGCCAG TCATTTGCTC CGTTTTCAAA TCCAGGAAAT GCAGAAGAGG      2760

AATGTGCAAC ATTCTCTGCC CACTCTGGGT CCTTAAAGAA ACAAAGTCCA AAAGTCACTT      2820

TTGAATGTGA ACAAAAGGAA GAAAATCAAG GAAAGAATGA GTCTAATATC AAGCCTGTAC      2880

AGACAGTTAA TATCACTGCA GGCTTTCCTG TGGTTGGTCA GAAAGATAAG CCAGTTGATA      2940

ATGCCAAATG TAGTATCAAA GGAGGCTCTA GGTTTTGTCT ATCATCTCAG TTCAGAGGCA      3000

ACGAAACTGG ACTCATTACT CCAAATAAAC ATGGACTTTT ACAAAACCCA TATCGTATAC      3060

CACCACTTTT TCCCATCAAG TCATTTGTTA AAACTAAATG TAAGAAAAAT CTGCTAGAGG      3120

AAAACTTTGA GGAACATTCA ATGTCACCTG AAAGAGAAAT GGGAAATGAG AACATTCCAA      3180

GTACAGTGAG CACAATTAGC CGTAATAACA TTAGAGAAAA TGTTTTTAAA GAAGCCAGCT      3240

CAAGCAATAT TAATGAAGTA GGTTCCAGTA CTAATGAAGT GGGCTCCAGT ATTAATGAAA      3300

TAGGTTCCAG TGATGAAAAC ATTCAAGCAG AACTAGGTAG AAACAGAGGG CCAAAATTGA      3360

ATGCTATGCT TAGATTAGGG GTTTTGCAAC CTGAGGTCTA TAAACAAAGT CTTCCTGGAA      3420

GTAATTGTAA GCATCCTGAA ATAAAAAAGC AAGAATATGA AGAAGTAGTT CAGACTGTTA      3480

ATACAGATTT CTCTCCATAT CTGATTTCAG ATAACTTAGA ACAGCCTATG GGAAGTAGTC      3540

ATGCATCTCA GGTTTGTTCT GAGACACCTG ATGACCTGTT AGATGATGGT GAAATAAAGG      3600
```

```
AAGATACTAG TTTTGCTGAA AATGACATTA AGGAAAGTTC TGCTGTTTTT AGCAAAAGCG    3660
TCCAGAAAGG AGAGCTTAGC AGGAGTCCTA GCCCTTTCAC CCATACACAT TTGGCTCAGG    3720
GTTACCGAAG AGGGGCCAAG AAATTAGAGT CCTCAGAAGA GAACTTATCT AGTGAGGATG    3780
AAGAGCTTCC CTGCTTCCAA CACTTGTTAT TTGGTAAAGT AAACAATATA CCTTCTCAGT    3840
CTACTAGGCA TAGCACCGTT GCTACCGAGT GTCTGTCTAA GAACACAGAG GAGAATTTAT    3900
TATCATTGAA GAATAGCTTA AATGACTGCA GTAACCAGGT AATATTGGCA AAGGCATCTC    3960
AGGAACATCA CCTTAGTGAG GAAACAAAAT GTTCTGCTAG CTTGTTTTCT TCACAGTGCA    4020
GTGAATTGGA AGACTTGACT GCAAATACAA ACACCCAGGA TCCTTTCTTG ATTGGTTCTT    4080
CCAAACAAAT GAGGCATCAG TCTGAAAGCC AGGGAGTTGG TCTGAGTGAC AAGGAATTGG    4140
TTTCAGATGA TGAAGAAAGA GGAACGGGCT TGGAAGAAAA TAATCAAGAA GAGCAAAGCA    4200
TGGATTCAAA CTTAGGTGAA GCAGCATCTG GGTGTGAGAG TGAAACAAGC GTCTCTGAAG    4260
ACTGCTCAGG GCTATCCTCT CAGAGTGACA TTTTAACCAC TCAGCAGAGG GATACCATGC    4320
AACATAACCT GATAAAGCTC CAGCAGGAAA TGGCTGAACT AGAAGCTGTG TTAGAACAGC    4380
ATGGGAGCCA GCCTTCTAAC AGCTACCCTT CCATCATAAG TGACTCTTCT GCCCTTGAGG    4440
ACCTGCGAAA TCCAGAACAA AGCACATCAG AAAAAGCAGT ATTAACTTCA CAGAAAAGTA    4500
GTGAATACCC TATAAGCCAG AATCCAGAAG GCCTTTCTGC TGACAAGTTT GAGGTGTCTG    4560
CAGATAGTTC TACCAGTAAA AATAAAGAAC CAGGAGTGGA AAGGTCATCC CCTTCTAAAT    4620
GCCCATCATT AGATGATAGG TGGTACATGC ACAGTTGCTC TGGGAGTCTT CAGAATAGAA    4680
ACTACCCATC TCAAGAGGAG CTCATTAAGG TTGTTGATGT GGAGGAGCAA CAGCTGGAAG    4740
AGTCTGGGCC ACACGATTTG ACGGAAACAT CTTACTTGCC AAGGCAAGAT CTAGAGGGAA    4800
CCCCTTACCT GGAATCTGGA ATCAGCCTCT TCTCTGATGA CCCTGAATCT GATCCTTCTG    4860
AAGACAGAGC CCCAGAGTCA GCTCGTGTTG GCAACATACC ATCTTCAACC TCTGCATTGA    4920
AAGTTCCCCA ATTGAAAGTT GCAGAATCTG CCCAGAGTCC AGCTGCTGCT CATACTACTG    4980
ATACTGCTGG GTATAATGCA ATGGAAGAAA GTGTGAGCAG GGAGAAGCCA GAATTGACAG    5040
CTTCAACAGA AAGGGTCAAC AAAAGAATGT CCATGGTGGT GTCTGGCCTG ACCCCAGAAG    5100
AATTTATGCT CGTGTACAAG TTTGCCAGAA AACACCACAT CACTTTAACT AATCTAATTA    5160
CTGAAGAGAC TACTCATGTT GTTATGAAAA CAGATGCTGA GTTTGTGTGT GAACGGACAC    5220
TGAAATATTT TCTAGGAATT GCGGGAGGAA AATGGGTAGT TAGCTATTTC TGGGTGACCC    5280
AGTCTATTAA AGAAAGAAAA ATGCTGAATG AGCATGATTT TGAAGTCAGA GGAGATGTGG    5340
TCAATGGAAG AAACCACCAA GGTCCAAAGC GAGCAAGAGA ATCCCAGGAC AGAAAGATCT    5400
TCAGGGGGCT AGAAATCTGT TGCTATGGGC CCTTCACCAA CATGCCCACA GATCAACTGG    5460
AATGGATGGT ACAGCTGTGT GGTGCTTCTG TGGTGAAGGA GCTTTCATCA TTCACCCTTG    5520
GCACAGGTGT CCACCCAATT GTGGTTGTGC AGCCAGATGC CTGGACAGAG GACAATGGCT    5580
TCCATGCAAT TGGGCAGATG TGTGAGGCAC CTGTGGTGAC CCGAGAGTGG GTGTTGGACA    5640
GTGTAGCACT CTACCAGTGC CAGGAGCTGG ACACCTACCT GATACCCCAG ATCCCCCACA    5700
GCCACTACTG A                                                       5711
```

(2) INFORMATION FOR SEQ ID NO: 5:

(i) SEQUENCE CHARACTERISTICS:
        (A) LENGTH: 5770 base pairs
        (B) TYPE: nucleic acid
        (C) STRANDEDNESS: double (D) TOPOLOGY: linear (ii) MOLECULE TYPE: cDNA (xi) SEQUENCE DESCRIPTION: SEQ ID NO: 5:

```
AGCTCGCTGA GACTTCCTGG ACCCCGCACC AGGCTGTGGG GTTTCTCAGA TAACTGGGCC      60
CCTGCGCTCA GGAGGCCTTC ACCCTCTGCT CTGGGTAAAG TTCATTGGAA CAGAAAGAAA     120
TGGATTTATC TGCTCTTCGC GTTGAAGAAG TACAAAATGT CATTAATGCT ATGCAGAAAA     180
TCTTAGAGTG TCCCATCTGT CTGGAGTTGA TCAAGGAACC TGTCTCCACA AAGTGTGACC     240
ACATATTTTG CAAATTTTGC ATGCTGAAAC TTCTCAACCA GAAGAAAGGG CCTTCACAGT     300
GTCCTTTATG TAAGAATGAT ATAACCAAAA GTGTCCTTAA AAGGTTGATA ATCACTTGCT     360
GAGTGTGTTT CTCAAACAAG TTAATTTCAG GAGCCTACAA GAAAGTACGA GATTTAGTCA     420
ACTTGTTGAA GAGCTATTGA AAATCATTTG TGCTTTTCAG CTTGACACAG GTTTGGAGTA     480
TGCAAACAGC TATAATTTTG CAAAAAAGGA AAATAACTCT CCTGAACATC TAAAAGATGA     540
AGTTTCTATC ATCCAAAGTA TGGGCTACAG AAACCGTGCC AAAAGACTTC TACAGAGTGA     600
ACCCGAAAAT CCTTCCTTGC AGGAAACCAG TCTCAGTGTC CAACTCTCTA ACCTTGGAAC     660
TGTGAGAACT CTGAGGACAA AGCAGCGGAT ACAACCTCAA AAGACGTCTG TCTACATTGA     720
ATTGGGATCT GATTCTTCTG AAGATACCGT TAATAAGGCA ACTTATTGCA GTGTGGGAGA     780
TCAAGAATTG TTACAAATCA CCCCTCAAGG AACCAGGGAT GAAATCAGTT TGGATTCTGC     840
AAAAAAGGCT GCTTGTGAAT TTTCTGAGAC GGATGTAACA AATACTGAAC ATCATCAACC     900
CAGTAATAAT GATTTGAACA CCACTGAGAA GCGTGCAGCT GAGAGGCATC AGAAAAGTA     960
TCAGGGTAGT TCTGTTTCAA ACTTGCATGT GGAGCCATGT GGCACAAATA CTCATGCCAG    1020
CTCATTACAG CATGAGAACA GCAGTTTATT ACTCACTAAA GACAGAATGA ATGTAGAAAA    1080
GGCTGAATTC TGTAATAAAA GCAAACAGCC TGGCTTAGCA AGGAGCCAAC ATAACAGATG    1140
GGCTGGAAGT AAGGAAACAT GTAATGATAG GCGGACTCCC AGCACAGAAA AAAAGGTAGA    1200
TCTGAATGCT GATCCCCTGT GTGAGAGAAA AGAATGGAAT AAGCAGAAAC TGCCATGCTC    1260
AGAGAATCCT AGAGATACTG AAGATGTTCC TTGGATAACA CTAAATAGCA GCATTCAGAA    1320
AGTTAATGAG TGGTTTTCCA GAAGTGATGA ACTGTTAGGT TCTGATGACT CACATGATGG    1380
GGAGTCTGAA TCAAATGCCA AAGTAGCTGA TGTATTGGAC GTTCTAAATG AGGTAGATGA    1440
ATATTCTGGT TCTTCAGAGA AAATAGACTT ACTGGCCAGT GATCCTCATG AGGCTTTAAT    1500
ATGTAAAAGT GAAAGAGTTC ACTCCAAATC AGTAGAGAGT AATATTGAAG ACAAAATATT    1560
TGGGAAAACC TATCGGAAGA AGGCAAGCCT CCCCAACTTA AGCCATGTAA CTGAAAATCT    1620
AATTATAGGA GCATTTGTTA CTGAGCCACA GATAATACAA GAGCGTCCCC TCACAAATAA    1680
ATTAAAGCGT AAAAGGAGAC CTACATCAGG CCTTCATCCT GAGGATTTTA TCAAGAAAGC    1740
AGATTTGGCA GTTCAAAAGA CTCCTGAAAT GATAAATCAG GGAACTAACC AAACGGAGCA    1800
GAATGGTCAA GTGATGAATA TTACTAATAG TGGTCATGAG AATAAAACAA AAGGTGATTC    1860
TATTCAGAAT GAGAAAAATC CTAACCCAAT AGAATCACTC GAAAAGAAT CTGCTTTCAA    1920
AACGAAAGCT GAACCTATAA GCAGCAGTAT AAGCAATATG GAACTCGAAT TAAATATCCA    1980
CAATTCAAAA GCACCTAAAA AGAATAGGCT GAGGAGGAAG TCTTCTACCA GGCATATTCA    2040
TGCGCTTGAA CTAGTAGTCA GTAGAAATCT AAGCCCACCT AATTGTACTG AATTGCAAAT    2100
TGATAGTTGT TCTAGCAGTG AAGAGATAAA GAAAAAAAAG TACAACCAAA TGCCAGTCAG    2160
GCACAGCAGA AACCTACAAC TCATGGAAGG TAAAGAACCT GCAACTGGAG CCAAGAAGAG    2220
```

-continued

| | |
|---|---|
| TAACAAGCCA AATGAACAGA CAAGTAAAAG ACATGACAGC GATACTTTCC CAGAGCTGAA | 2280 |
| GTTAACAAAT GCACCTGGTT CTTTTACTAA GTGTTCAAAT ACCAGTGAAC TTAAAGAATT | 2340 |
| TGTCAATCCT AGCCTTCCAA GAGAAGAAAA AGAAGAGAAA CTAGAAACAG TTAAAGTGTC | 2400 |
| TAATAATGCT GAAGACCCCA AAGATCTCAT GTTAAGTGGA GAAAGGGTTT TGCAAACTGA | 2460 |
| AAGATCTGTA GAGAGTAGCA GTATTTCATT GGTACCTGGT ACTGATTATG CACTCAGGA | 2520 |
| AAGTATCTCG TTACTGGAAG TTAGCACTCT AGGGAAGGCA AAAACAGAAC CAAATAAATG | 2580 |
| TGTGAGTCAG TGTGCAGCAT TTGAAAACCC CAAGGGACTA ATTCATGGTT GTTCCAAAGA | 2640 |
| TAATAGAAAT GACACAGAAG GCTTTAAGTA TCCATTGGGA CATGAAGTTA ACCACAGTCG | 2700 |
| GGAAACAAGC ATAGAAATGG AAGAAAGTGA ACTTGATGCT CAGTATTTGC AGAATACATT | 2760 |
| CAAGGTTTCA AAGCGCCAGT CATTTGCTCC GTTTTCAAAT CCAGGAAATG CAGAAGAGGA | 2820 |
| ATGTGCAACA TTCTCTGCCC ACTCTGGGTC CTTAAAGAAA CAAAGTCCAA AAGTCACTTT | 2880 |
| TGAATGTGAA CAAAAGGAAG AAAATCAAGG AAAGAATGAG TCTAATATCA AGCCTGTACA | 2940 |
| GACAGTTAAT ATCACTGCAG GCTTTCCTGT GGTTGGTCAG AAAGATAAGC CAGTTGATAA | 3000 |
| TGCCAAATGT AGTATCAAAG GAGGCTCTAG GTTTTGTCTA TCATCTCAGT TCAGAGGCAA | 3060 |
| CGAAACTGGA CTCATTACTC CAAATAAACA TGGACTTTTA CAAAACCCAT ATCGTATACC | 3120 |
| ACCACTTTTT CCCATCAAGT CATTTGTTAA AACTAAATGT AAGAAAAATC TGCTAGAGGA | 3180 |
| AAACTTTGAG GAACATTCAA TGTCACCTGA AAGAGAAATG GGAAATGAGA ACATTCCAAG | 3240 |
| TACAGTGAGC ACAATTAGCC GTAATAACAT TAGAGAAAAT GTTTTTAAAG AAGCCAGCTC | 3300 |
| AAGCAATATT AATGAAGTAG GTTCCAGTAC TAATGAAGTG GGCTCCAGTA TTAATGAAAT | 3360 |
| AGGTTCCAGT GATGAAAACA TTCAAGCAGA ACTAGGTAGA AACAGAGGGC CAAAATTGAA | 3420 |
| TGCTATGCTT AGATTAGGGG TTTTGCAACC TGAGGTCTAT AAACAAAGTC TTCCTGGAAG | 3480 |
| TAATTGTAAG CATCCTGAAA TAAAAAAGCA AGAATATGAA GAAGTAGTTC AGACTGTTAA | 3540 |
| TACAGATTTC TCTCCATATC TGATTTCAGA TAACTTAGAA CAGCCTATGG GAAGTAGTCA | 3600 |
| TGCATCTCAG GTTTGTTCTG AGACACCTGA TGACCTGTTA GATGATGGTG AAATAAAGGA | 3660 |
| AGATACTAGT TTTGCTGAAA ATGACATTAA GGAAAGTTCT GCTGTTTTTA GCAAAAGCGT | 3720 |
| CCAGAAAGGA GAGCTTAGCA GGAGTCCTAG CCCTTTCACC CATACACATT TGGCTCAGGG | 3780 |
| TTACCGAAGA GGGGCCAAGA AATTAGAGTC CTCAGAAGAG AACTTATCTA GTGAGGATGA | 3840 |
| AGAGCTTCCC TGCTTCCAAC ACTTGTTATT TGGTAAAGTA AACAATATAC CTTCTCAGTC | 3900 |
| TACTAGGCAT AGCACCGTTG CTACCGAGTG TCTGTCTAAG AACACAGAGG AGAATTTATT | 3960 |
| ATCATTGAAG AATAGCTTAA ATGACTGCAG TAACCAGGTA ATATTGGCAA AGGCATCTCA | 4020 |
| GGAACATCAC CTTAGTGAGG AAACAAAATG TTCTGCTAGC TTGTTTTCTT CACAGTGCAG | 4080 |
| TGAATTGGAA GACTTGACTG CAAATACAAA CACCCAGGAT CCTTTCTTGA TTGGTTCTTC | 4140 |
| CAAACAAATG AGGCATCAGT CTGAAAGCCA GGGAGTTGGT CTGAGTGACA AGGAATTGGT | 4200 |
| TTCAGATGAT GAAGAAAGAG GAACGGGCTT GGAAGAAAAT AATCAAGAAG AGCAAAGCAT | 4260 |
| GGATTCAAAC TTAGGTGAAG CAGCATCTGG GTGTGAGAGT GAAACAAGCG TCTCTGAAGA | 4320 |
| CTGCTCAGGG CTATCCTCTC AGAGTGACAT TTTAACCACT CAGCAGAGGG ATACCATGCA | 4380 |
| ACATAACCTG ATAAAGCTCC AGCAGGAAAT GGCTGAACTA GAAGCTGTGT TAGAACAGCA | 4440 |
| TGGGAGCCAG CCTTCTAACA GCTACCCTTC CATCATAAGT GACTCTTCTG CCCTTGAGGA | 4500 |
| CCTGCGAAAT CCAGAACAAA GCACATCAGA AAAAGCAGTA TTAACTTCAC AGAAAAGTAG | 4560 |

```
TGAATACCCT ATAAGCCAGA ATCCAGAAGG CCTTTCTGCT GACAAGTTTG AGGTGTCTGC      4620

AGATAGTTCT ACCAGTAAAA ATAAAGAACC AGGAGTGGAA AGGTCATCCC CTTCTAAATG      4680

CCCATCATTA GATGATAGGT GGTACATGCA CAGTTGCTCT GGGAGTCTTC AGAATAGAAA      4740

CTACCCATCT CAAGAGGAGC TCATTAAGGT TGTTGATGTG GAGGAGCAAC AGCTGGAAGA      4800

GTCTGGGCCA CACGATTTGA CGGAAACATC TTACTTGCCA AGGCAAGATC TAGAGGGAAC      4860

CCCTTACCTG GAATCTGGAA TCAGCCTCTT CTCTGATGAC CCTGAATCTG ATCCTTCTGA      4920

AGACAGAGCC CCAGAGTCAG CTCGTGTTGG CAACATACCA TCTTCAACCT CTGCATTGAA      4980

AGTTCCCCAA TTGAAAGTTG CAGAATCTGC CCAGAGTCCA GCTGCTGCTC ATACTACTGA      5040

TACTGCTGGG TATAATGCAA TGGAAGAAAG TGTGAGCAGG GAGAAGCCAG AATTGACAGC      5100

TTCAACAGAA AGGGTCAACA AAGAATGTC CATGGTGGTG TCTGGCCTGA CCCCAGAAGA      5160

ATTTATGCTC GTGTACAAGT TTGCCAGAAA ACACCACATC ACTTTAACTA ATCTAATTAC      5220

TGAAGAGACT ACTCATGTTG TTATGAAAAC AGATGCTGAG TTTGTGTGTG AACGGACACT      5280

GAAATATTTT CTAGGAATTG CGGGAGGAAA ATGGGTAGTT AGCTATTTCT GGGTGACCCA      5340

GTCTATTAAA GAAAGAAAAA TGCTGAATGA GCATGATTTT GAAGTCAGAG GAGATGTGGT      5400

CAATGGAAGA AACCACCAAG GTCCAAAGCG AGCAAGAGAA TCCCAGGACA GAAAGATCTT      5460

CAGGGGGCTA GAAATCTGTT GCTATGGGCC CTTCACCAAC ATGCCCACAG ATCAACTGGA      5520

ATGGATGGTA CAGCTGTGTG GTGCTTCTGT GGTGAAGGAG CTTTCATCAT TCACCCTTGG      5580

CACAGGTGTC CACCCAATTG TGGTTGTGCA GCCAGATGCC TGGACAGAGG ACAATGGCTT      5640

CCATGCAATT GGGCAGATGT GTGAGGCACC TGTGGTGACC CGAGAGTGGG TGTTGGACAG      5700

TGTAGCACTC TACCAGTGCC AGGAGCGGAC ACCTAACCTG ATACCCCAGA TCCCCCACAG      5760

CCACTACTGA                                                            5770

(2) INFORMATION FOR SEQ ID NO: 6:

(i) SEQUENCE CHARACTERISTICS:
        (A) LENGTH: 5710 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 6:

AGCTCGCTGA GACTTCCTGG ACCCCGCACC AGGCTGTGGG GTTTCTCAGA TAACTGGGCC        60

CCTGCGCTCA GGAGGCCTTC ACCCTCTGCT CTGGGTAAAG TTCATTGGAA CAGAAAGAAA       120

TGGATTTATC TGCTCTTCGC GTTGAAGAAG TACAAAATGT CATTAATGCT ATGCAGAAAA       180

TCTTAGAGTG TCCCATCTGT CTGGAGTTGA TCAAGGAACC TGTCTCCACA AAGTGTGACC       240

ACATATTTTG CAAATTTTGC ATGCTGAAAC TTCTCAACCA GAAGAAAGGG CCTTCACAGT       300

GTCCTTTATG TAAGAATGAT ATAACCAAAA GGAGCCTACA AGAAAGTACG AGATTTAGTC       360

AACTTGTTGA AGAGCTATTG AAAATCATTT GTGCTTTTCA GCTTGACACA GGTTTGGAGT       420

ATGCAAACAG CTATAATTTT GCAAAAAAGG AAAATAACTC TCCTGAACAT CTAAAAGATG       480

AAGTTTCTAT CATCCAAAGT ATGGGCTACA GAAACCGTGC CAAAAGACTT CTACAGAGTG       540

AACCCGAAAA TCCTTCCTTG CAGGAAACCA GTCTCAGTGT CCAACTCTCT AACCTTGGAA       600

CTGTGAGAAC TCTGAGGACA AAGCAGCGGA TACAACCTCA AAGACGTCT GTCTACATTG        660

AATTGGGATC TGATTCTTCT GAAGATACCG TTAATAAGGC AACTTATTGC AGTGTGGGAG       720
```

-continued

| | | |
|---|---|---|
| ATCAAGAATT GTTACAAATC ACCCCTCAAG GAACCAGGGA TGAAATCAGT TTGGATTCTG | 780 |
| CAAAAAAGGC TGCTTGTGAA TTTTCTGAGA CGGATGTAAC AAATACTGAA CATCATCAAC | 840 |
| CCAGTAATAA TGATTTGAAC ACCACTGAGA AGCGTGCAGC TGAGAGGCAT CCAGAAAAGT | 900 |
| ATCAGGGTAG TTCTGTTTCA AACTTGCATG TGGAGCCATG TGGCACAAAT ACTCATGCCA | 960 |
| GCTCATTACA GCATGAGAAC AGCAGTTTAT TACTCACTAA AGACAGAATG AATGTAGAAA | 1020 |
| AGGCTGAATT CTGTAATAAA AGCAAACGCC TGGCTTAGCA AGGAGCCAAC ATAACAGATG | 1080 |
| GGCTGGAAGT AAGGAAACAT GTAATGATAG GCGGACTCCC AGCACAGAAA AAAAGGTAGA | 1140 |
| TCTGAATGCT GATCCCCTGT GTGAGAGAAA AGAATGGAAT AAGCAGAAAC TGCCATGCTC | 1200 |
| AGAGAATCCT AGAGATACTG AAGATGTTCC TTGGATAACA CTAAATAGCA GCATTCAGAA | 1260 |
| AGTTAATGAG TGGTTTTCCA GAAGTGATGA ACTGTTAGGT TCTGATGACT CACATGATGG | 1320 |
| GGAGTCTGAA TCAAATGCCA AAGTAGCTGA TGTATTGGAC GTTCTAAATG AGGTAGATGA | 1380 |
| ATATTCTGGT TCTTCAGAGA AAATAGACTT ACTGGCCAGT GATCCTCATG AGGCTTTAAT | 1440 |
| ATGTAAAAGT GAAAGAGTTC ACTCCAAATC AGTAGAGAGT AATATTGAAG ACAAAATATT | 1500 |
| TGGGAAAACC TATCGGAAGA AGGCAAGCCT CCCCAACTTA AGCCATGTAA CTGAAAATCT | 1560 |
| AATTATAGGA GCATTTGTTA CTGAGCCACA GATAATACAA GAGCGTCCCC TCACAAATAA | 1620 |
| ATTAAAGCGT AAAAGGAGAC CTACATCAGG CCTTCATCCT GAGGATTTTA TCAAGAAAGC | 1680 |
| AGATTTGGCA GTTCAAAAGA CTCCTGAAAT GATAAATCAG GGAACTAACC AAACGGAGCA | 1740 |
| GAATGGTCAA GTGATGAATA TTACTAATAG TGGTCATGAG AATAAAACAA AAGGTGATTC | 1800 |
| TATTCAGAAT GAGAAAAATC CTAACCCAAT AGAATCACTC GAAAAAGAAT CTGCTTTCAA | 1860 |
| AACGAAAGCT GAACCTATAA GCAGCAGTAT AAGCAATATG GAACTCGAAT TAAATATCCA | 1920 |
| CAATTCAAAA GCACCTAAAA AGAATAGGCT GAGGAGGAAG TCTTCTACCA GGCATATTCA | 1980 |
| TGCGCTTGAA CTAGTAGTCA GTAGAAATCT AAGCCCACCT AATTGTACTG AATTGCAAAT | 2040 |
| TGATAGTTGT TCTAGCAGTG AAGAGATAAA GAAAAAAAAG TACAACCAAA TGCCAGTCAG | 2100 |
| GCACAGCAGA AACCTACAAC TCATGGAAGG TAAAGAACCT GCAACTGGAG CCAAGAAGAG | 2160 |
| TAACAAGCCA AATGAACAGA CAAGTAAAAG ACATGACAGC GATACTTTCC CAGAGCTGAA | 2220 |
| GTTAACAAAT GCACCTGGTT CTTTTACTAA GTGTTCAAAT ACCAGTGAAC TTAAAGAATT | 2280 |
| TGTCAATCCT AGCCTTCCAA GAGAAGAAAA AGAAGAGAAA CTAGAAACAG TTAAAGTGTC | 2340 |
| TAATAATGCT GAAGACCCCA AAGATCTCAT GTTAAGTGGA GAAAGGGTTT TGCAAACTGA | 2400 |
| AAGATCTGTA GAGAGTAGCA GTATTTCATT GGTACCTGGT ACTGATTATG GCACTCAGGA | 2460 |
| AAGTATCTCG TTACTGGAAG TTAGCACTCT AGGGAAGGCA AAAACAGAAC CAATAAATTG | 2520 |
| TGTGAGTCAG TGTGCAGCAT TTGAAAACCC CAAGGGACTA ATTCATGGTT GTTCCAAAGA | 2580 |
| TAATAGAAAT GACACAGAAG GCTTTAAGTA TCCATTGGGA CATGAAGTTA ACCACAGTCG | 2640 |
| GGAAACAAGC ATAGAAATGG AAGAAAGTGA ACTTGATGCT CAGTATTTGC AGAATACATT | 2700 |
| CAAGGTTTCA AAGCGCCAGT CATTTGCTCC GTTTTCAAAT CCAGGAAATG CAGAAGAGGA | 2760 |
| ATGTGCAACA TTCTCTGCCC ACTCTGGGTC CTTAAAGAAA CAAAGTCCAA AAGTCACTTT | 2820 |
| TGAATGTGAA CAAAAGGAAG AAAATCAAGG AAAGAATGAG TCTAATATCA AGCCTGTACA | 2880 |
| GACAGTTAAT ATCACTGCAG GCTTTCCTGT GGTTGGTCAG AAAGATAAGC CAGTTGATAA | 2940 |
| TGCCAAATGT AGTATCAAAG GAGGCTCTAG GTTTTGTCTA TCATCTCAGT TCAGAGGCAA | 3000 |
| CGAAACTGGA CTCATTACTC CAAATAAACA TGGACTTTTA CAAAACCCAT ATCGTATACC | 3060 |
| ACCACTTTTT CCCATCAAGT CATTTGTTAA AACTAAATGT AAGAAAAATC TGCTAGAGGA | 3120 |

-continued

```
AAACTTTGAG GAACATTCAA TGTCACCTGA AAGAGAAATG GGAAATGAGA ACATTCCAAG    3180

TACAGTGAGC ACAATTAGCC GTAATAACAT TAGAGAAAAT GTTTTTAAAG AAGCCAGCTC    3240

AAGCAATATT AATGAAGTAG GTTCCAGTAC TAATGAAGTG GGCTCCAGTA TTAATGAAAT    3300

AGGTTCCAGT GATGAAAACA TTCAAGCAGA ACTAGGTAGA AACAGAGGGC CAAAATTGAA    3360

TGCTATGCTT AGATTAGGGG TTTTGCAACC TGAGGTCTAT AAACAAAGTC TTCCTGGAAG    3420

TAATTGTAAG CATCCTGAAA TAAAAAAGCA AGAATATGAA GAAGTAGTTC AGACTGTTAA    3480

TACAGATTTC TCTCCATATC TGATTTCAGA TAACTTAGAA CAGCCTATGG GAAGTAGTCA    3540

TGCATCTCAG GTTTGTTCTG AGACACCTGA TGACCTGTTA GATGATGGTG AAATAAAGGA    3600

AGATACTAGT TTTGCTGAAA ATGACATTAA GGAAAGTTCT GCTGTTTTTA GCAAAAGCGT    3660

CCAGAAAGGA GAGCTTAGCA GGAGTCCTAG CCCTTTCACC CATACACATT TGGCTCAGGG    3720

TTACCGAAGA GGGGCCAAGA AATTAGAGTC CTCAGAGAG AACTTATCTA GTGAGGATGA    3780

AGAGCTTCCC TGCTTCCAAC ACTTGTTATT TGGTAAAGTA AACAATATAC CTTCTCAGTC    3840

TACTAGGCAT AGCACCGTTG CTACCGAGTG TCTGTCTAAG AACACAGAGG AGAATTTATT    3900

ATCATTGAAG AATAGCTTAA ATGACTGCAG TAACCAGGTA ATATTGGCAA AGGCATCTCA    3960

GGAACATCAC CTTAGTGAGG AAACAAAATG TTCTGCTAGC TTGTTTTCTT CACAGTGCAG    4020

TGAATTGGAA GACTTGACTG CAAATACAAA CACCCAGGAT CCTTTCTTGA TTGGTTCTTC    4080

CAAACAAATG AGGCATCAGT CTGAAAGCCA GGGAGTTGGT CTGAGTGACA AGGAATTGGT    4140

TTCAGATGAT GAAGAAAGAG GAACGGGCTT GGAAGAAAAT AATCAAGAAG AGCAAAGCAT    4200

GGATTCAAAC TTAGGTGAAG CAGCATCTGG GTGTGAGAGT GAAACAAGCG TCTCTGAAGA    4260

CTGCTCAGGG CTATCCTCTC AGAGTGACAT TTTAACCACT CAGCAGAGGG ATACCATGCA    4320

ACATAACCTG ATAAAGCTCC AGCAGGAAAT GGCTGAACTA GAAGCTGTGT TAGAACAGCA    4380

TGGGAGCCAG CCTTCTAACA GCTACCCTTC CATCATAAGT GACTCTTCTG CCCTTGAGGA    4440

CCTGCGAAAT CCAGAACAAA GCACATCAGA AAAAGCAGTA TTAACTTCAC AGAAAAGTAG    4500

TGAATACCCT ATAAGCCAGA ATCCAGAAGG CCTTTCTGCT GACAAGTTTG AGGTGTCTGC    4560

AGATAGTTCT ACCAGTAAAA ATAAAGAACC AGGAGTGGAA AGGTCATCCC CTTCTAAATG    4620

CCCATCATTA GATGATAGGT GGTACATGCA CAGTTGCTCT GGGAGTCTTC AGAATAGAAA    4680

CTACCCATCT CAAGAGGAGC TCATTAAGGT TGTTGATGTG GAGGAGCAAC AGCTGGAAGA    4740

GTCTGGGCCA CACGATTTGA CGGAAACATC TTACTTGCCA AGGCAAGATC TAGAGGGAAC    4800

CCCTTACCTG GAATCTGGAA TCAGCCTCTT CTCTGATGAC CCTGAATCTG ATCCTTCTGA    4860

AGACAGAGCC CCAGAGTCAG CTCGTGTTGG CAACATACCA TCTTCAACCT CTGCATTGAA    4920

AGTTCCCCAA TTGAAAGTTG CAGAATCTGC CCAGAGTCCA GCTGCTGCTC ATACTACTGA    4980

TACTGCTGGG TATAATGCAA TGGAAGAAAG TGTGAGCAGG GAGAAGCCAG AATTGACAGC    5040

TTCAACAGAA AGGGTCAACA AAAGAATGTC CATGGTGGTG TCTGGCCTGA CCCCAGAAGA    5100

ATTTATGCTC GTGTACAAGT TTGCCAGAAA ACACCACATC ACTTTAACTA ATCTAATTAC    5160

TGAAGAGACT ACTCATGTTG TTATGAAAAC AGATGCTGAG TTTGTGTGTG AACGGACACT    5220

GAAATATTTT CTAGGAATTG CGGGAGGAAA ATGGGTAGTT AGCTATTTCT GGGTGACCCA    5280

GTCTATTAAA GAAAGAAAAA TGCTGAATGA GCATGATTTT GAAGTCAGAG GAGATGTGGT    5340

CAATGGAAGA AACCACCAAG GTCCAAAGCG AGCAAGAGAA TCCAGGACA GAAAGATCTT    5400

CAGGGGGCTA GAAATCTGTT GCTATGGGCC CTTCACCAAC ATGCCCACAG ATCAACTGGA    5460
```

(2) INFORMATION FOR SEQ ID NO: 7:

(i) SEQUENCE CHARACTERISTICS:
        (A) LENGTH: 5709 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 7:

```
ATGGATGGTA CAGCTGTGTG GTGCTTCTGT GGTGAAGGAG CTTTCATCAT TCACCCTTGG     5520
CACAGGTGTC CACCCAATTG TGGTTGTGCA GCCAGATGCC TGGACAGAGG ACAATGGCTT     5580
CCATGCAATT GGGCAGATGT GTGAGGCACC TGTGGTGACC CGAGAGTGGG TGTTGGACAG     5640
TGTAGCACTC TACCAGTGCC AGGAGCTGGA CACCTACCTG ATACCCCAGA TCCCCCACAG     5700
CCACTACTGA                                                            5710
```

```
AGCTCGCTGA GACTTCCTGG ACCCCGCACC AGGCTGTGGG GTTTCTCAGA TAACTGGGCC       60
CCTGCGCTCA GGAGGCCTTC ACCCTCTGCT CTGGGTAAAG TTCATTGGAA CAGAAAGAAA      120
TGGATTTATC TGCTCTTCGC GTTGAAGAAG TACAAAATGT CATTAATGCT ATGCAGAAAA      180
TCTTAGAGTG TCCCATCTGT CTGGAGTTGA TCAAGGAACT TGTCTCCACA AAGTGTGACC      240
ACATATTTTG CAAATTTTGC ATGCTGAAAC TTCTCAACCA GAAGAAAGGG CCTTCACAGT      300
GTCCTTTATG TAAGAATGAT ATAACCAAAA GGAGCCTACA AGAAAGTACG AGATTTAGTC      360
AACTTGTTGA AGAGCTATTG AAAATCATTT GTGCTTTTCA GCTTGACACA GGTTTGGAGT      420
ATGCAAACAG CTATAATTTT GCAAAAAAGG AAAATAACTC TCCTGAACAT CTAAAAGATG      480
AAGTTTCTAT CATCCAAAGT ATGGGCTACA GAAACCGTGC CAAAAGACTT CTACAGAGTG      540
AACCCGAAAA TCCTTCCTTG CAGGAAACCA GTCTCAGTGT CCAACTCTCT AACCTTGGAA      600
CTGTGAGAAC TCTGAGGACA AGCAGCGGA TACAACCTCA AAAGACGTCT GTCTACATTG       660
AATTGGGATC TGATTCTTCT GAAGATACCG TTAATAAGGC AACTTATTGC AGTGTGGGAG      720
ATCAAGAATT GTTACAAATC ACCCCTCAAG GAACCAGGGA TGAAATCAGT TTGGATTCTG      780
CAAAAAAGGC TGCTTGTGAA TTTTCTGAGA CGGATGTAAC AAATACTGAA CATCATCAAC      840
CCAGTAATAA TGATTTGAAC ACCACTGAGA AGCGTGCAGC TGAGAGGCAT CCAGAAAAGT      900
ATCAGGGTAG TTCTGTTTCA AACTTGCATG TGGAGCCATG TGGCACAAAT ACTCATGCCA      960
GCTCATTACA GCATGAGAAC AGCAGTTTAT TACTCACTAA AGACAGAATG AATGTAGAAA     1020
AGGCTGAATT CTGTAATAAA AGCAAACAGC CTGGCTTAGC AAGGAGCCAA CATAACAGAT     1080
GGGCTGGAAG TAAGGAAACA TGTAATGATA GGCGGACTCC CAGCACAGAA AAAAAGGTAG     1140
ATCTGAATGC TGATCCCCTG TGTGAGAGAA AAGAATGGAA TAAGCAGAAA CTGCCATGCT     1200
CAGAGAATCC TAGAGATACT GAAGATGTTC CTTGGATAAC ACTAAATAGC AGCATTCAGA     1260
AAGTTAATGA GTGGTTTTCC AGAAGTGATG AACTGTTAGG TTCTGATGAC TCACATGATG     1320
GGGAGTCTGA ATCAAATGCC AAAGTAGCTG ATGTATTGGA CGTTCTAAAT GAGGTAGATG     1380
AATATTCTGG TTCTTCAGAG AAAATAGACT TACTGGCCAG TGATCCTCAT GAGGCTTTAA     1440
TATGTAAAAG TGAAAGAGTT CACTCCAAAT CAGTAGAGAG TAATATTGAA GACAAAATAT     1500
TTGGGAAAAC CTATCGGAAG AAGGCAAGCC TCCCCAACTT AAGCCATGTA ACTGAAAATC     1560
TAATTATAGG AGCATTTGTT ACTGAGCCAC AGATAATACA AGAGCGTCCC CTCACAAATA     1620
AATTAAAGCG TAAAAGGAGA CCTACATCAG GCCTTCATCC TGAGGATTTT ATCAAGAAAG     1680
```

-continued

```
CAGATTTGGC AGTTCAAAAG ACTCCTGAAA TGATAAATCA GGGAACTAAC CAAACGGAGC    1740

AGAATGGTCA AGTGATGAAT ATTACTAATA GTGGTCATGA GAATAAAACA AAAGGTGATT    1800

CTATTCGAAA TGAGAAAAAT CCTAACCCAA TAGAATCACT CGAAAAAGAA TCTGCTTTCA    1860

AAACGAAAGC TGAACCTATA AGCAGCAGTA TAAGCAATAT GGAACTCGAA TTAAATATCC    1920

ACAATTCAAA AGCACCTAAA AAGAATAGGC TGAGGAGGAA GTCTTCTACC AGGCATATTC    1980

ATGCGCTTGA ACTAGTAGTC AGTAGAAATC TAAGCCCACC TAATTGTACT GAATTGCAAA    2040

TTGATAGTTG TTCTAGCAGT GAAGAGATAA AGAAAAAAAA GTACAACCAA ATGCCAGTCA    2100

GGCACAGCAG AAACCTACAA CTCATGGAAG GTAAAGAACC TGCAACTGGA GCCAAGAAGA    2160

GTAACAAGCC AAATGAACAG ACAAGTAAAA GACATGACAG CGATACTTTC CCAGAGCTGA    2220

AGTTAACAAA TGCACCTGGT TCTTTTACTA AGTGTTCAAA TACCAGTGAA CTTAAAGAAT    2280

TTGTCAATCC TAGCCTTCCA AGAGAAGAAA AAGAAGAGAA ACTAGAAACA GTTAAAGTGT    2340

CTAATAATGC TGAAGACCCC AAAGATCTCA TGTTAAGTGG AGAAAGGGTT TTGCAAACTG    2400

AAAGATCTGT AGAGTAGCAG TATTTCATTG GTACCTGGTA CTGATTATGG CACTCAGGAA    2460

AGTATCTCGT TACTGGAAGT TAGCACTCTA GGGAAGGCAA AAACAGAACC AAATAAATGT    2520

GTGAGTCAGT GTGCAGCATT TGAAAACCCC AAGGGACTAA TTCATGGTTG TTCCAAAGAT    2580

AATAGAAATG ACACAGAAGG CTTTAAGTAT CCATTGGGAC ATGAAGTTAA CCACAGTCGG    2640

GAAACAAGCA TAGAAATGGA AGAAAGTGAA CTTGATGCTC AGTATTTGCA GAATACATTC    2700

AAGGTTTCAA AGCGCCAGTC ATTTGCTCCG TTTTCAAATC CAGGAAATGC AGAAGAGGAA    2760

TGTGCAACAT TCTCTGCCCA CTCTGGGTCC TTAAAGAAAC AAAGTCCAAA AGTCACTTTT    2820

GAATGTGAAC AAAAGGAAGA AAATCAAGGA AAGAATGAGT CTAATATCAA GCCTGTACAG    2880

ACAGTTAATA TCACTGCAGG CTTTCCTGTG GTTGGTCAGA AGATAAGCC AGTTGATAAT    2940

GCCAAATGTA GTATCAAAGG AGGCTCTAGG TTTTGTCTAT CATCTCAGTT CAGAGGCAAC    3000

GAAACTGGAC TCATTACTCC AAATAAACAT GGACTTTTAC AAAACCCATA TCGTATACCA    3060

CCACTTTTTC CCATCAAGTC ATTTGTTAAA ACTAAATGTA AGAAAAATCT GCTAGAGGAA    3120

AACTTTGAGG AACATTCAAT GTCACCTGAA AGAGAAATGG GAAATGAGAA CATTCCAAGT    3180

ACAGTGAGCA CAATTAGCCG TAATAACATT AGAGAAAATG TTTTTAAAGA AGCCAGCTCA    3240

AGCAATATTA ATGAAGTAGG TTCCAGTACT AATGAAGTGG GCTCCAGTAT TAATGAAATA    3300

GGTTCCAGTG ATGAAAACAT TCAAGCAGAA CTAGGTAGAA ACAGAGGGCC AAAATTGAAT    3360

GCTATGCTTA GATTAGGGGT TTTGCAACCT GAGGTCTATA ACAAAGTCT TCCTGGAAGT    3420

AATTGTAAGC ATCCTGAAAT AAAAAAGCAA GAATATGAAG AAGTAGTTCA GACTGTTAAT    3480

ACAGATTTCT CTCCATATCT GATTTCAGAT AACTTAGAAC AGCCTATGGG AAGTAGTCAT    3540

GCATCTCAGG TTTGTTCTGA GACACCTGAT GACCTGTTAG ATGATGGTGA AATAAAGGAA    3600

GATACTAGTT TTGCTGAAAA TGACATTAAG GAAAGTTCTG CTGTTTTTAG CAAAAGCGTC    3660

CAGAAAGGAG AGCTTAGCAG GAGTCCTAGC CCTTTCACCC ATACACATTT GGCTCAGGGT    3720

TACCGAAGAG GGGCCAAGAA ATTAGAGTCC TCAGAAGAGA ACTTATCTAG TGAGGATGAA    3780

GAGCTTCCCT GCTTCCAACA CTTGTTATTT GGTAAAGTAA ACAATATACC TTCTCAGTCT    3840

ACTAGGCATA GCACCGTTGC TACCGAGTGT CTGTCTAAGA ACACAGAGGA GAATTTATTA    3900

TCATTGAAGA ATAGCTTAAA TGACTGCAGT AACCAGGTAA TATTGGCAAA GGCATCTCAG    3960

GAACATCACC TTAGTGAGGA AACAAAATGT TCTGCTAGCT TGTTTTCTTC ACAGTGCAGT    4020

GAATTGGAAG ACTTGACTGC AAATACAAAC ACCCAGGATC CTTTCTTGAT TGGTTCTTCC    4080
```

```
AAACAAATGA GGCATCAGTC TGAAAGCCAG GGAGTTGGTC TGAGTGACAA GGAATTGGTT      4140

TCAGATGATG AAGAAAGAGG AACGGGCTTG AAGAAAATA ATCAAGAAGA GCAAAGCATG       4200

GATTCAAACT TAGGTGAAGC AGCATCTGGG TGTGAGAGTG AAACAAGCGT CTCTGAAGAC      4260

TGCTCAGGGC TATCCTCTCA GAGTGACATT TTAACCACTC AGCAGAGGGA TACCATGCAA      4320

CATAACCTGA TAAAGCTCCA GCAGGAAATG GCTGAACTAG AAGCTGTGTT AGAACAGCAT      4380

GGGAGCCAGC CTTCTAACAG CTACCCTTCC ATCATAAGTG ACTCTTCTGC CCTTGAGGAC      4440

CTGCGAAATC CAGAACAAAG CACATCAGAA AAAGCAGTAT TAACTTCACA GAAAAGTAGT      4500

GAATACCCTA TAAGCCAGAA TCCAGAAGGC CTTTCTGCTG ACAAGTTTGA GGTGTCTGCA      4560

GATAGTTCTA CCAGTAAAAA TAAAGAACCA GGAGTGGAAA GGTCATCCCC TTCTAAATGC      4620

CCATCATTAG ATGATAGGTG GTACATGCAC AGTTGCTCTG GGAGTCTTCA GAATAGAAAC      4680

TACCCATCTC AAGAGGAGCT CATTAAGGTT GTTGATGTGG AGGAGCAACA GCTGGAAGAG      4740

TCTGGGCCAC ACGATTTGAC GGAAACATCT TACTTGCCAA GGCAAGATCT AGAGGGAACC      4800

CCTTACCTGG AATCTGGAAT CAGCCTCTTC TCTGATGACC CTGAATCTGA TCCTTCTGAA      4860

GACAGAGCCC CAGAGTCAGC TCGTGTTGGC AACATACCAT CTTCAACCTC TGCATTGAAA      4920

GTTCCCCAAT TGAAAGTTGC AGAATCTGCC CAGAGTCCAG CTGCTGCTCA TACTACTGAT      4980

ACTGCTGGGT ATAATGCAAT GGAAGAAAGT GTGAGCAGGG AGAAGCCAGA ATTGACAGCT      5040

TCAACAGAAA GGGTCAACAA AGAATGTCCA ATGGTGGTGT CTGGCCTGAC CCAGAAGAA      5100

TTTATGCTCG TGTACAAGTT TGCCAGAAAA CACCACATCA CTTTAACTAA TCTAATTACT      5160

GAAGAGACTA CTCATGTTGT TATGAAAACA GATGCTGAGT TTGTGTGTGA ACGGACACTG      5220

AAATATTTTC TAGGAATTGC GGGAGGAAAA TGGGTAGTTA GCTATTTCTG GGTGACCCAG      5280

TCTATTAAAG AAAGAAAAAT GCTGAATGAG CATGATTTTG AAGTCAGAGG AGATGTGGTC      5340

AATGGAAGAA ACCACCAAGG TCCAAAGCGA GCAAGAGAAT CCCAGGACAG AAAGATCTTC      5400

AGGGGGCTAG AAATCTGTTG CTATGGGCCC TTCACCAACA TGCCCACAGA TCAACTGGAA      5460

TGGATGGTAC AGCTGTGTGG TGCTTCTGTG GTGAAGGAGC TTTCATCATT CACCCTTGGC      5520

ACAGGTGTCC ACCCAATTGT GGTTGTGCAG CCAGATGCCT GGACAGAGGA CAATGGCTTC      5580

CATGCAATTG GGCAGATGTG TGAGGCACCT GTGGTGACCC GAGAGTGGGT GTTGGACAGT      5640

GTAGCACTCT ACCAGTGCCA GGAGCTGGAC ACCTACCTGA TACCCCAGAT CCCCCACAGC      5700

CACTACTGA                                                             5709
```

(2) INFORMATION FOR SEQ ID NO: 8:

(i) SEQUENCE CHARACTERISTICS:
        (A) LENGTH: 5709 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 8:

```
AGCTCGCTGA GACTTCCTGG ACCCCGCACC AGGCTGTGGG GTTTCTCAGA TAACTGGGCC       60

CCTGCGCTCA GGAGGCCTTC ACCCTCTGCT CTGGGTAAAG TTCATTGGAA CAGAAAGAAA      120

TGGATTTATC TGCTCTTCGC GTTGAAGAAG TACAAAATGT CATTAATGCT ATGCAGAAAA      180

TCTTAGAGTG TCCCATCTGT CTGGAGTTGA TCAAGGAACC TGTCTCCACA AAGTGTGACC      240

ACATATTTTG CAAATTTTGC ATGCTGAAAC TTCTCAACCA GAAGAAAGGG CCTTCACAGT      300
```

-continued

```
GTCCTTTATG TAAGAATGAT ATAACCAAAA GGAGCCTACA AGAAAGTACG AGATTTAGTC      360

AACTTGTTGA AGAGCTATTG AAAATCATTT GTGCTTTTCA GCTTGACACA GGTTTGGAGT      420

ATGCAAACAG CTATAATTTT GCAAAAAAGG AAAATAACTC TCCTGAACAT CTAAAAGATG      480

AAGTTTCTAT CATCCAAAGT ATGGGCTACA GAAACCGTGC CAAAGACTT CTACAGAGTG       540

AACCCGAAAA TCCTTCCTTG CAGGAAACCA GTCTCAGTGT CCAACTCTCT AACCTTGGAA      600

CTGTGAGAAC TCTGAGGACA AAGCAGCGGA TACAACCTCA AAAGACGTCT GTCTACATTG      660

AATTGGGATC TGATTCTTCT GAAGATACCG TTAATAAGGC AACTTATTGC AGTGTGGGAG      720

ATCAAGAATT GTTACAAATC ACCCCTCAAG GAACCAGGGA TGAAATCAGT TTGGATTCTG      780

CAAAAAAGGC TGCTTGTGAA TTTTCTGAGA CGGATGTAAC AAATACTGAA CATCATCAAC      840

CCAGTAATAA TGATTTGAAC ACCACTGAGA AGCGTGCAGC TGAGAGGCAT CCAGAAAAGT      900

ATCAGGGTAG TTCTGTTTCA AACTTGCATG TGGAGCCATG TGGCACAAAT ACTCATGCCA      960

GCTCATTACA GCATGAGAAC AGCAGTTTAT TACTCACTAA AGACAGAATG AATGTAGAAA     1020

AGGCTGAATT CTGTAATAAA AGCAAACAGC CTGGCTTAGC AAGGAGCCAA CATAACAGAT     1080

GGGCTGGAAG TAAGGAAACA TGTAATGATA GGCGGACTCC CAGCACAGAA AAAAAGGTAG     1140

ATCTGAATGC TGATCCCCTG TGTGAGAGAA AAGAATGGAA TAAGCAGAAA CTGCCATGCT     1200

CAGAGAATCC TAGAGATACT GAAGATGTTC CTTGGATAAC ACTAAATAGC AGCATTCAGA     1260

AAGTTAATGA GTGGTTTTCC AGAAGTGATG AACTGTTAGG TTCTGATGAC TCACATGATG     1320

GGGAGTCTGA ATCAAATGCC AAAGTAGCTG ATGTATTGGA CGTTCTAAAT GAGGTAGATG     1380

AATATTCTGG TTCTTCAGAG AAAATAGACT TACTGGCCAG TGATCCTCAT GAGGCTTTAA     1440

TATGTAAAAG TGAAAGAGTT CACTCCAAAT CAGTAGAGAG TAATATTGAA GACAAAATAT     1500

TTGGGAAAAC CTATCGGAAG AAGGCAAGCC TCCCCAACTT AAGCCATGTA ACTGAAAATC     1560

TAATTATAGG AGCATTTGTT ACTGAGCCAC AGATAATACA AGAGCGTCCC CTCACAAATA     1620

AATTAAAGCG TAAAAGGAGA CCTACATCAG GCCTTCATCC TGAGGATTTT ATCAAGAAAG     1680

CAGATTTGGC AGTTCAAAAG ACTCCTGAAA TGATAAATCA GGGAACTAAC CAAACGGAGC     1740

AGAATGGTCA AGTGATGAAT ATTACTAATA GTGGTCATGA GAATAAAACA AAAGGTGATT     1800

CTATTCAGAA TGAGAAAAAT CCTAACCCAA TAGAATCACT CGAAAAAGAA TCTGCTTTCA     1860

AAACGAAAGC TGAACCTATA AGCAGCAGTA TAAGCAATAT GGAACTCGAA TTAAATATCC     1920

ACAATTCAAA AGCACCTAAA AAGAATAGGC TGAGGAGGAA GTCTTCTACC AGGCATATTC     1980

ATGCGCTTGA ACTAGTAGTC AGTAGAAATC TAAGCCCACC TAATTGTACT GAATTGCAAA     2040

TTGATAGTTG TTCTAGCAGT GAAGAGATAA AGAAAAAAAA GTACAACCAA ATGCCAGTCA     2100

GGCACAGCAG AAAACCTACA ACTCATGGAAG GTAAAGAACC TGCAACTGGA GCCAAGAAGA     2160

GTAACAAGCC AAATGAACAG ACAAGTAAAA GACATGCAG CGATACTTTC CCAGAGCTGA      2220

AGTTAACAAA TGCACCTGGT TCTTTTACTA AGTGTTCAAA TACCAGTGAA CTTAAAGAAT     2280

TTGTCAATCC TAGCCTTCCA AGAGAAGAAA AAGAAGAGAA ACTAGAAACA GTTAAAGTGT     2340

CTAATAATGC TGAAGACCCC AAAGATCTCA TGTTAAGTGG AGAAAGGGTT TTGCAAACTG     2400

AAAGATCTGT AGAGAGTAGC AGTATTTCAT GGTACCTGG TACTGATTAT GGCACTCAGG      2460

AAAGTATCTC GTTACTGGAA GTTAGCACTC TAGGGAAGGC AAAAACAGAA CCAAATAAAT     2520

GTGTGAGTCA GTGTGCAGCA TTTGAAAACC CCAAGGGACT AATTCATGGT TGTTCCAAAG     2580

ATAATAGAAA TGACACAGAA GGCTTTAAGT ATCCATTGGG ACATGAAGTT AACCACAGTC     2640
```

```
GGGAAACAAG CATAGAAATG GAAGAAAGTG AACTTGATGC TCAGTATTTG CAGAATACAT    2700

TCAAGGTTTC AAAGCGCCAG TCATTTGCTC CGTTTTCAAA TCCAGGAAAT GCAGAAGAGG    2760

AATGTGCAAC ATTCTCTGCC CACTCTGGGT CCTTAAAGAC AAAGTCCAAA AGTCACTTTT    2820

GAATGTGAAC AAAAGGAAGA AAATCAAGGA AGAATGAGT  CTAATATCAA GCCTGTACAG    2880

ACAGTTAATA TCACTGCAGG CTTTCCTGTG GTTGGTCAGA AAGATAAGCC AGTTGATAAT    2940

GCCAAATGTA GTATCAAAGG AGGCTCTAGG TTTTGTCTAT CATCTCAGTT CAGAGGCAAC    3000

GAAACTGGAC TCATTACTCC AAATAAACAT GGACTTTTAC AAAACCCATA TCGTATACCA    3060

CCACTTTTTC CCATCAAGTC ATTTGTTAAA ACTAAATGTA AGAAAATCT  GCTAGAGGAA    3120

AACTTTGAGG AACATTCAAT GTCACCTGAA AGAGAAATGG GAAATGAGAA CATTCCAAGT    3180

ACAGTGAGCA CAATTAGCCG TAATAACATT AGAGAAAATG TTTTTAAAGA AGCCAGCTCA    3240

AGCAATATTA ATGAAGTAGG TTCCAGTACT AATGAAGTGG GCTCCAGTAT TAATGAAATA    3300

GGTTCCAGTG ATGAAAACAT TCAAGCAGAA CTAGGTAGAA ACAGAGGGCC AAAATTGAAT    3360

GCTATGCTTA GATTAGGGGT TTTGCAACCT GAGGTCTATA AACAAAGTCT TCCTGGAAGT    3420

AATTGTAAGC ATCCTGAAAT AAAAAAGCAA GAATATGAAG AAGTAGTTCA GACTGTTAAT    3480

ACAGATTTCT CTCCATATCT GATTTCAGAT AACTTAGAAC AGCCTATGGG AAGTAGTCAT    3540

GCATCTCAGG TTTGTTCTGA GACACCTGAT GACCTGTTAG ATGATGGTGA AATAAAGGAA    3600

GATACTAGTT TTGCTGAAAA TGACATTAAG GAAAGTTCTG CTGTTTTTAG CAAAAGCGTC    3660

CAGAAAGGAG AGCTTAGCAG GAGTCCTAGC CCTTTCACCC ATACACATTT GGCTCAGGGT    3720

TACCGAAGAG GGGCCAAGAA ATTAGAGTCC TCAGAAGAGA ACTTATCTAG TGAGGATGAA    3780

GAGCTTCCCT GCTTCCAACA CTTGTTATTT GGTAAAGTAA ACAATATACC TTCTCAGTCT    3840

ACTAGGCATA GCACCGTTGC TACCGAGTGT CTGTCTAAGA ACACAGAGGA GAATTTATTA    3900

TCATTGAAGA ATAGCTTAAA TGACTGCAGT AACCAGGTAA TATTGGCAAA GGCATCTCAG    3960

GAACATCACC TTAGTGAGGA AACAAAATGT TCTGCTAGCT TGTTTTCTTC ACAGTGCAGT    4020

GAATTGGAAG ACTTGACTGC AAATACAAAC ACCCAGGATC CTTTCTTGAT TGGTTCTTCC    4080

AAACAAATGA GGCATCAGTC TGAAAGCCAG GGAGTTGGTC TGAGTGACAA GGAATTGGTT    4140

TCAGATGATG AAGAAAGAGG AACGGGCTTG GAAGAAAATA ATCAAGAAGA GCAAAGCATG    4200

GATTCAAACT TAGGTGAAGC AGCATCTGGG TGTGAGAGTG AAACAAGCGT CTCTGAAGAC    4260

TGCTCAGGGC TATCCTCTCA GAGTGACATT TTAACCACTC AGCAGAGGGA TACCATGCAA    4320

CATAACCTGA TAAAGCTCCA GCAGGAAATG GCTGAACTAG AAGCTGTGTT AGAACAGCAT    4380

GGGAGCCAGC CTTCTAACAG CTACCCTTCC ATCATAAGTG ACTCTTCTGC CCTTGAGGAC    4440

CTGCGAAATC CAGAACAAAG CACATCAGAA AAAGCAGTAT TAACTTCACA GAAAAGTAGT    4500

GAATACCCTA TAAGCCAGAA TCCAGAAGGC CTTTCTGCTG ACAAGTTTGA GGTGTCTGCA    4560

GATAGTTCTA CCAGTAAAAA TAAAGAACCA GGAGTGGAAA GGTCATCCCC TTCTAAATGC    4620

CCATCATTAG ATGATAGGTG GTACATGCAC AGTTGCTCTG GGAGTCTTCA GAATAGAAAC    4680

TACCCATCTC AAGAGGAGCT CATTAAGGTT GTTGATGTGG AGGAGCAACA GCTGGAAGAG    4740

TCTGGGCCAC ACGATTTGAC GGAAACATCT TACTTGCCAA GGCAAGATCT AGAGGGAACC    4800

CCTTACCTGG AATCTGGAAT CAGCCTCTTC TCTGATGACC CTGAATCTGA TCCTTCTGAA    4860

GACAGAGCCC CAGAGTCAGC TCGTGTTGGC AACATACCAT CTTCAACCTC TGCATTGAAA    4920

GTTCCCCAAT TGAAAGTTGC AGAATCTGCC CAGAGTCCAG CTGCTGCTCA TACTACTGAT    4980

ACTGCTGGGT ATAATGCAAT GGAAGAAAGT GTGAGCAGGG AGAAGCCAGA ATTGACAGCT    5040
```

-continued

```
TCAACAGAAA GGGTCAACAA AAGAATGTCC ATGGTGGTGT CTGGCCTGAC CCCAGAAGAA    5100

TTTATGCTCG TGTACAAGTT TGCCAGAAAA CACCACATCA CTTTAACTAA TCTAATTACT    5160

GAAGAGACTA CTCATGTTGT TATGAAAACA GATGCTGAGT TTGTGTGTGA ACGGACACTG    5220

AAATATTTTC TAGGAATTGC GGGAGGAAAA TGGGTAGTTA GCTATTTCTG GGTGACCCAG    5280

TCTATTAAAG AAAGAAAAAT GCTGAATGAG CATGATTTTG AAGTCAGAGG AGATGTGGTC    5340

AATGGAAGAA ACCACCAAGG TCCAAAGCGA GCAAGAGAAT CCCAGGACAG AAAGATCTTC    5400

AGGGGGCTAG AAATCTGTTG CTATGGGCCC TTCACCAACA TGCCCACAGA TCAACTGGAA    5460

TGGATGGTAC AGCTGTGTGG TGCTTCTGTG GTGAAGGAGC TTTCATCATT CACCCTTGGC    5520

ACAGGTGTCC ACCCAATTGT GGTTGTGCAG CCAGATGCCT GGACAGAGGA CAATGGCTTC    5580

CATGCAATTG GCAGATGTGT TGAGGCACCT GTGGTGACCC GAGAGTGGGT GTTGGACAGT    5640

GTAGCACTCT ACCAGTGCCA GGAGCTGGAC ACCTACCTGA TACCCCAGAT CCCCCACAGC    5700

CACTACTGA                                                            5709
```

(2) INFORMATION FOR SEQ ID NO: 9:

(i) SEQUENCE CHARACTERISTICS:
        (A) LENGTH: 5709 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 9:

```
AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAA     120

TGGATTTATC TGCTCTTCGC GTTGAAGAAG TACAAAATGT CATTAATGCT ATGCAGAAAA     180

TCTTAGAGTG TCCCATCTGT CTGGAGTTGA TCAAGGAACC TGTCTCCACA AAGTGTGACC     240

ACATATTTTG CAAATTTTGC ATGCTGAAAC TTCTCAACCA GAAGAAAGGG CCTTCACAGT     300

GTCCTTTATG TAAGAATGAT ATAACCAAAA GGAGCCTACA AGAAAGTACG AGATTTAGTC     360

AACTTGTTGA AGAGCTATTG AAAATCATTT GTGCTTTTCA GCTTGACACA GGTTTGGAGT     420

ATGCAAACAG CTATAATTTT GCAAAAAAGG AAAATAACTC TCCTGAACAT CTAAAAGATG     480

AAGTTTCTAT CATCCAAAGT ATGGGCTACA GAAACCGTGC CAAAAGACTT CTACAGAGTG     540

AACCCGAAAA TCCTTCCTTG CAGGAAACCA GTCTCAGTGT CCAACTCTCT AACCTTGGAA     600

CTGTGAGAAC TCTGAGGACA AAGCAGCGGA TACAACCTCA AAAGACGTCT GTCTACATTG     660

AATTGGGATC TGATTCTTCT GAAGATACCG TTAATAAGGC AACTTATTGC AGTGTGGGAG     720

ATCAAGAATT GTTACAAATC ACCCCTCAAG GAACCAGGGA TGAAATCAGT TTGGATTCTG     780

CAAAAAAGGC TGCTTGTGAA TTTTCTGAGA CGGATGTAAC AAATACTGAA CATCATCAAC     840

CCAGTAATAA TGATTTGAAC ACCACTGAGA AGCGTGCAGC TGAGAGGCAT CCAGAAAAGT     900

ATCAGGGTAG TTCTGTTTCA AACTTGCATG TGGAGCCATG TGGCACAAAT ACTCATGCCA     960

GCTCATTACA GCATGAGAAC AGCAGTTTAT TACTCACTAA AGACAGAATG AATGTAGAAA    1020

AGGCTGAATT CTGTAATAAA AGCAAACAGC CTGGCTTAGC AAGGAGCCAA CATAACAGAT    1080

GGGCTGGAAG TAAGGAAACA TGTAATGATA GGCGGACTCC CAGCACAGAA AAAAAGGTAG    1140

ATCTGAATGC TGATCCCCTG TGTGAGAGAA AGAATGGAA TAAGCAGAAA CTGCCATGCT    1200

CAGAGAATCC TAGAGATACT GAAGATGTTC CTTGGATAAC ACTAAATAGC AGCATTCAGA    1260
```

-continued

```
AAGTTAATGA GTGGTTTTCC AGAAGTGATG AACTGTTAGG TTCTGATGAC TCACATGATG    1320

GGGAGTCTGA ATCAAATGCC AAAGTAGCTG ATGTATTGGA CGTTCTAAAT GAGGTAGATG    1380

AATATTCTGG TTCTTCAGAG AAAATAGACT TACTGGCCAG TGATCCTCAT GAGGCTTTAA    1440

TATGTAAAAG TGAAAGAGTT CACTCCAAAT CAGTAGAGAG TAATATTGAA GACAAAATAT    1500

TTGGGAAAAC CTATCGGAAG AAGGCAAGCC TCCCCAACTT AAGCCATGTA ACTGAAAATC    1560

TAATTATAGG AGCATTTGTT ACTGAGCCAC AGATAATACA AGAGCGTCCC CTCACAAATA    1620

AATTAAAGCG TAAAAGGAGA CCTACATCAG GCCTTCATCC TGAGGATTTT ATCAAGAAAG    1680

CAGATTTGGC AGTTCAAAAG ACTCCTGAAA TGATAAATCA GGGAACTAAC CAAACGGAGC    1740

AGAATGGTCA AGTGATGAAT ATTACTAATA GTGGTCATGA GAATAAAACA AAAGGTGATT    1800

CTATTCAGAA TGAGAAAAAT CCTAACCCAA TAGAATCACT CGAAAAGAA TCTGCTTTCA     1860

AAACGAAAGC TGAACCTATA AGCAGCAGTA TAAGCAATAT GGAACTCGAA TTAAATATCC    1920

ACAATTCAAA AGCACCTAAA AAGAATAGGC TGAGGAGGAA GTCTTCTACC AGGCATATTC    1980

ATGCGCTTGA ACTAGTAGTC AGTAGAAATC TAAGCCCACC TAATTGTACT GAATTGCAAA    2040

TTGATAGTTG TTCTAGCAGT GAAGAGATAA AGAAAAAAAA GTACAACCAA ATGCCAGTCA    2100

GGCACAGCAG AAACCTACAA CTCATGGAAG GTAAAGAACC TGCAACTGGA GCCAAGAAGA    2160

GTAACAAGCC AAATGAACAG ACAAGTAAAA GACATGACAG CGATACTTTC CCAGAGCTGA    2220

AGTTAACAAA TGCACCTGGT TCTTTTACTA AGTGTTCAAA TACCAGTGAA CTTAAAGAAT    2280

TTGTCAATCC TAGCCTTCCA AGAGAAGAAA AAGAAGAGAA ACTAGAAACA GTTAAAGTGT    2340

CTAATAATGC TGAAGACCCC AAAGATCTCA TGTTAAGTGG AGAAAGGGTT TTGCAAACTG    2400

AAAGATCTGT AGAGAGTAGC AGTATTTCAT TGGTACCTGG TACTGATTAT GGCACTCAGG    2460

AAAGTATCTC GTTACTGGAA GTTAGCACTC TAGGGAAGGC AAAAACAGAA CCAAATAAAT    2520

GTGTGAGTCA GTGTGCAGCA TTTGAAAACC CCAAGGGACT AATTCATGGT TGTTCCAAAG    2580

ATAATAGAAA TGCACAGAA GGCTTTAAGT ATCCATTGGG ACATGAAGTT AACCACAGTC     2640

GGGAAACAAG CATAGAAATG GAAGAAAGTG AACTTGATGC TCAGTATTTG CAGAATACAT    2700

TCAAGGTTTC AAAGCGCCAG TCATTTGCTC CGTTTTCAAA TCCAGGAAAT GCAGAAGAGG    2760

AATGTGCAAC ATTCTCTGCC CACTCTGGGT CCTTAAAGAA ACAAAGTCCA AAAGTCACTT    2820

TTGAATGTGA ACAAAAGGAA GAAAATCAAG GAAAGAATGA GTAATATCAA GCCTGTACAG    2880

ACAGTTAATA TCACTGCAGG CTTTCCTGTG GTTGGTCAGA AGATAAGCC AGTTGATAAT     2940

GCCAAATGTA GTATCAAAGG AGGCTCTAGG TTTTGTCTAT CATCTCAGTT CAGAGGCAAC    3000

GAAACTGGAC TCATTACTCC AAATAAACAT GGACTTTTAC AAAACCCATA TCGTATACCA    3060

CCACTTTTTC CCATCAAGTC ATTTGTTAAA ACTAAATGTA AGAAAAATCT GCTAGAGGAA    3120

AACTTTGAGG AACATTCAAT GTCACCTGAA AGAGAAATGG AAATGAGAA CATTCCAAGT     3180

ACAGTGAGCA CAATTAGCCG TAATAACATT AGAGAAAATG TTTTTAAAGA AGCCAGCTCA    3240

AGCAATATTA ATGAAGTAGG TTCCAGTACT AATGAAGTGG GCTCCAGTAT TAATGAAATA    3300

GGTTCCAGTG ATGAAAACAT TCAAGCAGAA CTAGGTAGAA ACAGAGGGCC AAAATTGAAT    3360

GCTATGCTTA GATTAGGGGT TTTGCAACCT GAGGTCTATA AACAAAGTCT TCCTGGAAGT    3420

AATTGTAAGC ATCCTGAAAT AAAAAGCAA GAATATGAAG AAGTAGTTCA GACTGTTAAT     3480

ACAGATTTCT CTCCATATCT GATTTCAGAT AACTTAGAAC AGCCTATGGG AAGTAGTCAT    3540

GCATCTCAGG TTTGTTCTGA GACACCTGAT GACCTGTTAG ATGATGGTGA AATAAAGGAA    3600
```

-continued

```
GATACTAGTT TTGCTGAAAA TGACATTAAG GAAAGTTCTG CTGTTTTTAG CAAAAGCGTC    3660

CAGAAAGGAG AGCTTAGCAG GAGTCCTAGC CCTTTCACCC ATACACATTT GGCTCAGGGT    3720

TACCGAAGAG GGGCCAAGAA ATTAGAGTCC TCAGAAGAGA ACTTATCTAG TGAGGATGAA    3780

GAGCTTCCCT GCTTCCAACA CTTGTTATTT GGTAAAGTAA ACAATATACC TTCTCAGTCT    3840

ACTAGGCATA GCACCGTTGC TACCGAGTGT CTGTCTAAGA ACACAGAGGA GAATTTATTA    3900

TCATTGAAGA ATAGCTTAAA TGACTGCAGT AACCAGGTAA TATTGGCAAA GGCATCTCAG    3960

GAACATCACC TTAGTGAGGA AACAAAATGT TCTGCTAGCT TGTTTTCTTC ACAGTGCAGT    4020

GAATTGGAAG ACTTGACTGC AAATACAAAC ACCCAGGATC CTTTCTTGAT TGGTTCTTCC    4080

AAACAAATGA GGCATCAGTC TGAAAGCCAG GGAGTTGGTC TGAGTGACAA GGAATTGGTT    4140

TCAGATGATG AAGAAGAGG AACGGGCTTG GAAGAAAATA ATCAAGAAGA GCAAAGCATG    4200

GATTCAAACT TAGGTGAAGC AGCATCTGGG TGTGAGAGTG AAACAAGCGT CTCTGAAGAC    4260

TGCTCAGGGC TATCCTCTCA GAGTGACATT TTAACCACTC AGCAGAGGGA TACCATGCAA    4320

CATAACCTGA TAAAGCTCCA GCAGGAAATG GCTGAACTAG AAGCTGTGTT AGAACAGCAT    4380

GGGAGCCAGC CTTCTAACAG CTACCCTTCC ATCATAAGTG ACTCTTCTGC CCTTGAGGAC    4440

CTGCGAAATC CAGAACAAAG CACATCAGAA AAAGCAGTAT TAACTTCACA GAAAAGTAGT    4500

GAATACCCTA TAAGCCAGAA TCCAGAAGGC CTTTCTGCTG ACAAGTTTGA GGTGTCTGCA    4560

GATAGTTCTA CCAGTAAAAA TAAAGAACCA GGAGTGGAAA GGTCATCCCC TTCTAAATGC    4620

CCATCATTAG ATGATAGGTG GTACATGCAC AGTTGCTCTG GGAGTCTTCA GAATAGAAAC    4680

TACCCATCTC AAGAGGAGCT CATTAAGGTT GTTGATGTGG AGGAGCAACA GCTGGAAGAG    4740

TCTGGGCCAC ACGATTTGAC GGAAACATCT TACTTGCCAA GGCAAGATCT AGAGGGAACC    4800

CCTTACCTGG AATCTGGAAT CAGCCTCTTC TCTGATGACC CTGAATCTGA TCCTTCTGAA    4860

GACAGAGCCC CAGAGTCAGC TCGTGTTGGC AACATACCAT CTTCAACCTC TGCATTGAAA    4920

GTTCCCCAAT TGAAAGTTGC AGAATCTGCC CAGAGTCCAG CTGCTGCTCA TACTACTGAT    4980

ACTGCTGGGT ATAATGCAAT GGAAGAAAGT GTGAGCAGGG AGAAGCCAGA ATTGACAGCT    5040

TCAACAGAAA GGGTCAACAA AGAATGTCC ATGGTGGTGT CTGGCCTGAC CCCAGAAGAA    5100

TTTATGCTCG TGTACAAGTT TGCCAGAAAA CACCACATCA CTTTAACTAA TCTAATTACT    5160

GAAGAGACTA CTCATGTTGT TATGAAAACA GATGCTGAGT TTGTGTGTGA ACGGACACTG    5220

AAATATTTTC TAGGAATTGC GGGAGGAAAA TGGGTAGTTA GCTATTTCTG GGTGACCCAG    5280

TCTATTAAAG AAAGAAAAAT GCTGAATGAG CATGATTTTG AAGTCAGAGG AGATGTGGTC    5340

AATGGAAGAA ACCACCAAGG TCCAAAGCGA GCAAGAGAAT CCCAGGACAG AAAGATCTTC    5400

AGGGGGCTAG AAATCTGTTG CTATGGGCCC TTCACCAACA TGCCCACAGA TCAACTGGAA    5460

TGGATGGTAC AGCTGTGTGG TGCTTCTGTG GTGAAGGAGC TTTCATCATT CACCCTTGGC    5520

ACAGGTGTCC ACCCAATTGT GGTTGTGCAG CCAGATGCCT GGACAGAGGA CAATGGCTTC    5580

CATGCAATTG GGCAGATGTG TGAGGCACCT GTGGTGACCC GAGAGTGGGT GTTGGACAGT    5640

GTAGCACTCT ACCAGTGCCA GGAGCTGGAC ACCTACCTGA TACCCCAGAT CCCCCACAGC    5700

CACTACTGA                                                            5709
```

(2) INFORMATION FOR SEQ ID NO: 10:

(i) SEQUENCE CHARACTERISTICS:
        (A) LENGTH: 5711 base pairs
        (B) TYPE: nucleic acid
        (C) STRANDEDNESS: double (D) TOPOLOGY: linear (ii) MOLECULE TYPE: cDNA (xi) SEQUENCE DESCRIPTION: SEQ ID NO: 10:

```
AGCTCGCTGA GACTTCCTGG ACCCCGCACC AGGCTGTGGG GTTTCTCAGA TAACTGGGCC      60
CCTGCGCTCA GGAGGCCTTC ACCCTCTGCT CTGGGTAAAG TTCATTGGAA CAGAAAGAAA     120
TGGATTTATC TGCTCTTCGC GTTGAAGAAG TACAAAATGT CATTAATGCT ATGCAGAAAA     180
TCTTAGAGTG TCCCATCTGT CTGGAGTTGA TCAAGGAACC TGTCTCCACA AAGTGTGACC     240
ACATATTTTG CAAATTTTGC ATGCTGAAAC TTCTCAACCA GAAGAAAGGG CCTTCACAGT     300
GTCCTTTATG TAAGAATGAT ATAACCAAAA GGAGCCTACA AGAAAGTACG AGATTTAGTC     360
AACTTGTTGA AGAGCTATTG AAAATCATTT GTGCTTTTCA GCTTGACACA GGTTTGGAGT     420
ATGCAAACAG CTATAATTTT GCAAAAAAGG AAAATAACTC TCCTGAACAT CTAAAAGATG     480
AAGTTTCTAT CATCCAAAGT ATGGGCTACA GAAACCGTGC CAAAAGACTT CTACAGAGTG     540
AACCCGAAAA TCCTTCCTTG CAGGAAACCA GTCTCAGTGT CCAACTCTCT AACCTTGGAA     600
CTGTGAGAAC TCTGAGGACA AGCAGCGGA TACAACCTCA AAAGACGTCT GTCTACATTG      660
AATTGGGATC TGATTCTTCT GAAGATACCG TTAATAAGGC AACTTATTGC AGTGTGGGAG     720
ATCAAGAATT GTTACAAATC ACCCCTCAAG GAACCAGGGA TGAAATCAGT TTGGATTCTG     780
CAAAAAAGGC TGCTTGTGAA TTTTCTGAGA CGGATGTAAC AAATACTGAA CATCATCAAC     840
CCAGTAATAA TGATTTGAAC ACCACTGAGA AGCGTGCAGC TGAGAGGCAT CCAGAAAAGT     900
ATCAGGGTAG TTCTGTTTCA AACTTGCATG TGGAGCCATG TGGCACAAAT ACTCATGCCA     960
GCTCATTACA GCATGAGAAC AGCAGTTTAT TACTCACTAA AGACAGAATG AATGTAGAAA    1020
AGGCTGAATT CTGTAATAAA AGCAAACAGC CTGGCTTAGC AAGGAGCCAA CATAACAGAT    1080
GGGCTGGAAG TAAGGAAACA TGTAATGATA GGCGGACTCC CAGCACAGAA AAAAAGGTAG    1140
ATCTGAATGC TGATCCCCTG TGTGAGAGAA AGAATGGAA TAAGCAGAAA CTGCCATGCT     1200
CAGAGAATCC TAGAGATACT GAAGATGTTC CTTGGATAAC ACTAAATAGC AGCATTCAGA    1260
AAGTTAATGA GTGGTTTTCC AGAAGTGATG AACTGTTAGG TTCTGATGAC TCACATGATG    1320
GGGAGTCTGA ATCAAATGCC AAAGTAGCTG ATGTATTGGA CGTTCTAAAT GAGGTAGATG    1380
AATATTCTGG TTCTTCAGAG AAAATAGACT TACTGGCCAG TGATCCTCAT GAGGCTTTAA    1440
TATGTAAAAG TGAAAGAGTT CACTCCAAAT CAGTAGAGAG TAATATTGAA GACAAAATAT    1500
TTGGGAAAAC CTATCGGAAG AAGGCAAGCC TCCCCAACTT AAGCCATGTA ACTGAAAATC    1560
TAATTATAGG AGCATTTGTT ACTGAGCCAC AGATAATACA AGAGCGTCCC CTCACAAATA    1620
AATTAAAGCG TAAAAGGAGA CCTACATCAG GCCTTCATCC TGAGGATTTT ATCAAGAAAG    1680
CAGATTTGGC AGTTCAAAAG ACTCCTGAAA TGATAAATCA GGGAACTAAC CAAACGGAGC    1740
AGAATGGTCA AGTGATGAAT ATTACTAATA GTGGTCATGA GAATAAAACA AAAGGTGATT    1800
CTATTCAGAA TGAAAAAAAT CCTAACCCAA TAGAATCACT CGAAAAGAA TCTGCTTTCA     1860
AAACGAAAGC TGAACCTATA AGCAGCAGTA TAAGCAATAT GGAACTCGAA TTAAATATCC    1920
ACAATTCAAA AGCACCTAAA AAGAATAGGC TGAGGAGGAA GTCTTCTACC AGGCATATTC    1980
ATGCGCTTGA ACTAGTAGTC AGTAGAAATC TAAGCCCACC TAATTGTACT GAATTGCAAA    2040
TTGATAGTTG TTCTAGCAGT GAAGAGATAA AGAAAAAAAA GTACAACCAA ATGCCAGTCA    2100
GGCACAGCAG AAAACCTACA ACTCATGGAA GTAAAGAACC TGCAACTGGA GCCAAGAAGA    2160
GTAACAAGCC AAATGAACAG ACAAGTAAAA GACATGACAG CGATACTTTC CCAGAGCTGA    2220
```

```
AGTTAACAAA TGCACCTGGT TCTTTTACTA AGTGTTCAAA TACCAGTGAA CTTAAAGAAT    2280

TTGTCAATCC TAGCCTTCCA AGAGAAGAAA AAGAAGAGAA ACTAGAAACA GTTAAAGTGT    2340

CTAATAATGC TGAAGACCCC AAAGATCTCA TGTTAAGTGG AGAAAGGGTT TTGCAAACTG    2400

AAAGATCTGT AGAGAGTAGC AGTATTTCAT TGGTACCTGG TACTGATTAT GGCACTCAGG    2460

AAAGTATCTC GTTACTGGAA GTTAGCACTC TAGGGAAGGC AAAAACAGAA CCAAATAAAT    2520

GTGTGAGTCA GTGTGCAGCA TTTGAAAACC CCAAGGGACT AATTCATGGT TGTTCCAAAG    2580

ATAATAGAAA TGACACAGAA GGCTTTAAGT ATCCATTGGG ACATGAAGTT AACCACAGTC    2640

GGGAAACAAG CATAGAAATG GAAGAAAGTG AACTTGATGC TCAGTATTTG CAGAATACAT    2700

TCAAGGTTTC AAAGCGCCAG TCATTTGCTC CGTTTTCAAA TCCAGGAAAT GCAGAAGAGG    2760

AATGTGCAAC ATTCTCTGCC CACTCTGGGT CCTTAAAGAA ACAAAGTCCA AAAGTCACTT    2820

TTGAATGTGA ACAAAAGGAA GAAAATCAAG GAAAGAATGA GTCTAATATC AAGCCTGTAC    2880

AGACAGTTAA TATCACTGCA GGCTTTCCTG TGGTTGGTCA GAAAGATAAG CCAGTTGATA    2940

ATGCCAAATG TAGTATCAAA GGAGGCTCTA GGTTTTGTCT ATCATCTCAG TTCAGAGGCA    3000

ACGAAACTGG ACTCATTACT CCAAATAAAC ATGGACTTTT ACAAAACCCA TATCGTATAC    3060

CACCACTTTT TCCCATCAAG TCATTTGTTA AAACTAAATG TAAGAAAAAT CTGCTAGAGG    3120

AAAACTTTGA GGAACATTCA ATGTCACCTG AAAGAGAAAT GGGAAATGAG AACATTCCAA    3180

GTACAGTGAG CACAATTAGC CGTAATAACA TTAGAGAAAA TGTTTTTAAA GAAGCCAGCT    3240

CAAGCAATAT TAATGAAGTA GGTTCCAGTA CTAATGAAGT GGGCTCCAGT ATTAATGAAA    3300

TAGGTTCCAG TGATGAAAAC ATTCAAGCAG AACTAGGTAG AAACAGAGGG CCAAAATTGA    3360

ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480

ATACAGATTT CTCTCCATAT CTGATTTCAG ATAACTTAGA ACAGCCTATG GGAAGTAGTC    3540

ATGCATCTCA GGTTTGTTCT GAGACACCTG ATGACCTGTT AGATGATGGT GAAATAAAGG    3600

AAGATACTAG TTTTGCTGAA AATGACATTA AGGAAAGTTC TGCTGTTTTT AGCAAAAGCG    3660

TCCAGAAAGG AGAGCTTAGC AGGAGTCCTA GCCCTTTCAC CCATACACAT TTGGCTCAGG    3720

GTTACTGAAG AGGGGCCAAG AAATTAGAGT CCTCAGAAGA GAACTTATCT AGTGAGGATG    3780

AAGAGCTTCC CTGCTTCCAA CACTTGTTAT TTGGTAAAGT AAACAATATA CCTTCTCAGT    3840

CTACTAGGCA TAGCACCGTT GCTACCGAGT GTCTGTCTAA GAACACAGAG GAGAATTTAT    3900

TATCATTGAA GAATAGCTTA AATGACTGCA GTAACCAGGT AATATTGGCA AAGGCATCTC    3960

AGGAACATCA CCTTAGTGAG GAAACAAAAT GTTCTGCTAG CTTGTTTTCT TCACAGTGCA    4020

GTGAATTGGA AGACTTGACT GCAAATACAA ACACCCAGGA TCCTTTCTTG ATTGGTTCTT    4080

CCAAACAAAT GAGGCATCAG TCTGAAAGCC AGGGAGTTGG TCTGAGTGAC AAGGAATTGG    4140

TTTCAGATGA TGAAGAAAGA GGAACGGGCT TGGAAGAAAA TAATCAAGAA GAGCAAAGCA    4200

TGGATTCAAA CTTAGGTGAA GCAGCATCTG GGTGTGAGAG TGAAACAAGC GTCTCTGAAG    4260

ACTGCTCAGG GCTATCCTCT CAGAGTGACA TTTTAACCAC TCAGCAGAGG GATACCATGC    4320

AACATAACCT GATAAAGCTC CAGCAGGAAA TGGCTGAACT AGAAGCTGTG TTAGAACAGC    4380

ATGGGAGCCA GCCTTCTAAC AGCTACCCTT CCATCATAAG TGACTCTTCT GCCCTTGAGG    4440

ACCTGCGAAA TCCAGAACAA AGCACATCAG AAAAAGCAGT ATTAACTTCA CAGAAAAGTA    4500

GTGAATACCC TATAAGCCAG AATCCAGAAG GCCTTTCTGC TGACAAGTTT GAGGTGTCTG    4560
```

```
CAGATAGTTC TACCAGTAAA AATAAAGAAC CAGGAGTGGA AAGGTCATCC CCTTCTAAAT      4620

GCCCATCATT AGATGATAGG TGGTACATGC ACAGTTGCTC TGGGAGTCTT CAGAATAGAA      4680

ACTACCCATC TCAAGAGGAG CTCATTAAGG TTGTTGATGT GGAGGAGCAA CAGCTGGAAG      4740

AGTCTGGGCC ACACGATTTG ACGGAAACAT CTTACTTGCC AAGGCAAGAT CTAGAGGGAA      4800

CCCCTTACCT GGAATCTGGA ATCAGCCTCT TCTCTGATGA CCCTGAATCT GATCCTTCTG      4860

AAGACAGAGC CCCAGAGTCA GCTCGTGTTG CAACATACC ATCTTCAACC TCTGCATTGA       4920

AAGTTCCCCA ATTGAAAGTT GCAGAATCTG CCCAGAGTCC AGCTGCTGCT CATACTACTG      4980

ATACTGCTGG GTATAATGCA ATGGAAGAAA GTGTGAGCAG GGAGAAGCCA GAATTGACAG      5040

CTTCAACAGA AAGGGTCAAC AAAAGAATGT CCATGGTGGT GTCTGGCCTG ACCCCAGAAG      5100

AATTTATGCT CGTGTACAAG TTTGCCAGAA ACACCACAT CACTTTAACT AATCTAATTA       5160

CTGAAGAGAC TACTCATGTT GTTATGAAAA CAGATGCTGA GTTTGTGTGT GAACGGACAC      5220

TGAAATATTT TCTAGGAATT GCGGGAGGAA AATGGGTAGT TAGCTATTTC TGGGTGACCC      5280

AGTCTATTAA AGAAAGAAAA ATGCTGAATG AGCATGATTT TGAAGTCAGA GGAGATGTGG      5340

TCAATGGAAG AAACCACCAA GGTCCAAAGC GAGCAAGAGA ATCCCAGGAC AGAAAGATCT      5400

TCAGGGGGCT AGAAATCTGT TGCTATGGGC CCTTCACCAA CATGCCCACA GATCAACTGG      5460

AATGGATGGT ACAGCTGTGT GGTGCTTCTG TGGTGAAGGA GCTTTCATCA TTCACCCTTG      5520

GCACAGGTGT CCACCCAATT GTGGTTGTGC AGCCAGATGC CTGGACAGAG GACAATGGCT      5580

TCCATGCAAT TGGGCAGATG TGTGAGGCAC CTGTGGTGAC CCGAGAGTGG GTGTTGGACA      5640

GTGTAGCACT CTACCAGTGC CAGGAGCTGG ACACCTACCT GATACCCCAG ATCCCCCACA      5700

GCCACTACTG A                                                          5711

(2) INFORMATION FOR SEQ ID NO: 11:

(i) SEQUENCE CHARACTERISTICS:
        (A) LENGTH: 5707 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 11:

AGCTCGCTGA GACTTCCTGG ACCCCGCACC AGGCTGTGGG GTTTCTCAGA TAACTGGGCC        60

CCTGCGCTCA GGAGGCCTTC ACCCTCTGCT CTGGGTAAAG TTCATTGGAA CAGAAAGAAA       120

TGGATTTATC TGCTCTTCGC GTTGAAGAAG TACAAAATGT CATTAATGCT ATGCAGAAAA       180

TCTTAGAGTG TCCCATCTGT CTGGAGTTGA TCAAGGAACC TGTCTCCACA AAGTGTGACC       240

ACATATTTTG CAAATTTTGC ATGCTGAAAC TTCTCAACCA GAAGAAAGGG CCTTCACAGT       300

GTCCTTTATG TAAGAATGAT ATAACCAAAA GGAGCCTACA AGAAAGTACG AGATTAGTC        360

AACTTGTTGA AGAGCTATTG AAAATCATTT GTGCTTTTCA GCTTGACACA GGTTTGGAGT       420

ATGCAAACAG CTATAATTTT GCAAAAAAGG AAAATAACTC TCCTGAACAT CTAAAAGATG       480

AAGTTTCTAT CATCCAAAGT ATGGGCTACA GAAACCGTGC CAAAAGACTT CTACAGAGTG       540

AACCCGAAAA TCCTTCCTTG CAGGAAACCA GTCTCAGTGT CCAACTCTCT AACCTTGGAA       600

CTGTGAGAAC TCTGAGGACA AGCAGCGGA TACAACCTCA AAGACGTCT GTCTACATTG         660

AATTGGGATC TGATTCTTCT GAAGATACCG TTAATAAGGC AACTTATTGC AGTGTGGGAG       720

ATCAAGAATT GTTACAAATC ACCCCTCAAG GAACCAGGGA TGAAATCAGT TTGGATTCTG       780
```

```
CAAAAAAGGC TGCTTGTGAA TTTTCTGAGA CGGATGTAAC AAATACTGAA CATCATCAAC    840
CCAGTAATAA TGATTTGAAC ACCACTGAGA AGCGTGCAGC TGAGAGGCAT CCAGAAAAGT    900
ATCAGGGTAG TTCTGTTTCA AACTTGCATG TGGAGCCATG TGGCACAAAT ACTCATGCCA    960
GCTCATTACA GCATGAGAAC AGCAGTTTAT TACTCACTAA AGACAGAATG AATGTAGAAA   1020
AGGCTGAATT CTGTAATAAA AGCAAACAGC CTGGCTTAGC AAGGAGCCAA CATAACAGAT   1080
GGGCTGGAAG TAAGGAAACA TGTAATGATA GGCGGACTCC CAGCACAGAA AAAAAGGTAG   1140
ATCTGAATGC TGATCCCCTG TGTGAGAGAA AAGAATGGAA TAAGCAGAAA CTGCCATGCT   1200
CAGAGAATCC TAGAGATACT GAAGATGTTC CTTGGATAAC ACTAAATAGC AGCATTCAGA   1260
AAGTTAATGA GTGGTTTTCC AGAAGTGATG AACTGTTAGG TTCTGATGAC TCACATGATG   1320
GGGAGTCTGA ATCAAATGCC AAAGTAGCTG ATGTATTGGA CGTTCTAAAT GAGGTAGATG   1380
AATATTCTGG TTCTTCAGAG AAAATAGACT TACTGGCCAG TGATCCTCAT GAGGCTTTAA   1440
TATGTAAAAG TGAAAGAGTT CACTCCAAAT CAGTAGAGAG TAATATTGAA GACAAAATAT   1500
TTGGGAAAAC CTATCGGAAG AAGGCAAGCC TCCCCAACTT AAGCCATGTA ACTGAAAATC   1560
TAATTATAGG AGCATTTGTT ACTGAGCCAC AGATAATACA AGAGCGTCCC CTCACAAATA   1620
AATTAAAGCG TAAAAGGAGA CCTACATCAG GCCTTCATCC TGAGGATTTT ATCAAGAAAG   1680
CAGATTTGGC AGTTCAAAAG ACTCCTGAAA TGATAAATCA GGGAACTAAC CAAACGGAGC   1740
AGAATGGTCA AGTGATGAAT ATTACTAATA GTGGTCATGA GAATAAAACA AAAGGTGATT   1800
CTATTCAGAA TGAGAAAAAT CCTAACCCAA TAGAATCACT CGAAAAAGAA TCTGCTTTCA   1860
AAACGAAAGC TGAACCTATA AGCAGCAGTA TAAGCAATAT GGAACTCGAA TTAAATATCC   1920
ACAATTCAAA AGCACCTAAA AAGAATAGGC TGAGGAGGAA GTCTTCTACC AGGCATATTC   1980
ATGCGCTTGA ACTAGTAGTC AGTAGAAATC TAAGCCCACC TAATTGTACT GAATTGCAAA   2040
TTGATAGTTG TTCTAGCAGT GAAGAGATAA AGAAAAAAAA GTACAACCAA ATGCCAGTCA   2100
GGCACAGCAG AAAACCTACA CTCATGGAAG GTAAAGAACC TGCAACTGGA GCCAAGAAGA   2160
GTAACAAGCC AAATGAACAG ACAAGTAAAA GACATGCAGG CGATACTTTC CCAGAGCTGA   2220
AGTTAACAAA TGCACCTGGT TCTTTTACTA AGTGTTCAAA TACCAGTGAA CTTAAAGAAT   2280
TTGTCAATCC TAGCCTTCCA AGAGAAGAAA AAGAAGAGAA ACTAGAAACA GTTAAAGTGT   2340
CTAATAATGC TGAAGACCCC AAAGATCTCA TGTTAAGTGG AGAAAGGGTT TTGCAAACTG   2400
AAAGATCTGT AGAGAGTAGC AGTATTTCAT TGGTACCTGG TACTGATTAT GGCACTCAGG   2460
AAAGTATCTC GTTACTGGAA GTTAGCACTC TAGGGAAGGC AAAAACAGAA CCAAATAAAT   2520
GTGTGAGTCA GTGTGCAGCA TTTGAAAACC CCAAGGGACT AATTCATGGT TGTTCCAAAG   2580
ATAATAGAAA TGACACAGAA GGCTTTAAGT ATCCATTGGG ACATGAAGTT AACCACAGTC   2640
GGGAAACAAG CATAGAAATG GAAGAAAGTG AACTTGATGC TCAGTATTTG CAGAATACAT   2700
TCAAGGTTTC AAAGCGCCAG TCATTTGCTC CGTTTTCAAA TCCAGGAAAT GCAGAAGAGG   2760
AATGTGCAAC ATTCTCTGCC CACTCTGGGT CCTTAAAGAA ACAAAGTCCA AAAGTCACTT   2820
TTGAATGTGA ACAAAAGGAA GAAAATCAAG GAAAGAATGA GTCTAATATC AAGCCTGTAC   2880
AGACAGTTAA TATCACTGCA GGCTTTCCTG TGGTTGGTCA GAAAGATAAG CCAGTTGATA   2940
ATGCCAAATG TAGTATCAAA GGAGGCTCTA GGTTTTGTCT ATCATCTCAG TTCAGAGGCA   3000
ACGAAACTGG ACTCATTACT CCAAATAAAC ATGGACTTTT ACAAAACCCA TATCGTATAC   3060
CACCACTTTT TCCCATCAAG TCATTTGTTA AAACTAAATG TAAGAAAAAT CTGCTAGAGG   3120
AAAACTTTGA GGAACATTCA ATGTCACCTG AAAGAGAAAT GGGAAATGAG AACATTCCAA   3180
```

-continued

```
GTACAGTGAG CACAATTAGC CGTAATAACA TTAGAGAAAA TGTTTTTAAA GAAGCCAGCT    3240

CAAGCAATAT TAATGAAGTA GGTTCCAGTA CTAATGAAGT GGGCTCCAGT ATTAATGAAA    3300

TAGGTTCCAG TGATGAAAAC ATTCAAGCAG AACTAGGTAG AAACAGAGGG CCAAAATTGA    3360

ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480

ATACAGATTT CTCTCCATAT CTGATTTCAG ATAACTTAGA ACAGCCTATG GAAGTAGTC     3540

ATGCATCTCA GGTTTGTTCT GAGACACCTG ATGACCTGTT AGATGATGGT GAAATAAAGG    3600

AAGATACTAG TTTTGCTGAA AATGACATTA GGAAAGTTC TGCTGTTTTT AGCAAAAGCG     3660

TCCAGAAAGG AGAGCTTAGC AGGAGTCCTA GCCCTTTCAC CCATACACAT TTGGCTCAGG    3720

GTTACCGAAG AGGGGCCAAG AAATTAGAGT CCTCAGAAGA GAACTTATCT AGTGAGGATG    3780

AAGAGCTTCC CTGCTTCCAA CACTTGTTAT TTGGTAAAGT AAACAATATA CCTTCTCAGT    3840

CTACTAGGCA TAGCACCGTT GCTACCGAGT GTCTGTCTAA GAACACAGAG GAGAATTTAT    3900

TATCATTGAA GAATAGCTTA AATGACTGCA GTAACCAGGT AATATTGGCA AAGGCATCTC    3960

AGGAACATCA CCTTAGTGAG GAAACAAAAT GTTCTGCTAG CTTGTTTTCT TCACAGTGCA    4020

GTGAATTGGA AGACTTGACT GCAAATACAA ACACCCAGGA TCCTTTCTTG ATTGGTTCTT    4080

CCAAACAAAT GAGGCATCAG TCTGAAAGCC AGGGAGTTGG TCTGAGTGAC AAGGAATTGG    4140

TTTCAGATGA TGAAGAAAGA GGAACGGGCT TGGAAGAAAA TAAGAAGAGC AAAGCATGGA    4200

TTCAAACTTA GGTGAAGCAG CATCTGGGTG TGAGAGTGAA ACAAGCGTCT CTGAAGACTG    4260

CTCAGGGCTA TCCTCTCAGA GTGACATTTT AACCACTCAG CAGAGGGATA CCATGCAACA    4320

TAACCTGATA AAGCTCCAGC AGGAAATGGC TGAACTAGAA GCTGTGTTAG AACAGCATGG    4380

GAGCCAGCCT TCTAACAGCT ACCCTTCCAT CATAAGTGAC TCTTCTGCCC TTGAGGACCT    4440

GCGAAATCCA GAACAAAGCA CATCAGAAAA AGCAGTATTA ACTTCACAGA AAAGTAGTGA    4500

ATACCCTATA AGCCAGAATC CAGAAGGCCT TTCTGCTGAC AAGTTTGAGG TGTCTGCAGA    4560

TAGTTCTACC AGTAAAAATA AGAACCAGG AGTGGAAAGG TCATCCCCTT CTAAATGCCC     4620

ATCATTAGAT GATAGGTGGT ACATGCACAG TTGCTCTGGG AGTCTTCAGA ATAGAAACTA    4680

CCCATCTCAA GAGGAGCTCA TTAAGGTTGT TGATGTGGAG GAGCAACAGC TGGAAGAGTC    4740

TGGGCCACAC GATTTGACGG AAACATCTTA CTTGCCAAGG CAAGATCTAG AGGGAACCCC    4800

TTACCTGGAA TCTGGAATCA GCCTCTTCTC TGATGACCCT GAATCTGATC CTTCTGAAGA    4860

CAGAGCCCCA GAGTCAGCTC GTGTTGGCAA CATACCATCT TCAACCTCTG CATTGAAAGT    4920

TCCCCAATTG AAAGTTGCAG AATCTGCCCA GAGTCCAGCT GCTGCTCATA CTACTGATAC    4980

TGCTGGGTAT AATGCAATGG AAGAAAGTGT GAGCAGGGAG AAGCCAGAAT TGACAGCTTC    5040

AACAGAAAGG GTCAACAAAA GAATGTCCAT GGTGGTGTCT GGCCTGACCC CAGAAGAATT    5100

TATGCTCGTG TACAAGTTTG CCAGAAAACA CCACATCACT TTAACTAATC TAATTACTGA    5160

AGAGACTACT CATGTTGTTA TGAAAACAGA TGCTGAGTTT GTGTGTGAAC GGACACTGAA    5220

ATATTTTCTA GGAATTGCGG GAGGAAAATG GGTAGTTAGC TATTTCTGGG TGACCCAGTC    5280

TATTAAAGAA AGAAAAATGC TGAATGAGCA TGATTTTGAA GTCAGAGGAG ATGTGGTCAA    5340

TGGAAGAAAC CACCAAGGTC CAAAGCGAGC AAGAGAATCC CAGGACAGAA AGATCTTCAG    5400

GGGGCTAGAA ATCTGTTGCT ATGGGCCCTT CACCAACATG CCCACAGATC AACTGGAATG    5460

GATGGTACAG CTGTGTGGTG CTTCTGTGGT GAAGGAGCTT TCATCATTCA CCCTTGGCAC    5520
```

```
AGGTGTCCAC CCAATTGTGG TTGTGCAGCC AGATGCCTGG ACAGAGGACA ATGGCTTCCA      5580

TGCAATTGGG CAGATGTGTG AGGCACCTGT GGTGACCCGA GAGTGGGTGT TGGACAGTGT      5640

AGCACTCTAC CAGTGCCAGG AGCTGGACAC CTACCTGATA CCCCAGATCC CCCACAGCCA      5700

CTACTGA                                                                5707
```

(2) INFORMATION FOR SEQ ID NO: 12:

(i) SEQUENCE CHARACTERISTICS:
        (A) LENGTH: 5712 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 12:

```
AGCTCGCTGA GACTTCCTGG ACCCCGCACC AGGCTGTGGG GTTTCTCAGA TAACTGGGCC        60

CCTGCGCTCA GGAGGCCTTC ACCCTCTGCT CTGGGTAAAG TTCATTGGAA CAGAAAGAAA       120

TGGATTTATC TGCTCTTCGC GTTGAAGAAG TACAAAATGT CATTAATGCT ATGCAGAAAA       180

TCTTAGAGTG TCCCATCTGT CTGGAGTTGA TCAAGGAACC TGTCTCCACA AAGTGTGACC       240

ACATATTTTG CAAATTTTGC ATGCTGAAAC TTCTCAACCA GAAGAAAGGG CCTTCACAGT       300

GTCCTTTATG TAAGAATGAT ATAACCAAAA GGAGCCTACA AGAAAGTACG AGATTTAGTC       360

AACTTGTTGA AGAGCTATTG AAAATCATTT GTGCTTTTCA GCTTGACACA GGTTTGGAGT       420

ATGCAAACAG CTATAATTTT GCAAAAAAGG AAAATAACTC TCCTGAACAT CTAAAAGATG       480

AAGTTTCTAT CATCCAAAGT ATGGGCTACA GAAACCGTGC CAAAAGACTT CTACAGAGTG       540

AACCCGAAAA TCCTTCCTTG CAGGAAACCA GTCTCAGTGT CCAACTCTCT AACCTTGGAA       600

CTGTGAGAAC TCTGAGGACA AAGCAGCGGA TACAACCTCA AAAGACGTCT GTCTACATTG       660

AATTGGGATC TGATTCTTCT GAAGATACCG TTAATAAGGC AACTTATTGC AGTGTGGGAG       720

ATCAAGAATT GTTACAAATC ACCCCTCAAG GAACCAGGGA TGAAATCAGT TTGGATTCTG       780

CAAAAAAGGC TGCTTGTGAA TTTTCTGAGA CGGATGTAAC AAATACTGAA CATCATCAAC       840

CCAGTAATAA TGATTTGAAC ACCACTGAGA AGCGTGCAGC TGAGAGGCAT CCAGAAAAGT       900

ATCAGGGTAG TTCTGTTTCA AACTTGCATG TGGAGCCATG TGGCACAAAT ACTCATGCCA       960

GCTCATTACA GCATGAGAAC AGCAGTTTAT TACTCACTAA AGACAGAATG AATGTAGAAA      1020

AGGCTGAATT CTGTAATAAA AGCAAACAGC CTGGCTTAGC AAGGAGCCAA CATAACAGAT      1080

GGGCTGGAAG TAAGGAAACA TGTAATGATA GGCGGACTCC CAGCACAGAA AAAAAGGTAG      1140

ATCTGAATGC TGATCCCCTG TGTGAGAGAA AAGAATGGAA TAAGCAGAAA CTGCCATGCT      1200

CAGAGAATCC TAGAGATACT GAAGATGTTC CTTGGATAAC ACTAAATAGC AGCATTCAGA      1260

AAGTTAATGA GTGGTTTTCC AGAAGTGATG AACTGTTAGG TTCTGATGAC TCACATGATG      1320

GGGAGTCTGA ATCAAATGCC AAAGTAGCTG ATGTATTGGA CGTTCTAAAT GAGGTAGATG      1380

AATATTCTGG TTCTTCAGAG AAAATAGACT TACTGGCCAG TGATCCTCAT GAGGCTTTAA      1440

TATGTAAAAG TGAAAGAGTT CACTCCAAAT CAGTAGAGAG TAATATTGAA GACAAAATAT      1500

TTGGGAAAAC CTATCGGAAG AAGGCAAGCC TCCCCAACTT AAGCCATGTA ACTGAAAATC      1560

TAATTATAGG AGCATTTGTT ACTGAGCCAC AGATAATACA AGAGCGTCCC CTCACAAATA      1620

AATTAAAGCG TAAAAGGAGA CCTACATCAG GCCTTCATCC TGAGGATTTT ATCAAGAAAG      1680

CAGATTTGGC AGTTCAAAAG ACTCCTGAAA TGATAAATCA GGGAACTAAC CAAACGGAGC      1740
```

-continued

```
AGAATGGTCA AGTGATGAAT ATTACTAATA GTGGTCATGA GAATAAAACA AAAGGTGATT       1800

CTATTCAGAA TGAGAAAAAT CCTAACCCAA TAGAATCACT CGAAAAGAA TCTGCTTTCA        1860

AAACGAAAGC TGAACCTATA AGCAGCAGTA TAAGCAATAT GGAACTCGAA TTAAATATCC       1920

ACAATTCAAA AGCACCTAAA AAGAATAGGC TGAGGAGGAA GTCTTCTACC AGGCATATTC       1980

ATGCGCTTGA ACTAGTAGTC AGTAGAAATC TAAGCCCACC TAATTGTACT GAATTGCAAA       2040

TTGATAGTTG TTCTAGCAGT GAAGAGATAA AGAAAAAAAA GTACAACCAA ATGCCAGTCA       2100

GGCACAGCAG AAACCTACAA CTCATGGAAG GTAAAGAACC TGCAACTGGA GCCAAGAAGA       2160

GTAACAAGCC AAATGAACAG ACAAGTAAAA GACATGACAG CGATACTTTC CCAGAGCTGA       2220

AGTTAACAAA TGCACCTGGT TCTTTTACTA AGTGTTCAAA TACCAGTGAA CTTAAAGAAT       2280

TTGTCAATCC TAGCCTTCCA AGAGAAGAAA AAGAAGAGAA ACTAGAAACA GTTAAAGTGT       2340

CTAATAATGC TGAAGACCCC AAAGATCTCA TGTTAAGTGG AGAAAGGGTT TTGCAAACTG       2400

AAAGATCTGT AGAGAGTAGC AGTATTTCAT TGGTACCTGG TACTGATTAT GGCACTCAGG       2460

AAAGTATCTC GTTACTGGAA GTTAGCACTC TAGGGAAGGC AAAAACAGAA CCAAATAAAT       2520

GTGTGAGTCA GTGTGCAGCA TTTGAAAACC CCAAGGGACT AATTCATGGT TGTTCCAAAG       2580

ATAATAGAAA TGCACAGAA GGCTTTAAGT ATCCATTGGG ACATGAAGTT AACCACAGTC        2640

GGGAAACAAG CATAGAAATG GAAGAAAGTG AACTTGATGC TCAGTATTTG CAGAATACAT       2700

TCAAGGTTTC AAAGCGCCAG TCATTTGCTC CGTTTTCAAA TCCAGGAAAT GCAGAAGAGG       2760

AATGTGCAAC ATTCTCTGCC CACTCTGGGT CCTTAAAGAA ACAAAGTCCA AAAGTCACTT       2820

TTGAATGTGA ACAAAAGGAA GAAAATCAAG GAAAGAATGA GTCTAATATC AAGCCTGTAC       2880

AGACAGTTAA TATCACTGCA GGCTTTCCTG TGGTTGGTCA GAAAGATAAG CCAGTTGATA       2940

ATGCCAAATG TAGTATCAAA GGAGGCTCTA GGTTTTGTCT ATCATCTCAG TTCAGAGGCA       3000

ACGAAACTGG ACTCATTACT CCAAATAAAC ATGGACTTTT ACAAAACCCA TATCGTATAC       3060

CACCACTTTT TCCCATCAAG TCATTTGTTA AAACTAAATG TAAGAAAAAT CTGCTAGAGG       3120

AAAACTTTGA GGAACATTCA ATGTCACCTG AAAGAGAAAT GGGAAATGAG AACATTCCAA       3180

GTACAGTGAG CACAATTAGC CGTAATAACA TTAGAGAAAA TGTTTTTAAA GAAGCCAGCT       3240

CAAGCAATAT TAATGAAGTA GGTTCCAGTA CTAATGAAGT GGGCTCCAGT ATTAATGAAA       3300

TAGGTTCCAG TGATGAAAAC ATTCAAGCAG AACTAGGTAG AAACAGAGGG CCAAAATTGA       3360

ATGCTATGCT TAGATTAGGG GTTTTGCAAC CTGAGGTCTA TAAACAAAGT CTTCCTGGAA       3420

GTAATTGTAA GCATCCTGAA ATAAAAAAGC AAGAATATGA AGAAGTAGTT CAGACTGTTA       3480

ATACAGATTT CTCTCCATAT CTGATTTCAG ATAACTTAGA ACAGCCTATG GAAGTAGTC        3540

ATGCATCTCA GGTTTGTTCT GAGACACCTG ATGACCTGTT AGATGATGGT GAAATAAAGG       3600

AAGATACTAG TTTTGCTGAA AATGACATTA AGGAAAGTTC TGCTGTTTTT AGCAAAAGCG       3660

TCCAGAAAGG AGAGCTTAGC AGGAGTCCTA GCCCTTTCAC CCATACACAT TTGGCTCAGG       3720

GTTACCGAAG AGGGGCCAAG AAATTAGAGT CCTCAGAAGA GAACTTATCT AGTGAGGATG       3780

AAGAGCTTCC CTGCTTCCAA CACTTGTTAT TTGGTAAAGT AAACAATATA CCTTCTCAGT       3840

CTACTAGGCA TAGCACCGTT GCTACCGAGT GTCTGTCTAA GAACACAGAG GAGAATTTAT       3900

TATCATTGAA GAATAGCTTA AATGACTGCA GTAACCAGGT AATATTGGCA AAGGCATCTC       3960

AGGAACATCA CCTTAGTGAG GAAACAAAAT GTTCTGCTAG CTTGTTTTCT TCACAGTGCA       4020

GTGAATTGGA AGACTTGACT GCAAATACAA ACACCCAGGA TCCTTTCTTG ATTGGTTCTT       4080

CCAAACAAAT GAGGCATCAG TCTGAAAGCC AGGGAGTTGG TCTGAGTGAC AAGGAATTGG       4140
```

-continued

```
TTTCAGATGA TGAAGAAAGA GGAACGGGCT TGGAAGAAAA TAATCAAGAA GAGCAAAGCA      4200

TGGATTCAAA CTTAGGTGAA GCAGCATCTG GGTGTGAGAG TGAAACAAGC GTCTCTGAAG      4260

ACTGCTCAGG GCTATCCTCT CAGAGTGACA TTTTAACCAC TCAGCAGAGG GATACCATGC      4320

AACATAACCT GATAAAGCTC CAGCAGGAAA TGGCTGAACT AGAAGCTGTG TTAGAACAGC      4380

ATGGGAGCCA GCCTTCTAAC AGCTACCCTT CCATCATAAG TGACTCTTCT GCCCTTGAGG      4440

ACCTGCGAAA TCCAGAACAA AGCACATCAG AAAAAGCAGT ATTAACTTCA CAGAAAAGTA      4500

GTGAATACCC TATAAGCCAG AATCCAGAAG GCCTTTCTGC TGACAAGTTT GAGGTGTCTG      4560

CAGATAGTTC TACCAGTAAA AATAAAGAAC CAGGAGTGGA AAGGTCATCC CCTTCTAAAT      4620

GCCCATCATT AGATGATAGG TGGTACATGC ACAGTTGCTC TGGGAGTCTT CAGAATAGAA      4680

ACTACCCATC TCAAGAGGAG CTCATTAAGG TTGTTGATGT GGAGGAGCAA CAGCTGGAAG      4740

AGTCTGGGCC ACACGATTTG ACGGAAACAT CTTACTTGCC AAGGCAAGAT CTAGAGGGAA      4800

CCCCTTACCT GGAATCTGGA ATCAGCCTCT TCTCTGATGA CCCTGAATCT GATCCTTCTG      4860

AAGACAGAGC CCCAGAGTCA GCTCGTGTTG CAACATACC ATCTTCAACC TCTGCATTGA       4920

AAGTTCCCCA ATTGAAAGTT GCAGAATCTG CCCAGAGTCC AGCTGCTGCT CATACTACTG      4980

ATACTGCTGG GTATAATGCA ATGGAAGAAA GTGTGAGCAG GGAGAAGCCA GAATTGACAG      5040

CTTCAACAGA AAGGGTCAAC AAAAGAATGT CCATGGTGGT GTCTGGCCTG ACCCCAGAAG      5100

AATTTATGCT CGTGTACAAG TTTGCCAGAA AACACCACAT CACTTTAACT AATCTAATTA      5160

CTGAAGAGAC TACTCATGTT GTTATGAAAA CAGATGCTGA GTTTGTGTGT GAACGGACAC      5220

TGAAATATTT TCTAGGAATT GCGGGAGGAA AATGGGTAGT TAGCTATTTC TGGGTGACCC      5280

AGTCTATTAA AGAAAGAAAA ATGCTGAATG AGCATGATTT TGAAGTCAGA GGAGATGTGG      5340

TCAATGGAAG AAACCACCAA GGTCCAAAGC GAGCAAGAGA ATCCCAGGAC AGAAAGATCT      5400

TCAGGGGGCT AGAAATCTGT TGCTATGGGC CCTTCACCAA CATGCCCACA GATCAACTGG      5460

AATGGATGGT ACAGCTGTGT GGTGCTTCTG TGGTGAAGGA GCTTTCATCA TTCACCCTTG      5520

GCACAGGTGT CCACCCAATT GTGGTTGTGC AGCCAGATGC CTGGACAGAG GACAATGGCT      5580

TCCATGCAAT TGGGCAGATG TGTGAGGCAC CTGTGGTGAC CCGAGAGTGG GTGTTGGACA      5640

GTGTAGCACT CTACCAGTGC CAGGAGCTGG ACACCTAACC TGATACCCCA GATCCCCCAC      5700

AGCCACTACT GA                                                         5712
```

(2) INFORMATION FOR SEQ ID NO: 13:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

```
Met Asp Leu Ser Ala Leu Arg Val Glu Glu Val Gln Asn Val Ile Asn
1               5                  10                  15

Ala Met Gln Lys Ile Leu Glu Cys Pro Ile
                20                  25
```

(2) INFORMATION FOR SEQ ID NO: 14:

(i) SEQUENCE CHARACTERISTICS:
        (A) LENGTH: 38 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Val
            35

(2) INFORMATION FOR SEQ ID NO: 15:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu
    50                  55                  60

(2) INFORMATION FOR SEQ ID NO: 16:

(i) SEQUENCE CHARACTERISTICS:
        (A) LENGTH: 1863 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Gly Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
            85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
            115                 120                 125

```
Gly Tyr Arg Asn Arg Ala Lys Arg Leu Leu Gln Ser Glu Pro Glu Asn
            130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
        210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
        370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
        450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
        530                 535                 540

Val Met Asn Ile Thr Asn Ser Gly His Glu Asn Lys Thr Lys Gly Asp
```

-continued

```
                545                 550                 555                 560
        Ser Ile Gln Asn Glu Lys Asn Pro Asn Pro Ile Glu Ser Leu Glu Lys
                        565                 570                 575

Glu Ser Ala Phe Lys Thr Lys Ala Glu Pro Ile Ser Ser Ile Ser
                        580                 585                 590

Asn Met Glu Leu Glu Leu Asn Ile His Asn Ser Lys Ala Pro Lys Lys
                        595                 600                 605

Asn Arg Leu Arg Arg Lys Ser Ser Thr Arg His Ile His Ala Leu Glu
                        610                 615                 620

Leu Val Val Ser Arg Asn Leu Ser Pro Pro Asn Cys Thr Glu Leu Gln
        625                 630                 635                 640

Ile Asp Ser Cys Ser Ser Ser Glu Glu Ile Lys Lys Lys Lys Tyr Asn
                        645                 650                 655

Gln Met Pro Val Arg His Ser Arg Asn Leu Gln Leu Met Glu Gly Lys
                        660                 665                 670

Glu Pro Ala Thr Gly Ala Lys Lys Ser Asn Lys Pro Asn Glu Gln Thr
                        675                 680                 685

Ser Lys Arg His Asp Ser Asp Thr Phe Pro Glu Leu Lys Leu Thr Asn
                        690                 695                 700

Ala Pro Gly Ser Phe Thr Lys Cys Ser Asn Thr Ser Glu Leu Lys Glu
        705                 710                 715                 720

Phe Val Asn Pro Ser Leu Pro Arg Glu Glu Lys Glu Glu Lys Leu Glu
                        725                 730                 735

Thr Val Lys Val Ser Asn Asn Ala Glu Asp Pro Lys Asp Leu Met Leu
                        740                 745                 750

Ser Gly Glu Arg Val Leu Gln Thr Glu Arg Ser Val Glu Ser Ser Ser
                        755                 760                 765

Ile Ser Leu Val Pro Gly Thr Asp Tyr Gly Thr Gln Glu Ser Ile Ser
                        770                 775                 780

Leu Leu Glu Val Ser Thr Leu Gly Lys Ala Lys Thr Glu Pro Asn Lys
        785                 790                 795                 800

Cys Val Ser Gln Cys Ala Ala Phe Glu Asn Pro Lys Gly Leu Ile His
                        805                 810                 815

Gly Cys Ser Lys Asp Asn Arg Asn Asp Thr Glu Gly Phe Lys Tyr Pro
                        820                 825                 830

Leu Gly His Glu Val Asn His Ser Arg Glu Thr Ser Ile Glu Met Glu
                        835                 840                 845

Glu Ser Glu Leu Asp Ala Gln Tyr Leu Gln Asn Thr Phe Lys Val Ser
        850                 855                 860

Lys Arg Gln Ser Phe Ala Pro Phe Ser Asn Pro Gly Asn Ala Glu Glu
        865                 870                 875                 880

Glu Cys Ala Thr Phe Ser Ala His Ser Gly Ser Leu Lys Lys Gln Ser
                        885                 890                 895

Pro Lys Val Thr Phe Glu Cys Glu Gln Lys Glu Glu Asn Gln Gly Lys
                        900                 905                 910

Asn Glu Ser Asn Ile Lys Pro Val Gln Thr Val Asn Ile Thr Ala Gly
                        915                 920                 925

Phe Pro Val Val Gly Gln Lys Asp Lys Pro Val Asp Asn Ala Lys Cys
                        930                 935                 940

Ser Ile Lys Gly Gly Ser Arg Phe Cys Leu Ser Ser Gln Phe Arg Gly
        945                 950                 955                 960

Asn Glu Thr Gly Leu Ile Thr Pro Asn Lys His Gly Leu Leu Gln Asn
                        965                 970                 975
```

-continued

```
Pro Tyr Arg Ile Pro Pro Leu Phe Pro Ile Lys Ser Phe Val Lys Thr
            980                 985                 990
Lys Cys Lys Lys Asn Leu Leu Glu Glu Asn Phe Glu Glu His Ser Met
            995                1000                1005
Ser Pro Glu Arg Glu Met Gly Asn Glu Asn Ile Pro Ser Thr Val Ser
           1010                1015                1020
Thr Ile Ser Arg Asn Asn Ile Arg Glu Asn Val Phe Lys Glu Ala Ser
1025                1030                1035                1040
Ser Ser Asn Ile Asn Glu Val Gly Ser Ser Thr Asn Glu Val Gly Ser
           1045                1050                1055
Ser Ile Asn Glu Ile Gly Ser Ser Asp Glu Asn Ile Gln Ala Glu Leu
           1060                1065                1070
Gly Arg Asn Arg Gly Pro Lys Leu Asn Ala Met Leu Arg Leu Gly Val
           1075                1080                1085
Leu Gln Pro Glu Val Tyr Lys Gln Ser Leu Pro Gly Ser Asn Cys Lys
           1090                1095                1100
His Pro Glu Ile Lys Lys Gln Glu Tyr Glu Glu Val Val Gln Thr Val
1105                1110                1115                1120
Asn Thr Asp Phe Ser Pro Tyr Leu Ile Ser Asp Asn Leu Glu Gln Pro
           1125                1130                1135
Met Gly Ser Ser His Ala Ser Gln Val Cys Ser Glu Thr Pro Asp Asp
           1140                1145                1150
Leu Leu Asp Asp Gly Glu Ile Lys Glu Asp Thr Ser Phe Ala Glu Asn
           1155                1160                1165
Asp Ile Lys Glu Ser Ser Ala Val Phe Ser Lys Ser Val Gln Lys Gly
           1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
           1205                1210                1215
Ser Ser Glu Asp Glu Glu Leu Pro Cys Phe Gln His Leu Leu Phe Gly
           1220                1225                1230
Lys Val Asn Asn Ile Pro Ser Gln Ser Thr Arg His Ser Thr Val Ala
           1235                1240                1245
Thr Glu Cys Leu Ser Lys Asn Thr Glu Glu Asn Leu Leu Ser Leu Lys
           1250                1255                1260
Asn Ser Leu Asn Asp Cys Ser Asn Gln Val Ile Leu Ala Lys Ala Ser
1265                1270                1275                1280
Gln Glu His His Leu Ser Glu Glu Thr Lys Cys Ser Ala Ser Leu Phe
           1285                1290                1295
Ser Ser Gln Cys Ser Glu Leu Glu Asp Leu Thr Ala Asn Thr Asn Thr
           1300                1305                1310
Gln Asp Pro Phe Leu Ile Gly Ser Ser Lys Gln Met Arg His Gln Ser
           1315                1320                1325
Glu Ser Gln Gly Val Gly Leu Ser Asp Lys Glu Leu Val Ser Asp Asp
           1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
           1365                1370                1375
Ser Val Ser Glu Asp Cys Ser Gly Leu Ser Ser Gln Ser Asp Ile Leu
           1380                1385                1390
```

```
Thr Thr Gln Gln Arg Asp Thr Met Gln His Asn Leu Ile Lys Leu Gln
        1395                1400                1405
Gln Glu Met Ala Glu Leu Glu Ala Val Leu Glu Gln His Gly Ser Gln
    1410                1415                1420
Pro Ser Asn Ser Tyr Pro Ser Ile Ile Ser Asp Ser Ser Ala Leu Glu
1425                1430                1435                1440
Asp Leu Arg Asn Pro Glu Gln Ser Thr Ser Glu Lys Ala Val Leu Thr
            1445                1450                1455
Ser Gln Lys Ser Ser Glu Tyr Pro Ile Ser Gln Asn Pro Glu Gly Leu
        1460                1465                1470
Ser Ala Asp Lys Phe Glu Val Ser Ala Asp Ser Ser Thr Ser Lys Asn
    1475                1480                1485
Lys Glu Pro Gly Val Glu Arg Ser Ser Pro Ser Lys Cys Pro Ser Leu
    1490                1495                1500
Asp Asp Arg Trp Tyr Met His Ser Cys Ser Gly Ser Leu Gln Asn Arg
1505                1510                1515                1520
Asn Tyr Pro Ser Gln Glu Glu Leu Ile Lys Val Val Asp Val Glu Glu
            1525                1530                1535
Gln Gln Leu Glu Glu Ser Gly Pro His Asp Leu Thr Glu Thr Ser Tyr
        1540                1545                1550
Leu Pro Arg Gln Asp Leu Glu Gly Thr Pro Tyr Leu Glu Ser Gly Ile
    1555                1560                1565
Ser Leu Phe Ser Asp Asp Pro Glu Ser Asp Pro Ser Glu Asp Arg Ala
    1570                1575                1580
Pro Glu Ser Ala Arg Val Gly Asn Ile Pro Ser Ser Thr Ser Ala Leu
1585                1590                1595                1600
Lys Val Pro Gln Leu Lys Val Ala Glu Ser Ala Gln Ser Pro Ala Ala
            1605                1610                1615
Ala His Thr Thr Asp Thr Ala Gly Tyr Asn Ala Met Glu Glu Ser Val
        1620                1625                1630
Ser Arg Glu Lys Pro Glu Leu Thr Ala Ser Thr Glu Arg Val Asn Lys
        1635                1640                1645
Arg Met Ser Met Val Val Ser Gly Leu Thr Pro Glu Glu Phe Met Leu
    1650                1655                1660
Val Tyr Lys Phe Ala Arg Lys His His Ile Thr Leu Thr Asn Leu Ile
1665                1670                1675                1680
Thr Glu Glu Thr Thr His Val Val Met Lys Thr Asp Ala Glu Phe Val
            1685                1690                1695
Cys Glu Arg Thr Leu Lys Tyr Phe Leu Gly Ile Ala Gly Gly Lys Trp
            1700                1705                1710
Val Val Ser Tyr Phe Trp Val Thr Gln Ser Ile Lys Glu Arg Lys Met
        1715                1720                1725
Leu Asn Glu His Asp Phe Glu Val Arg Gly Asp Val Val Asn Gly Arg
    1730                1735                1740
Asn His Gln Gly Pro Lys Arg Ala Arg Glu Ser Gln Asp Arg Lys Ile
1745                1750                1755                1760
Phe Arg Gly Leu Glu Ile Cys Cys Tyr Gly Pro Phe Thr Asn Met Pro
            1765                1770                1775
Thr Asp Gln Leu Glu Trp Met Val Gln Leu Cys Gly Ala Ser Val Val
        1780                1785                1790
Lys Glu Leu Ser Ser Phe Thr Leu Gly Thr Gly Val His Pro Ile Val
        1795                1800                1805
Val Val Gln Pro Asp Ala Trp Thr Glu Asp Asn Gly Phe His Ala Ile
```

-continued

```
              1810                1815                1820
Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
              1845                1850                1855

Gln Ile Pro His Ser His Tyr
              1860
```

(2) INFORMATION FOR SEQ ID NO: 17:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Ser Val Leu Lys Arg Leu Ile Ile Thr Cys
65                  70                  75                  80
```

(2) INFORMATION FOR SEQ ID NO: 18:

(i) SEQUENCE CHARACTERISTICS:
        (A) LENGTH: 312 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140
```

```
Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
                180                 185                 190

Lys Ala Thr Tyr Cys Ser Val Gly Asp Gln Glu Leu Leu Gln Ile Thr
                195                 200                 205

Pro Gln Gly Thr Arg Asp Glu Ile Ser Leu Asp Ser Ala Lys Lys Ala
210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
                260                 265                 270

Pro Cys Gly Thr Asn Thr His Ala Ser Ser Leu Gln His Glu Asn Ser
                275                 280                 285

Ser Leu Leu Leu Thr Lys Asp Arg Met Asn Val Glu Lys Ala Glu Phe
290                 295                 300

Cys Asn Lys Ser Lys Arg Leu Ala
305                 310

(2) INFORMATION FOR SEQ ID NO: 19:

(i) SEQUENCE CHARACTERISTICS:
        (A) LENGTH: 765 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
                35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
                100                 105                 110

Asn Ser Pro Glu His Leu Lys Asp Glu Val Ser Ile Ile Gln Ser Met
                115                 120                 125

Gly Tyr Arg Asn Arg Ala Lys Arg Leu Leu Gln Ser Glu Pro Glu Asn
                130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175
```

-continued

```
Ser Val Tyr Ile Glu Leu Gly Ser Asp Ser Glu Asp Thr Val Asn
            180                 185                 190
Lys Ala Thr Tyr Cys Ser Val Gly Asp Gln Glu Leu Leu Gln Ile Thr
            195                 200                 205
Pro Gln Gly Thr Arg Asp Glu Ile Ser Leu Asp Ser Ala Lys Lys Ala
        210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
        275                 280                 285
Ser Leu Leu Leu Thr Lys Asp Arg Met Asn Val Glu Lys Ala Glu Phe
        290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
        355                 360                 365
Asp Val Pro Trp Ile Thr Leu Asn Ser Ser Ile Gln Lys Val Asn Glu
    370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
        435                 440                 445
Ser Lys Ser Val Glu Ser Asn Ile Glu Asp Lys Ile Phe Gly Lys Thr
        450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
        515                 520                 525
Pro Glu Met Ile Asn Gln Gly Thr Asn Gln Thr Glu Gln Asn Gly Gln
        530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Lys Thr Lys Ala Glu Pro Ile Ser Ser Ser Ile Ser
            580                 585                 590
Asn Met Glu Leu Glu Leu Asn Ile His Asn Ser Lys Ala Pro Lys Lys
```

```
                    595                 600                 605
Asn Arg Leu Arg Arg Lys Ser Ser Thr Arg His Ile His Ala Leu Glu
            610                 615                 620

Leu Val Val Ser Arg Asn Leu Ser Pro Pro Asn Cys Thr Glu Leu Gln
625                 630                 635                 640

Ile Asp Ser Cys Ser Ser Glu Glu Ile Lys Lys Lys Tyr Asn
                    645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
        690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Lys Leu Glu
                    725                 730                 735

Thr Val Lys Val Ser Asn Asn Ala Glu Asp Pro Lys Asp Leu Met Leu
                740                 745                 750

Ser Gly Glu Arg Val Leu Gln Thr Glu Arg Ser Val Glu
            755                 760                 765

(2) INFORMATION FOR SEQ ID NO: 20:

(i) SEQUENCE CHARACTERISTICS:
        (A) LENGTH: 900 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
```

-continued

```
            180                 185                 190
Lys Ala Thr Tyr Cys Ser Val Gly Asp Gln Glu Leu Leu Gln Ile Thr
            195                 200                 205
Pro Gln Gly Thr Arg Asp Glu Ile Ser Leu Asp Ser Ala Lys Lys Ala
            210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
            275                 280                 285
Ser Leu Leu Leu Thr Lys Asp Arg Met Asn Val Glu Lys Ala Glu Phe
            290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
            355                 360                 365
Asp Val Pro Trp Ile Thr Leu Asn Ser Ser Ile Gln Lys Val Asn Glu
            370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
            435                 440                 445
Ser Lys Ser Val Glu Ser Asn Ile Glu Asp Lys Ile Phe Gly Lys Thr
            450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
            515                 520                 525
Pro Glu Met Ile Asn Gln Gly Thr Asn Gln Thr Glu Gln Asn Gly Gln
            530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Lys Thr Lys Ala Glu Pro Ile Ser Ser Ser Ile Ser
            580                 585                 590
Asn Met Glu Leu Glu Leu Asn Ile His Asn Ser Lys Ala Pro Lys Lys
            595                 600                 605
```

```
Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Tyr Asn
                645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
                675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
                740                 745                 750

Ser Gly Glu Arg Val Leu Gln Thr Glu Arg Ser Val Glu Ser Ser Ser
    755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
    835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Thr Lys Ser
                885                 890                 895

Lys Ser His Phe
            900

(2) INFORMATION FOR SEQ ID NO: 21:

(i) SEQUENCE CHARACTERISTICS:
        (A) LENGTH: 914 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 21:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
                35                  40                  45
```

```
Leu Lys Leu Leu Asn Gln Lys Lys Gly Pro Ser Gln Cys Pro Leu Cys
    50                  55                  60
Lys Asn Asp Ile Thr Lys Arg Ser Leu Gln Glu Ser Thr Arg Phe Ser
 65              70                  75                      80
Gln Leu Val Glu Glu Leu Leu Lys Ile Ile Cys Ala Phe Gln Leu Asp
                 85                  90                  95
Thr Gly Leu Glu Tyr Ala Asn Ser Tyr Asn Phe Ala Lys Lys Glu Asn
                100                 105                 110
Asn Ser Pro Glu His Leu Lys Asp Glu Val Ser Ile Ile Gln Ser Met
            115                 120                 125
Gly Tyr Arg Asn Arg Ala Lys Arg Leu Leu Gln Ser Glu Pro Glu Asn
            130                 135                 140
Pro Ser Leu Gln Glu Thr Ser Leu Ser Val Gln Leu Ser Asn Leu Gly
145                 150                 155                 160
Thr Val Arg Thr Leu Arg Thr Lys Gln Arg Ile Gln Pro Gln Lys Thr
                165                 170                 175
Ser Val Tyr Ile Glu Leu Gly Ser Asp Ser Ser Glu Asp Thr Val Asn
                180                 185                 190
Lys Ala Thr Tyr Cys Ser Val Gly Asp Gln Glu Leu Leu Gln Ile Thr
                195                 200                 205
Pro Gln Gly Thr Arg Asp Glu Ile Ser Leu Asp Ser Ala Lys Lys Ala
210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
                260                 265                 270
Pro Cys Gly Thr Asn Thr His Ala Ser Ser Leu Gln His Glu Asn Ser
                275                 280                 285
Ser Leu Leu Leu Thr Lys Asp Arg Met Asn Val Glu Lys Ala Glu Phe
290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
                340                 345                 350
Trp Asn Lys Gln Lys Leu Pro Cys Ser Glu Asn Pro Arg Asp Thr Glu
                355                 360                 365
Asp Val Pro Trp Ile Thr Leu Asn Ser Ser Ile Gln Lys Val Asn Glu
                370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
                420                 425                 430
Ala Ser Asp Pro His Glu Ala Leu Ile Cys Lys Ser Glu Arg Val His
                435                 440                 445
Ser Lys Ser Val Glu Ser Asn Ile Glu Asp Lys Ile Phe Gly Lys Thr
450                 455                 460
```

```
Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
    755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
```

```
                885                 890                 895
Pro Lys Val Thr Phe Glu Cys Glu Gln Lys Glu Glu Asn Gln Gly Lys
                    900                 905                 910
Asn Glu
```

(2) INFORMATION FOR SEQ ID NO: 22:

(i) SEQUENCE CHARACTERISTICS:
        (A) LENGTH: 1202 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 22:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
            115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
            195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320
```

-continued

```
Trp Ala Gly Ser Lys Glu Thr Cys Asn Asp Arg Arg Thr Pro Ser Thr
            325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
            355                 360                 365
Asp Val Pro Trp Ile Thr Leu Asn Ser Ser Ile Gln Lys Val Asn Glu
            370                 375                 380
Trp Phe Ser Arg Ser Asp Glu Leu Leu Gly Ser Asp Ser His Asp
385                 390                 395                 400
Gly Glu Ser Glu Ser Asn Ala Lys Val Ala Asp Val Leu Asp Val Leu
            405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
            435                 440                 445
Ser Lys Ser Val Glu Ser Asn Ile Glu Asp Lys Ile Phe Gly Lys Thr
            450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
            485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
            515                 520                 525
Pro Glu Met Ile Asn Gln Gly Thr Asn Gln Thr Glu Gln Asn Gly Gln
            530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
            565                 570                 575
Glu Ser Ala Phe Lys Thr Lys Ala Glu Pro Ile Ser Ser Ser Ile Ser
            580                 585                 590
Asn Met Glu Leu Glu Leu Asn Ile His Asn Ser Lys Ala Pro Lys Lys
            595                 600                 605
Asn Arg Leu Arg Arg Lys Ser Ser Thr Arg His Ile His Ala Leu Glu
            610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Lys Tyr Asn
            645                 650                 655
Gln Met Pro Val Arg His Ser Arg Asn Leu Gln Leu Met Glu Gly Lys
            660                 665                 670
Glu Pro Ala Thr Gly Ala Lys Lys Ser Asn Lys Pro Asn Glu Gln Thr
            675                 680                 685
Ser Lys Arg His Asp Ser Asp Thr Phe Pro Glu Leu Lys Leu Thr Asn
            690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
            725                 730                 735
```

-continued

```
Thr Val Lys Val Ser Asn Asn Ala Glu Asp Pro Lys Asp Leu Met Leu
        740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
                835                 840                 845

Glu Ser Glu Leu Asp Ala Gln Tyr Leu Gln Asn Thr Phe Lys Val Ser
        850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
                900                 905                 910

Asn Glu Ser Asn Ile Lys Pro Val Gln Thr Val Asn Ile Thr Ala Gly
                915                 920                 925

Phe Pro Val Val Gly Gln Lys Asp Lys Pro Val Asp Asn Ala Lys Cys
                930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
                980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val Ser
        1010                1015                1020

Thr Ile Ser Arg Asn Asn Ile Arg Glu Asn Val Phe Lys Glu Ala Ser
1025                1030                1035                1040

Ser Ser Asn Ile Asn Glu Val Gly Ser Ser Thr Asn Glu Val Gly Ser
                1045                1050                1055

Ser Ile Asn Glu Ile Gly Ser Ser Asp Glu Asn Ile Gln Ala Glu Leu
                1060                1065                1070

Gly Arg Asn Arg Gly Pro Lys Leu Asn Ala Met Leu Arg Leu Gly Val
                1075                1080                1085

Leu Gln Pro Glu Val Tyr Lys Gln Ser Leu Pro Gly Ser Asn Cys Lys
        1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                1125                1130                1135

Met Gly Ser Ser His Ala Ser Gln Val Cys Ser Glu Thr Pro Asp Asp
                1140                1145                1150

Leu Leu Asp Asp Gly Glu Ile Lys Glu Asp Thr Ser Phe Ala Glu Asn
```

```
            1155                 1160                      1165
Asp Ile Lys Glu Ser Ser Ala Val Phe Ser Lys Ser Val Gln Lys Gly
            1170                 1175            1180

Glu Leu Ser Arg Ser Pro Ser Pro Phe Thr His Thr His Leu Ala Gln
1185                1190                1195                1200

Gly Tyr (2) INFORMATION FOR SEQ ID NO: 23:

(i) SEQUENCE CHARACTERISTICS:
        (A) LENGTH: 1363 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 23:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300
```

```
Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
            325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
            370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
            530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Met Glu Leu Glu Leu Asn Ile His Asn Ser Lys Ala Pro Lys Lys
            595                 600                 605

Asn Arg Leu Arg Arg Lys Ser Ser Thr Arg His Ile His Ala Leu Glu
            610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
            690                 695                 700

Ala Pro Gly Ser Phe Thr Lys Cys Ser Asn Thr Ser Glu Leu Lys Glu
705                 710                 715                 720
```

```
Phe Val Asn Pro Ser Leu Pro Arg Glu Glu Lys Glu Lys Leu Glu
            725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
            770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
                900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
            930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
            995                 1000                1005

Ser Pro Glu Arg Glu Met Gly Asn Glu Asn Ile Pro Ser Thr Val Ser
    1010                1015                1020

Thr Ile Ser Arg Asn Asn Ile Arg Glu Asn Val Phe Lys Glu Ala Ser
1025                1030                1035                1040

Ser Ser Asn Ile Asn Glu Val Gly Ser Ser Thr Asn Glu Val Gly Ser
                1045                1050                1055

Ser Ile Asn Glu Ile Gly Ser Ser Asp Glu Asn Ile Gln Ala Glu Leu
                1060                1065                1070

Gly Arg Asn Arg Gly Pro Lys Leu Asn Ala Met Leu Arg Leu Gly Val
                1075                1080                1085

Leu Gln Pro Glu Val Tyr Lys Gln Ser Leu Pro Gly Ser Asn Cys Lys
    1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                1125                1130                1135

Met Gly Ser Ser His Ala Ser Gln Val Cys Ser Glu Thr Pro Asp Asp
```

-continued

```
                1140                1145                1150
Leu Leu Asp Asp Gly Glu Ile Lys Glu Asp Thr Ser Phe Ala Glu Asn
                1155                1160                1165
Asp Ile Lys Glu Ser Ser Ala Val Phe Ser Lys Ser Val Gln Lys Gly
        1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
                1205                1210                1215
Ser Ser Glu Asp Glu Glu Leu Pro Cys Phe Gln His Leu Leu Phe Gly
                1220                1225                1230
Lys Val Asn Asn Ile Pro Ser Gln Ser Thr Arg His Ser Thr Val Ala
            1235                1240                1245
Thr Glu Cys Leu Ser Lys Asn Thr Glu Glu Asn Leu Leu Ser Leu Lys
        1250                1255                1260
Asn Ser Leu Asn Asp Cys Ser Asn Gln Val Ile Leu Ala Lys Ala Ser
1265                1270                1275                1280
Gln Glu His His Leu Ser Glu Gly Thr Lys Cys Ser Ala Ser Leu Phe
                1285                1290                1295
Ser Ser Gln Cys Ser Glu Leu Glu Asp Leu Thr Ala Asn Thr Asn Thr
            1300                1305                1310
Gln Asp Pro Phe Leu Ile Gly Ser Ser Lys Gln Met Arg His Gln Ser
        1315                1320                1325
Glu Ser Gln Gly Val Gly Leu Ser Asp Lys Glu Leu Val Ser Asp Asp
    1330                1335                1340
Glu Glu Arg Gly Thr Gly Leu Glu Glu Asn Lys Lys Ser Lys Ala Trp
1345                1350                1355                1360
Ile Gln Thr
```

(2) INFORMATION FOR SEQ ID NO: 24:

(i) SEQUENCE CHARACTERISTICS:
        (A) LENGTH: 1852 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 24:

```
Met Asp Leu Ser Ala Leu Arg Val Glu Val Gln Asn Val Ile Asn
1               5                   10                  15
Ala Met Gln Lys Ile Leu Glu Cys Pro Ile Cys Leu Glu Leu Ile Lys
                20                  25                  30
Glu Pro Val Ser Thr Lys Cys Asp His Ile Phe Cys Lys Phe Cys Met
            35                  40                  45
Leu Lys Leu Leu Asn Gln Lys Lys Gly Pro Ser Gln Cys Pro Leu Cys
        50                  55                  60
Lys Asn Asp Ile Thr Lys Arg Ser Leu Gln Glu Ser Thr Arg Phe Ser
65                  70                  75                  80
Gln Leu Val Glu Glu Leu Leu Lys Ile Ile Cys Ala Phe Gln Leu Asp
                85                  90                  95
Thr Gly Leu Glu Tyr Ala Asn Ser Tyr Asn Phe Ala Lys Lys Glu Asn
            100                 105                 110
Asn Ser Pro Glu His Leu Lys Asp Glu Val Ser Ile Ile Gln Ser Met
        115                 120                 125
```

```
Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
                180                 185                 190

Lys Ala Thr Tyr Cys Ser Val Gly Asp Gln Glu Leu Leu Gln Ile Thr
            195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
                260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
                340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
                500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
    530                 535                 540
```

-continued

```
Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
```

-continued

```
                965                 970                 975
Pro Tyr Arg Ile Pro Pro Leu Phe Pro Ile Lys Ser Phe Val Lys Thr
                980                 985                 990
Lys Cys Lys Lys Asn Leu Leu Glu Glu Asn Phe Glu Glu His Ser Met
            995                1000                1005
Ser Pro Glu Arg Glu Met Gly Asn Glu Asn Ile Pro Ser Thr Val Ser
        1010                1015                1020
Thr Ile Ser Arg Asn Asn Ile Arg Glu Asn Val Phe Lys Glu Ala Ser
1025                1030                1035                1040
Ser Ser Asn Ile Asn Glu Val Gly Ser Ser Thr Asn Glu Val Gly Ser
                1045                1050                1055
Ser Ile Asn Glu Ile Gly Ser Ser Asp Glu Asn Ile Gln Ala Glu Leu
                1060                1065                1070
Gly Arg Asn Arg Gly Pro Lys Leu Asn Ala Met Leu Arg Leu Gly Val
                1075                1080                1085
Leu Gln Pro Glu Val Tyr Lys Gln Ser Leu Pro Gly Ser Asn Cys Lys
            1090                1095                1100
His Pro Glu Ile Lys Lys Gln Glu Tyr Glu Glu Val Val Gln Thr Val
1105                1110                1115                1120
Asn Thr Asp Phe Ser Pro Tyr Leu Ile Ser Asp Asn Leu Glu Gln Pro
                1125                1130                1135
Met Gly Ser Ser His Ala Ser Gln Val Cys Ser Glu Thr Pro Asp Asp
                1140                1145                1150
Leu Leu Asp Asp Gly Glu Ile Lys Glu Asp Thr Ser Phe Ala Glu Asn
            1155                1160                1165
Asp Ile Lys Glu Ser Ser Ala Val Phe Ser Lys Ser Val Gln Lys Gly
        1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
                1205                1210                1215
Ser Ser Glu Asp Glu Glu Leu Pro Cys Phe Gln His Leu Leu Phe Gly
            1220                1225                1230
Lys Val Asn Asn Ile Pro Ser Gln Ser Thr Arg His Ser Thr Val Ala
            1235                1240                1245
Thr Glu Cys Leu Ser Lys Asn Thr Glu Glu Asn Leu Leu Ser Leu Lys
        1250                1255                1260
Asn Ser Leu Asn Asp Cys Ser Asn Gln Val Ile Leu Ala Lys Ala Ser
1265                1270                1275                1280
Gln Glu His His Leu Ser Glu Glu Thr Lys Cys Ser Ala Ser Leu Phe
                1285                1290                1295
Ser Ser Gln Cys Ser Glu Leu Glu Asp Leu Thr Ala Asn Thr Asn Thr
            1300                1305                1310
Gln Asp Pro Phe Leu Ile Gly Ser Ser Lys Gln Met Arg His Gln Ser
        1315                1320                1325
Glu Ser Gln Gly Val Gly Leu Ser Asp Lys Glu Leu Val Ser Asp Asp
    1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
                1365                1370                1375
Ser Val Ser Glu Asp Cys Ser Gly Leu Ser Ser Gln Ser Asp Ile Leu
            1380                1385                1390
```

-continued

```
Thr Thr Gln Gln Arg Asp Thr Met Gln His Asn Leu Ile Lys Leu Gln
        1395                1400                1405

Gln Glu Met Ala Glu Leu Glu Ala Val Leu Gln His Gly Ser Gln
    1410                1415                1420

Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Ala Val Leu Thr
                1445                1450                1455

Ser Gln Lys Ser Ser Glu Tyr Pro Ile Ser Gln Asn Pro Glu Gly Leu
        1460                1465                1470

Ser Ala Asp Lys Phe Glu Val Ser Ala Asp Ser Ser Thr Ser Lys Asn
        1475                1480                1485

Lys Glu Pro Gly Val Glu Arg Ser Ser Pro Ser Lys Cys Pro Ser Leu
    1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
                1525                1530                1535

Gln Gln Leu Glu Glu Ser Gly Pro His Asp Leu Thr Glu Thr Ser Tyr
        1540                1545                1550

Leu Pro Arg Gln Asp Leu Glu Gly Thr Pro Tyr Leu Glu Ser Gly Ile
        1555                1560                1565

Ser Leu Phe Ser Asp Asp Pro Glu Ser Asp Pro Ser Glu Asp Arg Ala
        1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Ser Pro Ala Ala
                1605                1610                1615

Ala His Thr Thr Asp Thr Ala Gly Tyr Asn Ala Met Glu Glu Ser Val
                1620                1625                1630

Ser Arg Glu Lys Pro Glu Leu Thr Ala Ser Thr Glu Arg Val Asn Lys
        1635                1640                1645

Arg Met Ser Met Val Val Ser Gly Leu Thr Pro Glu Glu Phe Met Leu
    1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
                1685                1690                1695

Cys Glu Arg Thr Leu Lys Tyr Phe Leu Gly Ile Ala Gly Gly Lys Trp
                1700                1705                1710

Val Val Ser Tyr Phe Trp Val Thr Gln Ser Ile Lys Glu Arg Lys Met
        1715                1720                1725

Leu Asn Glu His Asp Phe Glu Val Arg Gly Asp Val Val Asn Gly Arg
    1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
                1765                1770                1775

Thr Asp Gln Leu Glu Trp Met Val Gln Leu Cys Gly Ala Ser Val Val
                1780                1785                1790

Lys Glu Leu Ser Ser Phe Thr Leu Gly Thr Gly Val His Pro Ile Val
        1795                1800                1805
```

```
                                 -continued

Val Val Gln Pro Asp Ala Trp Thr Glu Asp Asn Gly Phe His Ala Ile
    1810            1815            1820

Gly Gln Met Cys Glu Ala Pro Val Val Thr Arg Glu Trp Val Leu Asp
1825            1830            1835            1840

Ser Val Ala Leu Tyr Gln Cys Gln Glu Leu Asp Thr
                1845            1850
```